United States Patent
Atwood

(10) Patent No.: US 8,709,224 B2
(45) Date of Patent: Apr. 29, 2014

(54) METHODS FOR THE DETECTION OF BIOLOGICALLY RELEVANT MOLECULES AND THEIR INTERACTION CHARACTERISTICS

(76) Inventor: Christopher Gordon Atwood, San Diego, CA (US)

( * ) Notice: Subject to any disclaimer, the term of this patent is extended or adjusted under 35 U.S.C. 154(b) by 0 days.

(21) Appl. No.: 13/498,141

(22) PCT Filed: Feb. 15, 2011

(86) PCT No.: PCT/US2011/024882
§ 371 (c)(1),
(2), (4) Date: Mar. 25, 2012

(87) PCT Pub. No.: WO2011/106198
PCT Pub. Date: Sep. 1, 2011

(65) Prior Publication Data
US 2012/0181176 A1     Jul. 19, 2012

Related U.S. Application Data

(60) Provisional application No. 61/338,676, filed on Feb. 23, 2010.

(51) Int. Cl.
*G01N 27/00* (2006.01)
*C12Q 1/68* (2006.01)

(52) U.S. Cl.
USPC ...... 204/450; 435/7.1; 435/287.1; 435/287.2; 422/68.1; 422/82.01; 422/52; 436/149; 436/518; 204/400

(58) Field of Classification Search
USPC ............... 204/450, 600, 400, 411, 412, 456; 435/287.1, 4–40.52, 7.1, 287.2; 422/82.01, 68.1, 52; 436/149, 518
See application file for complete search history.

(56) References Cited

U.S. PATENT DOCUMENTS

| 5,212,065 A | 5/1993 | Pegg et al. |
| 6,541,213 B1 | 4/2003 | Weigl et al. |
| 6,548,311 B1 | 4/2003 | Knoll |

(Continued)

FOREIGN PATENT DOCUMENTS

| CN | 1413261 | 4/2003 |
| CN | 101454667 | 6/2009 |

(Continued)

OTHER PUBLICATIONS

European Search Report and Opinion for EP11747868.5 issued Jun. 6, 2013, 13 pages.

(Continued)

*Primary Examiner* — Jennifer Dieterle
(74) *Attorney, Agent, or Firm* — Morrison & Foerster LLP

(57) ABSTRACT

Methods for the detection of biologically relevant molecules that comprise concentrating such molecules into microscopic holes in a sheet of chemically inert material, restricting the openings, and measuring the electric current through the holes or the fluorescence near the hole openings. The electric current or fluorescence will change as the molecules diffuse out of the holes, providing a measure of the diffusion rate and thereby detecting the presence and characteristics of the molecules. For molecules that interact, the diffusion rate will be slower than for molecules that do not interact, yielding a determination of the molecular interaction. Capping the population of holes and inserting into a mass spectrometer allows identification of the molecules.

18 Claims, 48 Drawing Sheets

(56) References Cited

U.S. PATENT DOCUMENTS

| | | |
|---|---|---|
| 6,645,558 B2 | 11/2003 | Park et al. |
| 6,825,045 B2 | 11/2004 | Haglund, Jr. et al. |
| 7,069,445 B2 | 6/2006 | Garman |
| 7,144,553 B2 | 12/2006 | Lewis et al. |
| 7,192,752 B2 | 3/2007 | Xu et al. |
| 7,271,007 B2 | 9/2007 | Weigl et al. |
| 7,297,312 B2 | 11/2007 | Ding et al. |
| 7,306,672 B2 | 12/2007 | Hansen et al. |
| 7,550,257 B2 | 6/2009 | Hawkins et al. |
| 7,550,267 B2 | 6/2009 | Hawkins et al. |
| 7,704,322 B2 | 4/2010 | Hansen et al. |
| 7,732,127 B2 | 6/2010 | Wang et al. |
| 2003/0234386 A1 | 12/2003 | Konermann et al. |
| 2005/0109621 A1 | 5/2005 | Hauser et al. |
| 2005/0136419 A1 | 6/2005 | Lee |
| 2006/0115905 A1 | 6/2006 | Hatch et al. |
| 2007/0275480 A1* | 11/2007 | Brander et al. ............... 436/501 |
| 2007/0298511 A1* | 12/2007 | Kang et al. ................... 436/150 |
| 2008/0101988 A1* | 5/2008 | Kang et al. ..................... 422/58 |
| 2008/0113353 A1 | 5/2008 | Park et al. |
| 2008/0145856 A1 | 6/2008 | Lehmann |
| 2008/0182273 A1 | 7/2008 | Hansen et al. |
| 2009/0048120 A1 | 2/2009 | Park et al. |
| 2009/0053732 A1 | 2/2009 | Vermesh et al. |
| 2010/0261615 A9 | 10/2010 | Park et al. |
| 2010/0263732 A1 | 10/2010 | Hansen et al. |

FOREIGN PATENT DOCUMENTS

| | | | |
|---|---|---|---|
| WO | WO-01/46458 | | 6/2001 |
| WO | WO-01/71317 | | 9/2001 |
| WO | WO-2007/076017 | | 7/2007 |
| WO | WO 2008/051308 | * | 5/2008 |
| WO | WO 2009/020682 A1 | * | 2/2009 |

OTHER PUBLICATIONS

Examination Report (China) for CN201180007918.3, issued Jul. 15, 2013, 19 pages.
International Preliminary Report on Patentability for PCT/US2011/024882, issued Aug. 28, 2012, 6 pages.
International Search Report for PCT/US2011/024882, mailed May 26, 2011, 2 pages.
Written Opinion for PCT/US2011/024882, mailed May 26, 2011, 5 pages.
Informal Response to Written Opinion for PCT/US2011/024882 mailed May 26, 2011, dated Jul. 15, 2011, 14 pages.

* cited by examiner

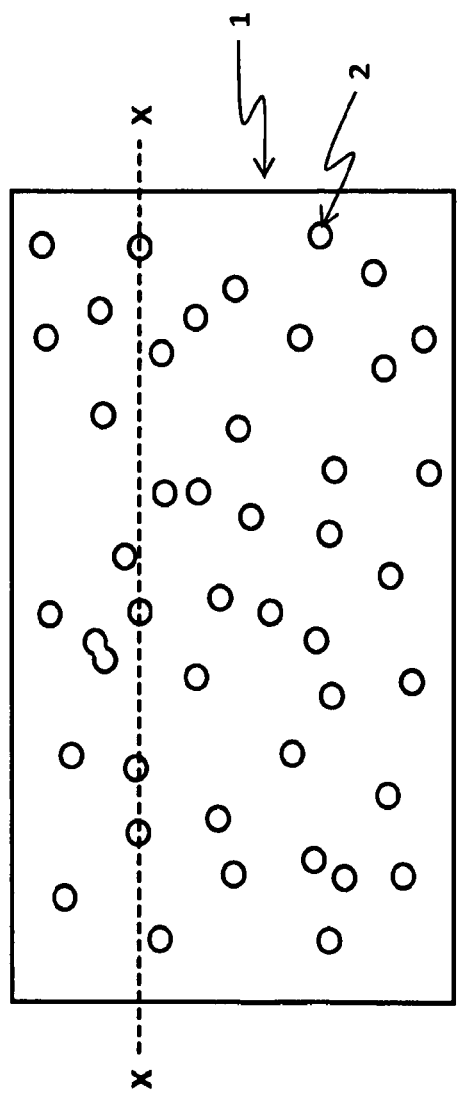
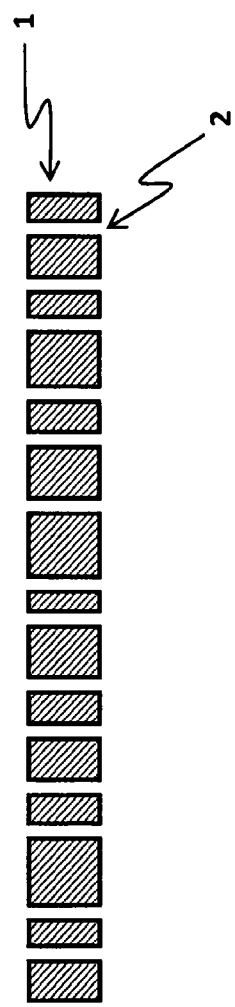

METHODS FOR THE DETECTION OF BIOLOGICALLY RELEVANT MOLECULES AND THEIR INTERACTION CHARACTERISTICS

1. CROSS-REFERENCE TO RELATED APPLICATION

This application claims the benefit under 35 U.S.C. Section 119(e) of U.S. Provisional Patent Application No. 61/338,676 filed Feb. 23, 2010, which provisional application is incorporated herein by reference in its entirety.

BACKGROUND OF THE INVENTION

1. Field of the Invention

This invention relates to methods for the detection of analyte particles, and determining their interaction characteristics within complex media. More particularly, this invention relates to diffusion immunoassays and their functional equivalents.

2. Description of the Related Art

Biologically relevant molecules, such as proteins and nucleic acids, are commonly associated with biological systems, where they form a complex network of interactions for the performance of tasks such as cell replication, metabolism, self-regulation, intercellular signaling, and immune response. Diseases distort this network, and understanding this distortion is fundamental to early detection of disease and chemical repair of the distortion through drug therapy. There are a number of existing techniques for identifying and characterizing these large molecules to gain an understanding of the interaction network, but each suffers from particular limitations. Techniques used for nucleic acids, such as DNA, have been largely successful due to their analytically favorable properties, but proteins are chemically and physically diverse. This diversity results in analytical techniques that are by necessity narrowly focused, when a broad technique would be ranch more helpful in characterizing a complex protein network. Furthermore, proteins may be functionally significant at even undetectable concentrations, yet cannot be amplified with the ease of nucleic acids, necessitating techniques that have a high intrinsic sensitivity.

Genetic Methods

Protein interactions can be investigated by using classical genetics. Different mutations are combined into in the same cell or organism, and then the resulting phenotype is observed. This ensures that protein interactions occur in their near perfectly native environments. Unfortunately, these methods are applicable only to a small group of proteins, and can not be used for exploring the whole proteome. Furthermore, phenotypic changes can be caused for a multitude of reasons related to the gene mutations, and thus protein interactions suggested by experimental results would require confirmation at the biochemical level.

Bioinformatic Methods

Protein interactions can be investigated by using comparative genomics for the functional, annotation of proteins. Currently, there are three major techniques. The first technique is called Domain Fusion (or Rosetta Stone), which assumes that protein domains are structurally and functionally independent units that can operate as discrete polypeptides. The second technique is based on the operon organization of bacterial genes, where such genes are often, functionally related even if their actual sequences are disparate. The third technique uses phylogenic profiling, exploiting the evolutionary conservation of genes involved together in a particular function. Unfortunately, these bioinformatic methods require a complete genome sequence, and are generally limited to bacteria or other organisms with well-defined operons. Furthermore, the results are not conclusive evidence of specific protein interactions, and require confirmation at the biochemical level.

Affinity-Based Methods

Protein interactions can be investigated at the biochemical level by directly determining affinity between, a protein and candidate interaction partners, such as in immunoassays. Proteins are immobilized onto a stationary phase or flat glass surface, and a mixture of potential complementary ligands is flooded over the immobilized protein. Binding is indicated by fluorescent or radioactive probes chemically attached to the ligands, which are then imaged. Unfortunately, protein functionality can be severely restricted by the immobilization process. A related technique chemically labels the proteins themselves and then floods them, over a surface coated with immobilized ligands. However, this process suffers from the fact that proteins do not label uniformly with the same efficiency, and the chemical attachment of the labels can interfere with the range of the protein's interactions. Furthermore, attachment of labels can adversely affect protein solubility, and fluorescent probes may be quenched by the attachment. Detection may also be performed by electrochemical amperometry (e.g. U.S. Pat. No. 7,297,312), but the drawbacks remain.

Diffusion Immunoassays may use a pair of adjacent fluid flows in a microcapillary channel (e.g. U.S. Pat. No. 6,541,213, U.S. Pat. No. 7,271,007, U.S. Pat. No. 7,306,672, U.S. Pat. No. 7,060,446, U.S. Pat. No. 7,704,322, and U.S. patent applications US 2010/0263732, US 2008/0182273, US 2003/0096310, US 2009/0053732, and US 2003/0234356), or functional equivalents, where interactions between components in the two fluids at the flow interface causes a change in diffusion characteristics that affects the concentration profile near the fluid interface. Detection of the concentration profile provides information on the interactions. This avoids complications associated with a stationary phase, but still prefers the use of labeling, and only one measurement per sample is practical (i.e., it is non-cyclable). The use of multivalent reactants (e.g. U.S. Pat. No. 7,550,267) allows the use of components with a greater disparity of diffusion coefficients, but the measurement drawbacks of labeling and non-cyclability remain. Related devices using porous membranes (e.g. U.S. Pat. No. 5,212,065) suffer from the same disadvantages. The use of a thin polymer layer over an array of electrochemical sensors (e.g. U.S. Pat. No. 7,144,553) is capable of determining diffusion characteristics via time delays involved in permeating the polymer, but does not concentrate the analyte in a narrow hole (thereby enhancing sensitivity), and is not amenable to cycling the analyte towards and away from the sensor via hydrodynamic flow. Diffusion may be measured by optically tracking an analyte system (e.g. US 2008/0145856), but this has the drawback of preferring the use of labeling technology. Diffusion may be measured by detection of penetration depth into a hydrogel (e.g. US 2006/0115905), but this has the drawback of preferring the use of labeling technology.

Microchannel Conductometry measures changes to transverse conductance as protein molecules pass through a microchannel, and this has been described as possibly useful for label-free protein interaction detection (e.g. US 2005/0109621). However, that method only indirectly determines diffusion properties, and is not amenable cycling the measurements. Conductometry has also been used for label-free cell culture monitoring (e.g. U.S. Pat. No. 7,732,127 and U.S.

Pat. No. 7,192,752), but these are not direct measurements of proteins and their interactions. The use of nanogaps (e.g. US 2005/0136419) avoids certain double-layer complications of electrochemical measurements, but has the drawback of preferring the use of tethering technology.

Physical Methods

Protein interactions can be investigated at the physical level. The techniques of X-ray crystallography and nuclear magnetic resonance (NMR) determine the locations of protein atoms within the molecule, and the resulting 3-dimensional map can be used to suggest which other molecules are likely to fit into its topology and charge distribution. Unfortunately, X-ray crystallography requires the growth of protein crystals for each protein to be investigated, which is a difficult and time consuming process, and the crystal environment is drastically different than the aqueous environment in which the protein functions. NMR requires a large quantity of purified protein, and analysis of the resulting complex data can be inconclusive.

The technique of surface plasmon resonance uses protein adherence to metal films, but this can adversely affect, protein functionality.

The technique of Fluorescence Resonance Energy Transfer (FRET) takes advantage of energy transfer that can occur between nearby fluorophores when the emission spectrum of one fluorophore overlaps the excitation of the other fluorophore. By labeling one candidate interaction partner with one fluorophore, and the other candidate interaction partner with another fluorophore, then interactions will be indicated by an increase in the fluorescence of one fluorophore at the expense of the other. This works well with even transient interactions. Unfortunately, this requires chemical, attachment of a fluorophore to every protein, which may adversely affect protein functionality.

The technique of atomic force microscopy of dendron-isolated analytes (e.g. U.S. Pat. No. 6,645,558, US 2008/0113353, US 2009/0048120 and US 2010/0261615) can detect individual analyte molecules, but requires tethering bonds and extensive sample preparation.

Standard Expression Libraries

Protein interactions can be investigated through the use of libraries of cDNA that produce bait proteins that can be labeled and used as a probe. Typically, the bait proteins are produced through the use of phage particles. The technique allows for the association of a bait protein, with its corresponding cDNA, but suffers from the major drawback of a low throughput; screenings for each bait protein are required. Furthermore, the production of the bait proteins is not under native conditions, leading to possibly erroneous folding and false negatives.

Phage Interaction Display

Protein interactions can be investigated through the use of an expression cloning strategy. A cDNA sequence is inserted into a phage protein coat gene, and cultured in bacterial cells. The phage than expresses a new protein on its coat, which then can be used for protein interaction analyses. If a mixture of such phages interacts with an immobilized labeled protein, in a well, the well can be rinsed, to leave behind only the interacting phages, along with the cDNA sequences that formed them. The cDNA sequences in turn can then, be massively amplified by bacterial infection. This technique is highly amenable to automated parallel screenings. Unfortunately, as with standard expression libraries, the proteins are not formed under native conditions. Also, the technique is limited to short peptides that can be formed on the phage surface.

Yeast Two-Hybrid System

Protein interactions can be investigated through the use of transcription factors within yeast cells, which is a more native environment for protein expression than in vitro. A protein under investigation is expressed in a haploid yeast cell as a fusion with the DNA-binding domain from a transcription factor. Another protein, is expressed in another haploid yeast cell as a fusion, with the transactivation domain of the same transcription factor. Mating the two yeast strains into a diploid strain allows the two proteins to interact. If they do interact, the transcription factor will be assembled, causing a test gene to be activated. The technique is amenable to large-scale screenings, but there are several drawbacks. Experimental repeatability is quite low, suggesting inordinate sensitivity to environmental conditions, or that the screens were not comprehensive. There are a significant number of failures to detect interactions well-established from other more specific techniques, indicating a high level of false negatives. Lastly, a significant number of detected interactions are determined to not be valid by further analysis, indicating a high, level of false positives.

All publications referred to herein are hereby incorporated by reference in their entirety to the extent not inconsistent herewith.

SUMMARY OF THE INVENTION

The methods described herein use a combination of existing technologies comprising spheroids, magnetic fields, fluorescence, optics, filter technology, gel technology, chemistry, electrochemistry, chromatography, and Matrix-Assisted Laser Desorption ionization (MALDI), to detect and characterize analyte particles (e.g. biologically relevant molecules), to characterize any structural changes to analyte particles, and to identify their interactions.

In one method in accordance with the invention, analyte particles are trapped within microscopic reservoirs in an ionic environment (such as aqueous saline), by means such as solvent flow or an electric field. Once trapped, the means of trapping is terminated, and the electrical conductivity of the reservoir is measured as the analyte particles diffuse out of the reservoirs. The electrical conductivity is a measure of the ease of ion flow. Since the ion flow is restricted by the analyte particles, the conductivity will drop as the analyte particles diffuse out of the reservoirs. The time frame over which the conductivity drops provides a measure of the analyte particle diffusion coefficient. The diffusion coefficient in turn provides a measure of the analyte particle characteristics, such as its size and shape. The use of an electric field to supplement or suppress the diffusion can also be used to study the charge characteristics of the analyte particle. Furthermore, two analyte particles that exhibit a binding interaction will display a reduction in the diffusion coefficient relative to the individual analyte particles; the reduction provides a measure of the binding interaction. After the analyte particles have diffused out of the reservoirs, they may be trapped again within the reservoirs, so that the measurement can be repeated in a continual cycle.

In another method that is similar to the first method, fluorescence is used instead of electrical, conductivity to provide a measure of the analyte particle diffusion coefficient. The fluorescence can be used either by causing the restriction of ion flow in an electric field to delay the onset of fluorescence, or by causing restriction of the flow of fluorescent particles themselves.

Further methods can involve physically trapping the analyte particles within the reservoirs, so that the reservoirs can be moved en masse into a vacuum chamber of a mass spectrometer while remaining in an aqueous environment. Laser ablation can then be used to vaporize the aqueous matrix of the analyte particles to provide a mass spectrometry sample with improved control over the molecular fragmentation.

The methods of the invention can be used for finding binary, ternary, or greater interactions, for analyte particles having a large size difference, and for situations where one or more of the participating analyte particles are in a lipid environment. Such methods may find widespread applicability for biomarker discovery, drug discovery, and drug evaluation. A strong advantage of these methods over existing methods is that it is label-free and tether-tree, ensuring that analyte particles interact in their native state without chemically attached labels or tethers; labels and tethers may still be used, but they are not required. The methods are also largely independent of pH or other solution characteristics, can be used with opaque complex aqueous mixtures, can use extremely small sample volumes, and allow the measurements to be cycled (i.e. repeated) for enhanced sensitivity.

In accordance with one aspect of the invention a method for the detection of analyte particle presence, characteristics, and interactions, comprises: providing a sheet of material having a plurality of through holes that are of substantially similar diameter; restricting the hole openings of at least one face of the material; inserting analyte particles into a sub-population of said holes; applying an electric field through said through holes containing the analyte particles; measuring a change in electric current flow with time indicative of the diffusion rates of said analyte particles; and wherein the diffusion rates of said analyte particles provide a measure of analyte particle presence, characteristics, and interaction.

The sheet of material can comprise a polycarbonate; a track-etched polycarbonate; a polymer drilled with a plurality of holes; a polymer chemically etched with a plurality of holes; a glass drilled with a plurality of holes; a glass chemically etched with a plurality of holes; a perforated polymer film; a perforated monolayer film or a perforated multilayer film. Typically the material is electrically insulating and is substantially chemically inert. The sheet of material can be of a thickness in a range 500 nm to 1000000 nm. Alternatively it is of a thickness in a range 1 nm to 10 cm. The through holes can be of diameter 10 nm to 5000 nm. Alternatively the through holes can be of diameter 1 nm to 1 cm. In one arrangement an inner surface of the through holes is chemically derivatized. Alternatively an outer surface of the through holes can be chemically derivatized. The through holes can be filled with a gel.

In one embodiment the hole openings are restricted by applying a layer of gel in contact with a surface of said sheet of material. The gel can comprise a gelatin; an agarose; a polyacrylamide; a polyacrylate; a permeable polymer; a permeable copolymer; a starch; an aerogel; a collodion; a dialysis membrane; a fluid, immiscible with the analyte particle matrix; any of the above-listed materials in a chemically modified form; any of the above-listed materials embedded with particles and combinations thereof.

In another embodiment the hole openings are restricted using spheroids having a diameter configured to cause substantial restriction to fluid flow through the holes. The spheroids can be held in position by gravity; centripetal, force; centrifugal force; hydrodynamic pressure; hydrostatic pressure; chemical bonds or using a gel matrix. Depending on the composition, of the spheroids the spheroids can be held in position by applying an electric field or by applying a magnetic field gradient.

Where the spheroids are held in position using a gel matrix the method can further comprise removing the spheroids from the gel matrix.

Advantageously the electric current flow is measured using an amperometer that is configured to measure the electric current through a selected area of the sheet, at a rate sufficient for the diffusion rates being measured.

The said selected area can be selected using an insulating tube with one end in physical contact with the sheet of material; an insulating sheet with a hole that is applied to the surface of said sheet of material or an insulating water-immiscible fluid that is applied to the surface of the sheet of material.

According to another aspect of the invention a method for tire detection of analyte particle presence, characteristics, and interactions, comprises: providing a sheet of material having a plurality of through holes that are of substantially similar diameter; restricting the hole openings of at least one face of the material; inserting analyte particles into a sub-population of said holes; passing a migration, force axially through said through holes containing the analyte particles; measuring a change in fluorescence with time indicative of the diffusion rates of said analyte particles; and wherein the diffusion rates of said analyte particles provide a measure of analyte particle presence, characteristics, and interaction.

Preferably fluorescence is measured by a photometric system capable of measuring the fluorescence of a selected area of the sheet, at a rate sufficient for the diffusion, rates being measured.

According to a further aspect of the invention a method for identification, of analyte particles, comprises: providing a sheet of material having a plurality of through holes that are of substantially similar diameter; restricting the hole openings of at least one face of the material; inserting analyte particles into a sub-population of said holes; closing substantially said hole openings; inserting said sheet of material into a mass spectrometer; ablating a selected area of said sheet of material; ionizing the resulting products of ablation; measuring the mass/charge ratios of the resulting ions; and wherein the mass/charge ratios provide a means for identification of the analyte particles.

The method can further compose restricting the hole openings by compressing spheroids into the entrances of said hole openings such that said openings are substantially closed.

BRIEF DESCRIPTION OF THE DRAWINGS

In order that the present invention is better understood, methods in accordance with the invention will now be described, by way of example only, with reference to the accompanying drawings in which:

FIG. 1A is schematic of a perforated material used in the method of the invention;

FIG. 1B is a sectional side view of the perforated material of FIG. 1A through a line x-x;

DETAILED DESCRIPTION OF THE INVENTION

Figure 2:
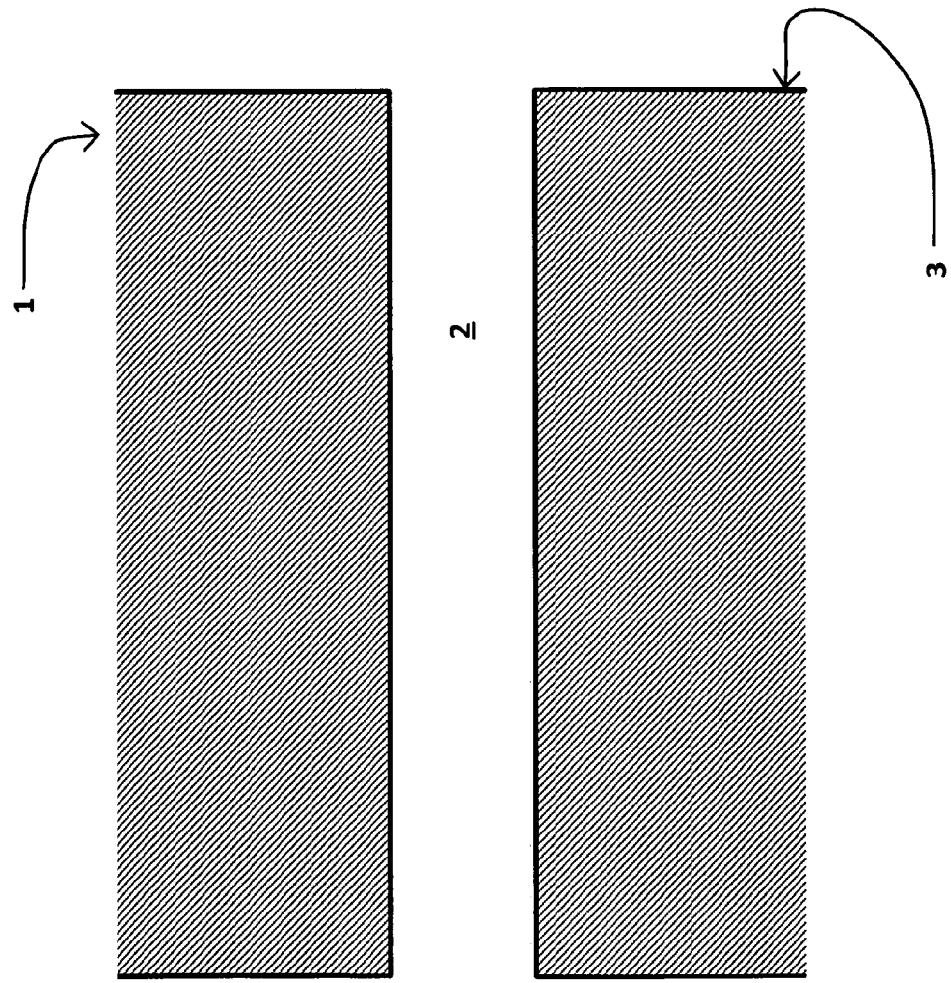
FIG. 2 is a magnified view of a single hole in the perforated material of FIG. 1.

Embodiments of the invention use a combination of existing technologies in a unique manner. These existing technologies comprise spheroids, magnetic fields, fluorescence, optics, filler technology, gel technology, chemistry, electrochemistry, chromatography, and Matrix-Assisted Laser Desorption Ionization (MALDI). These will be overviewed individually, and then methods in accordance with various embodiments of the invention will be described. Throughout this patent specification like reference numerals are used to denote like parts.

Spheroids

Spheroids are commercially available from a wide array of manufacturers, such as from; http://www.microspheres-nanospheres.com/

They have a high-precision diameters ranging from 50 nm up to 5000 nm, and can be made out various materials such as polystyrene or polystyrene/melamine copolymer. Additionally, they can be impregnated with magnetically active materials, and impregnated, with fluorescent materials. Furthermore, these particles can be manufactured with a derivatized surface, such as amine (NH2) or carboxyl (COOH), to which many ligands can be attached with well-established chemistry. They are commonly used for protein purification procedures, where a particular protein binds to the surface ligands, and then can be magnetically extracted from bulk solution.

Magnetic Fields

In a magnetic field gradient, a particle having a magnetic moment, such as a particle of ferrous oxide, will experience a force directed towards the convergence of the field, with a magnitude that is simply the product of the magnetic moment M and the intensity of the gradient nabla B.

A magnetic field gradient can be generated by a simple solenoid carrying an electric current. Typical solenoids have the point of maximum magnetic field gradient just outside the ends of the solenoid, always directed towards the center of the solenoid. A pair of opposing solenoids, each carrying an offset sine wave of electric current, can be used to generate a magnetic field gradient of arbitrary strength and polarity.

Fluorescence

Fluorescent materials absorb light of a short wavelength, and then release the energy as light, of a longer wavelength. There is a very large array of commercially available fluorescent dyes that find widespread use in the biotechnology field. One example is sodium fluoresceinate, which absorbs ultraviolet light and emits a green-yellow light. The neutral form, fluorescein, is non-fluorescent. In addition to fluorescent molecules, a newer type of material called Quantum Dots are also fluorescent. They are composed of particles of a semiconductor, such as cadmium sulphide (CdS) or cadmium telluride (CdTe). They are very small, of the order of a few nanometers in diameter, and are extremely fluorescent. The surface of the particles can be derivatized with various materials, such as amine (NH2) or carboxyl (COOH), to which many ligands can be attached with well-established chemistry. They are commonly used, for microscopy stains.

Optics

Fluorescence can be detected by exciting the fluorescence with, short wavelength light (such as ultraviolet light), and collecting the emitted longer wavelength light (such as visible light) with a photosensor. Examples of ultraviolet light sources are mercury-vapor bulbs and LED lasers. For near-ultraviolet, the 405 nm LED lasers commonly used for Blu-Ray disks are particularly convenient. The emitted fluorescence may be collected with optical lenses or light pipes and directed into a photosensor. Examples of photosensors are photomultiplier tubes and digital cameras. Photomultiplier tubes have high sensitivity and speed, and digital cameras can measure broad areas.

Filter Technology

A unique type of perforated material 10 comprising track-etched polycarbonate (TEPC) is commercially available for use in filtering, such as from Millipore Corp. or Whatman Corp.

TEPC comprises a sheet of polycarbonate material 12 having a smooth, glass-like surface, randomly punctured by very uniformly sized through holes 14. FIGS. 1A and 1B are schematic representations of such a perforated material 10. These holes 14 are available with sizes from 10 nm to 5000 nm diameter, and material thicknesses of 6000 to 1.1000 nm. They are produced by irradiating a sheet of proprietary polycarbonate material. The holes 14 are fairly parallel. The material exhibits a small degree of fluorescence, but is available dyed black. The material strongly absorbs ultraviolet light. The surface is specially treated with polyvinyl pyrrolidone to render it hydrophilic, removable by soaking in alcohol. Depending on the density of the holes, occasionally there is some overlap of the holes.

Gel Technology

Technically, gels are composed of an open cross-linked structure filled with liquid. However, the term "gel" as used herein is not restricted to its strict technical definition, but rather refers to generally any material that, is relevant to restricting diffusion of analytes. Common gels are made from gelatin, agarose, or acrylamide. The density of their open cross-linked structure is easily controlled by adjusting the concentrations of the materials used to form the gel. Some gels, such as made from gelatin or agarose, have a melting point, below which the gel structure forms. Other gels, such as made from, acrylamide, can be formed by chemically induced polymerization or ultraviolet induced polymerization. These gels are heavily used in the biotechnology field for separating complex mixtures of proteins, in a popular technique called gel electrophoresis. In this technique, a concentrated aliquot of protein mixture is injected into the middle of a sheet of gel, and then an electric field is applied to the gel at each end of the sheet. The open cross-linked structure of the gel is essentially a collection, of pores through which the protein molecules can pass. Since protein molecules typically have a characteristic charge and diameter, they will tend to migrate in the electric field at particular rates through the pores of the gel. Since each protein type has a unique charge and diameter, the protein mixture will physically separate into its components.

If the cross-linked structure of the gel is sufficiently dense, only small molecules will be able to pass through the pores, and large molecules will not be able to migrate at all from the injection point. The molecular size above which migration does not occur is commonly referred to as the Exclusion Limit of the gel. For polyacrylamide, the Exclusion Limit can be made smaller than, most typical proteins.

Chemistry

Acrylamide copolymerization is a well-known reaction, commonly used to generate gels used for gel electrophoresis. It is prepared by mixing acrylamide monomer with a cross-linking agent such as N,N'-methylenebisacrylamide (bis), and catalyzing with free radicals such as from persulfate anion, and an initiator such as the tertiary aliphatic amine N,N,N',N'-tetramethylethylenediamine (TEMED). It can also be polymerized with riboflavin and long-wavelength ultraviolet light. Additional reagents such as urea may be used to reduce the porosity of the gel. Additionally, other polymers may be included, such as polyacrylate, to aid in lamination, chemistry.

Carboxylate derivatization and amine derivatization are processes by which a substrate, such as a molecule or surface, is caused to chemically react with aqueous reagents, resulting in attachment of carboxylate or amine moieties to the substrate. For example, a polycarbonate surface may be derivatized by treatment with appropriate organic azides to yield primary amine moieties, or its polyvinyl pyrrolidone surface opened with strong base to form carboxylate moieties. Generally, these moieties are substantially exposed to the bulk solution, where they can then, be used for a variety of purposes. The chemistry used for the attachment is highly dependent on the chemistry of the substrate.

Peptide bond synthesis is a well-known reaction, commonly used for peptide synthesis. A carboxylate moiety is treated with 1-ethyl-3-(3-dimethylaminopropyl)carbodiimide (EDC) to generate an unstable reactive o-acylisourea ester. This ester can react with a primary amine moiety to form, a stable amide bond. However, since this ester is so reactive, it will also react with the solvent (water) to regenerate the carboxyl moiety. This reduces the efficiency of the reaction. Improvement can be made by reacting the ester with N-hydroxysulfosuccinimide (Sulfo-NHS), which forms a semi-stable amine-reactive NHS ester. This latter ester will not react with water, but only with a primary amine moiety to form a stable amide bond.

Electrochemistry

If two electrodes are placed in an aqueous solution, and an electric potential is applied between, the electrodes, then an electric field will be generated in the aqueous solution. Water naturally dissociates slightly into $H3O+$ and $OH-$ ions. Since these dissociation, products carry a charge, they will migrate, to the electrode surfaces, where the metal will provide or extract an electron, completing a circuit of electric current. Ionic salts added to the water, such as sodium, chloride, introduce a much higher concentration of ions, allowing a significantly greater flow of electric current. If a variety of ionic salts are present in the aqueous solution (each having chemistry that defines the ease of the electron transfer process), then scanning the electrode potential, while monitoring the electric current provides a characterization of the ionic salts in aqueous solution. Often, it is useful in the field of electrochemistry to add an ionic salt with a very difficult, electron transfer process; such ionic salts are commonly referred to as "supporting electrolyte". The structure of the electric field at the surface of the metal electrodes is very complex, as the various ions form, layers near the metal surface.

Chromotography

Chromatography is the physical separation of components in fluid media, followed by an appropriate detection method. Typically, a concentrated plug of a complex mixture is swept by a carrier stream (the "mobile phase") through a narrow tube (the "column") that has been packed with particles (the "stationary phase") coated with a material that weakly binds to the components of the mixture. As the components flow past the stationary phase, some components bind more strongly than others, and will elute out of the column slower. Hence, the eluant from the column will first consist of nonbinding components, and then a series of components of ever-increasing binding strength. A detector that monitors some universal characteristic of the components, such as ultraviolet absorption, indicates the presence of material as it elutes out of the column. The eluant can be diverted with valves to collect each component.

In the biotechnology field, gel electrophoresis has been used widely for the separation and detection of complex mixtures of proteins. However, the technique is somewhat unwieldy and requires fairly large volumes of protein. Recently, this technique is starting to be replaced, by "Multidimensional Protein Identification Technology", otherwise known as MudPIT. This technique uses a combination of columns having different properties, along with a set of fluidic valves, to attain protein separation that is superior to gel electrophoresis. The use of Capillary Zone Electrophoresis can also reduce the volume of protein used.

Matrix-Assisted Laser Desorption Ionization (MALDI)

In conventional use, MALDI involves spotting a microscopic quantity of biological sample onto a glass or silicon wafer, and mixing it with a vaporizable compound. The wafer is dried, and then place in a mass spectrometer chamber. A focused, laser poise vaporizes each sample, and the resulting vapor ionized and accelerated through the main chamber of a mass spectrometer. During vaporization, the biological samples are severely fragmented, and the fragmentation pattern extracted from, the mass spectrometry data. This procedure is widely used in industry, with equipment manufactured by Sequenom and other manufacturers.

First Embodiment Summary

A specially-constructed, layered material forms a set of reservoirs that are loaded with a variety of spatially-separated analyte particles, and said layered material scanned with an electrochemical probe. This yields a map of the characteristics of the various analyte particles, which can provide useful information about biological samples.

Method in Accordance with a First Embodiment of the Invention

In a method in accordance with a first embodiment of the invention, a perforated material, such as a TEPC filter, has holes with restricted openings. Homogeneous or heterogeneous populations of analyte particles within a controlled matrix are loaded into the TEPC filter holes, and electrical current is used to measure the diffusion outwards, which is a measure of presence, structural changes, and any binding interactions involving the analyte particles.

The method of the invention will now be described by way of reference to FIGS. 1 to 43.

Referring to FIGS. 1A, 1B, and 2, the TEPC filter 1 has a random distribution of uniformly-sized holes. FIG. 1A shows the top view, and FIG. 1B is a cross sectional view. The TEPC filter 1 may have an outer surface chemically derivatized with carboxylate moieties 3. Other materials having similar characteristics may be substituted.

Figure 3:
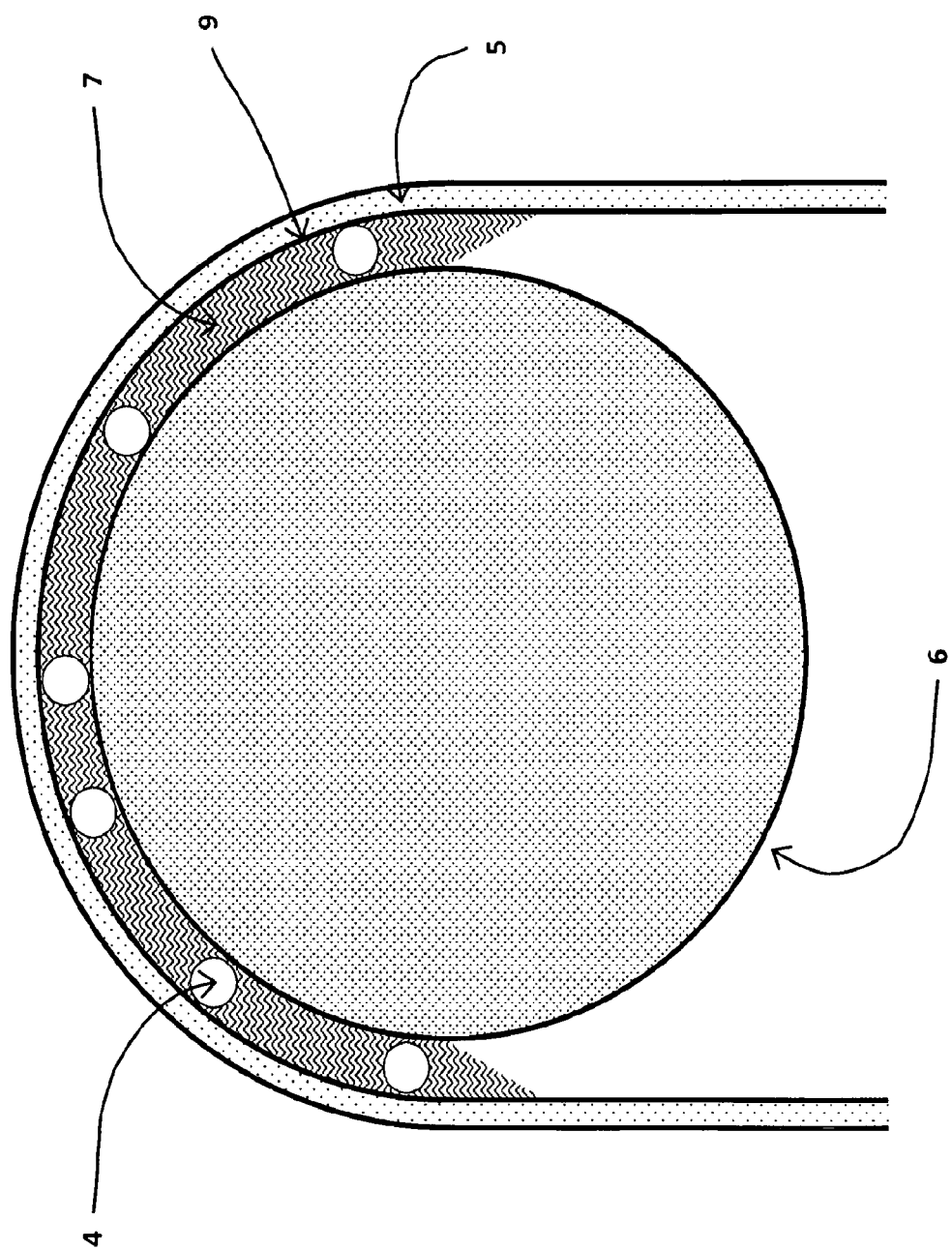
FIG. 3 is an illustration of the manufacture of a bilayer material of controlled thickness.
Figure 4:
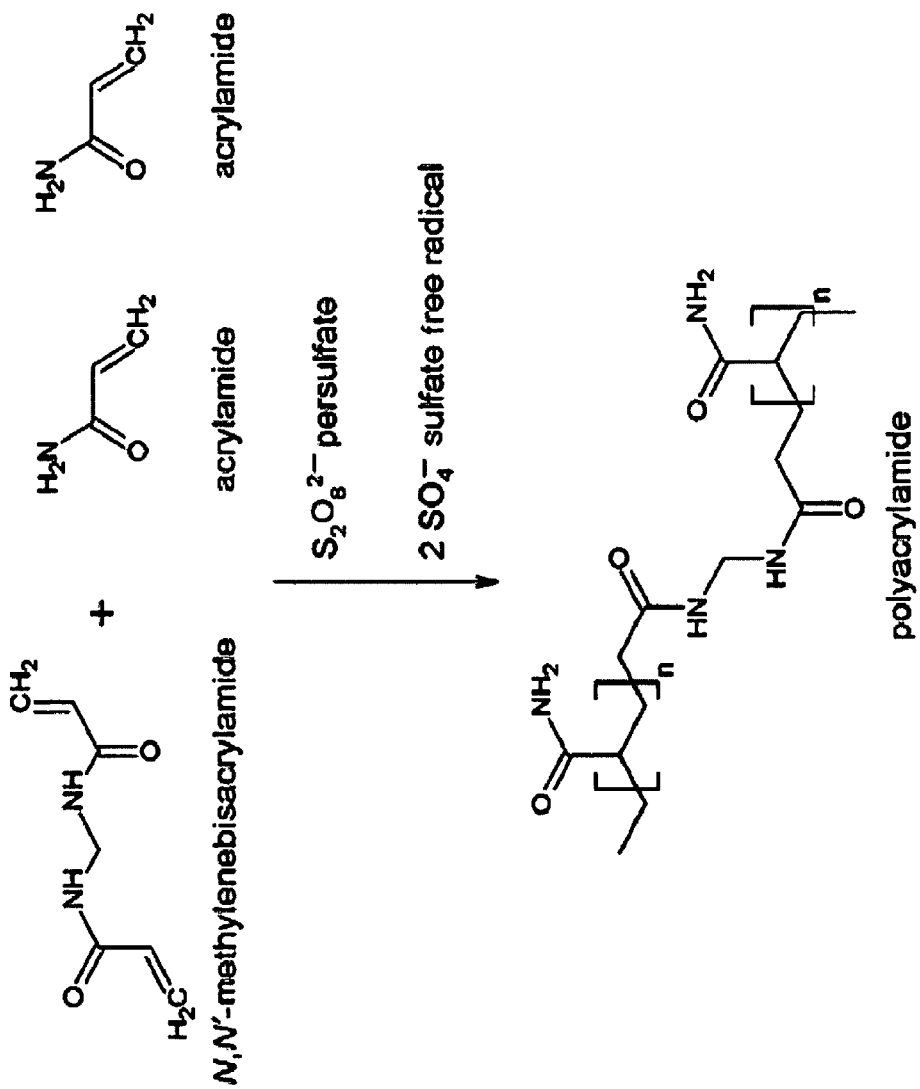
FIG. 4 is an illustration of the known chemistry for forming polyacrylamide gel.
Figure 5:
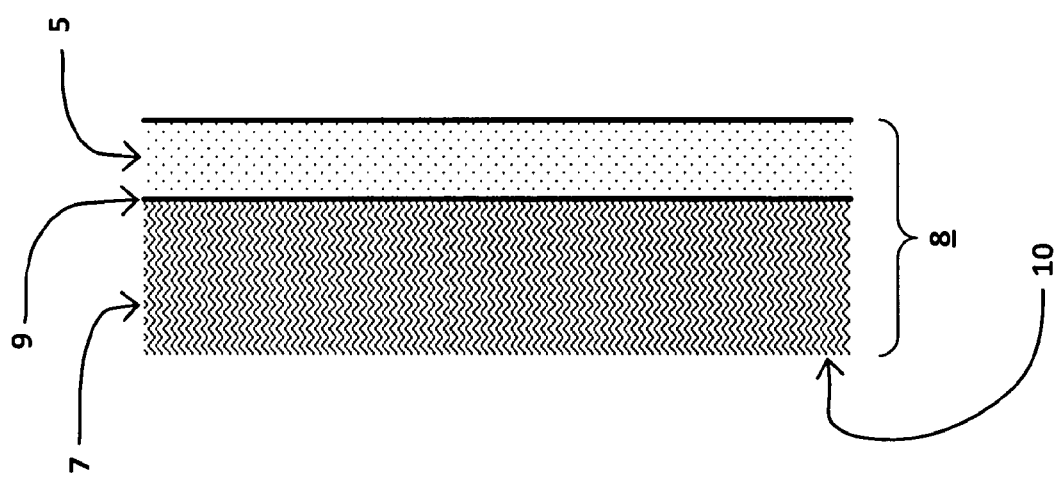
FIG. 5 is a magnified view of the bilayer material from FIG. 3.

Referring to FIGS. 3, 4, and 5, a bilayer material may be formed by the following process. Firstly, a dilute suspension of spheroids 4 of uniform size is formed in a matrix of a gel precursor (such as acrylamide or melted agarose). The suspension, is then applied to a thin plastic sheet 5 and wrapped around a smooth cylinder 6 that has a hydrophobic surface. The gel 7 is formed by chemical, thermal, or light polymerization. An example of chemical polymerization is illustrated in FIG. 4. The spacer particles 4 enforce a uniform, known thickness to the gel 7. After polymerization, the thin plastic sheet 5 is peeled off of the smooth cylinder 6, creating a bilayer material 8 consisting of a gel 7 layer and a plastic 5 layer. A magnified view of this bilayer material is shown in FIG. 5; the spheroids 4 are not shown in this magnified view because they are sufficiently dilute. The chemistry of the bilayer material 8 interface 9 is chosen such that the thin plastic sheet 5 layer may be easily removed in the future by physical or chemical means. The outer surface of the gel 7 may be chemically derivatized with, amino moieties 10, but these are indigenous to polyacrylamide.

Alternatively to said bilayer material, a gel precursor may be sandwiched between two hydrophobic smooth plates, and allowed to polymerize and dry. This forms a robust dried gel film that can be easily handled, and then re-hydrated when needed.

Alternatively to said bilayer material, a dialysis membrane may be used, which may be purchased commercially from many vendors, such as Millipore or Whatman.

Figure 6:
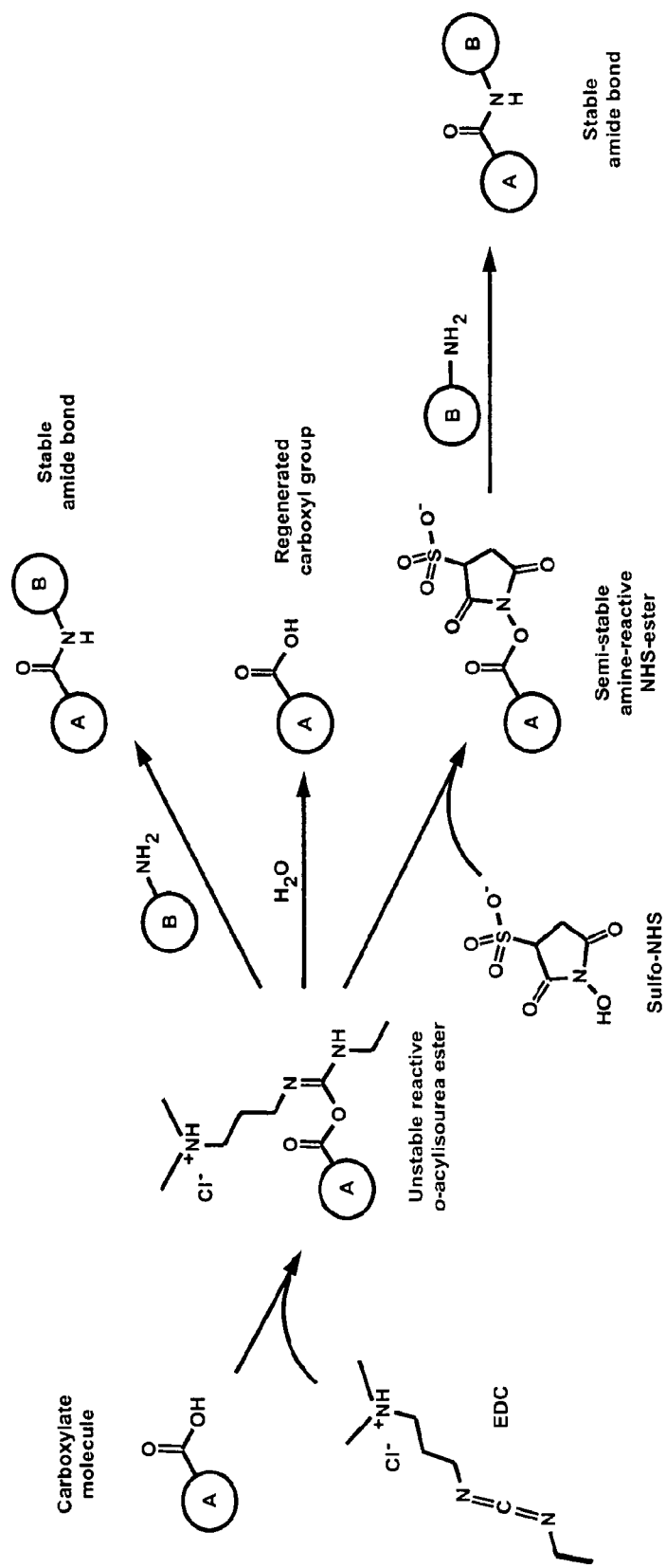
FIG. 6 is an illustration of the known chemistry of peptide bond synthesis.
Figure 7:
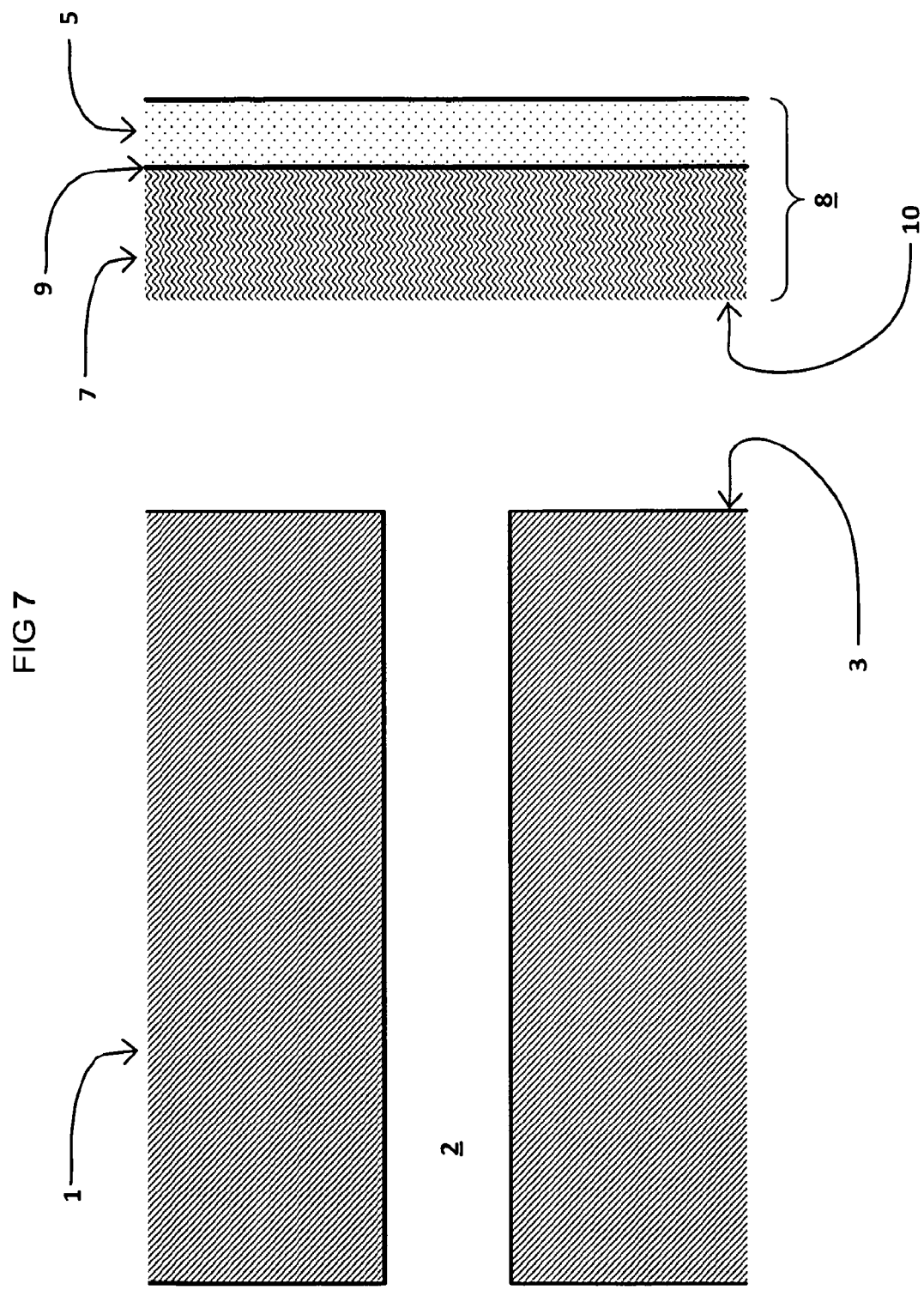
FIG. 7 is a schematic of both the perforated material of FIG. 1 and the bilayer material of FIG. 3, in close proximity.
Figure 8:
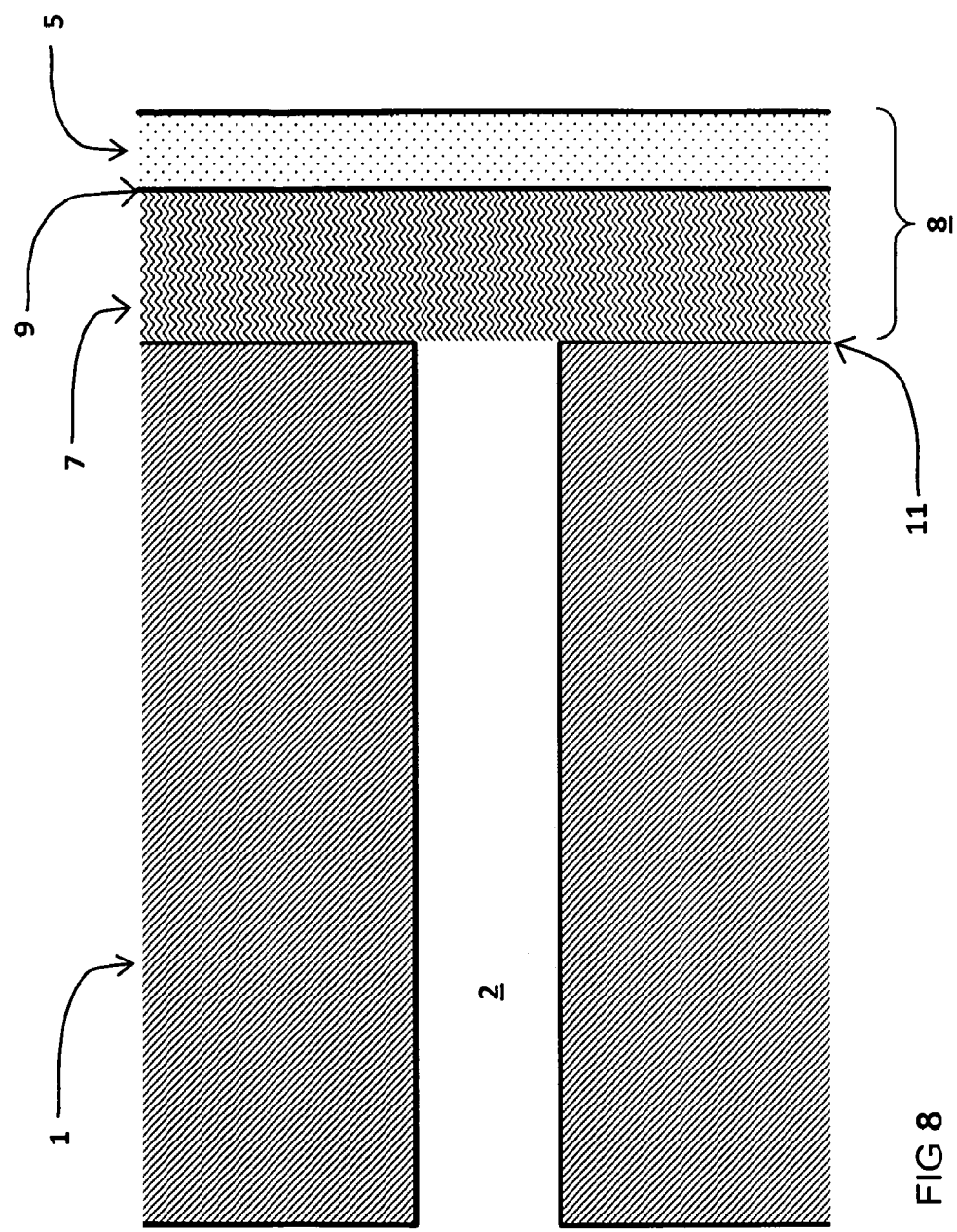
FIG. 8 is a schematic of a structure resulting from the perforated material of FIG. 1 and the bilayer material of FIG. 3 being bound together by peptide bonds.

Referring to FIGS. 6, 7, and 8, the bilayer material 8 may be chemically bonded to the TEPC filter 1. An example of a chemical bonding, mechanism is shown in FIG. 6, where carboxylate moieties and amino moieties chemically bind to form a peptide bond 11. Other chemistries may be substituted. FIG. 7 shows the TEPC filter 1 and the bilayer material 8 in close proximity, with the carboxylate derivatized surface 3 and the amino derivatized surface 10 facing each other. FIG. 8 shows the TEPC filter 1 and the bilayer material 8 chemically bonded together with the peptide bond 11.

Figure 9:
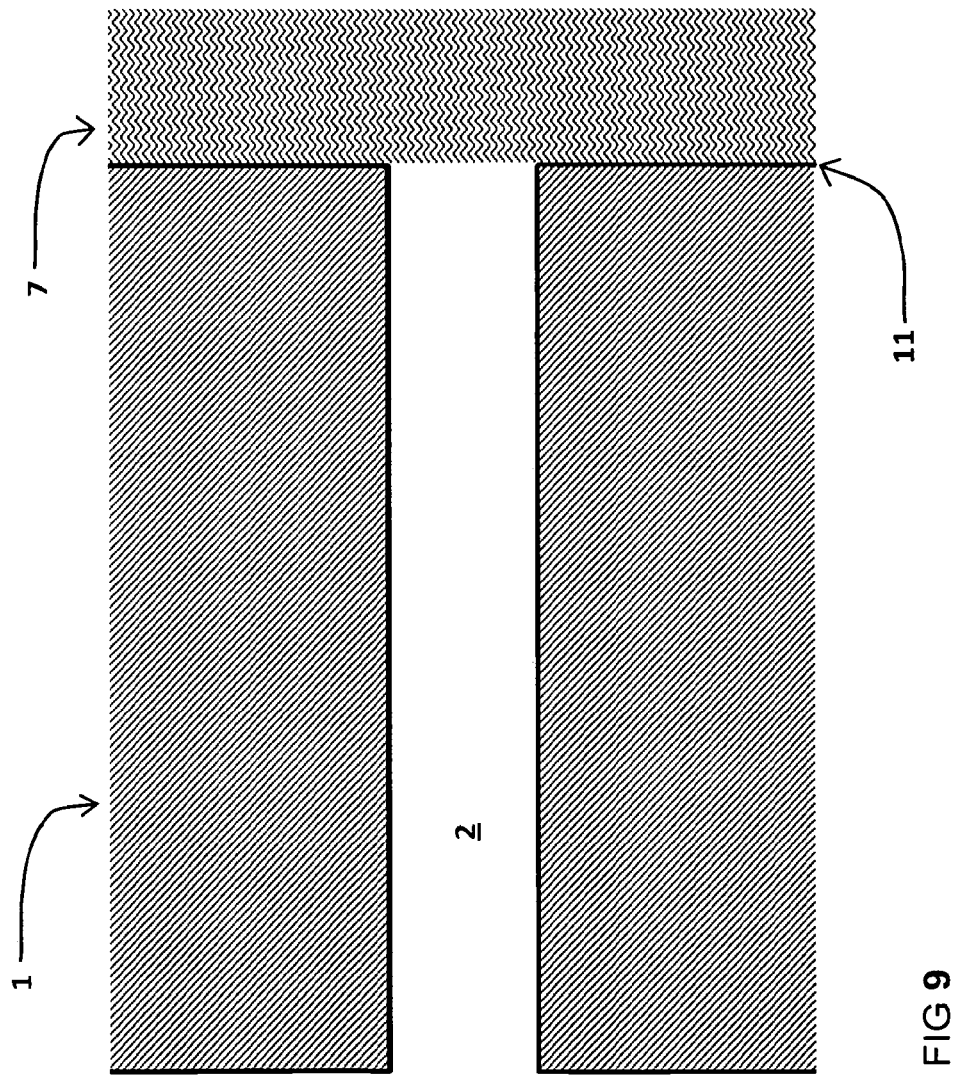
FIG. 9 is a schematic of the structure of FIG. 8, with the outer layer of the bilayer removed, leaving a layer of gel adhered, to the perforated material.

Referring to FIGS. 8 and 9, the thin plastic sheet 5 may be removed by physical or chemical means, leaving only the gel 7 layer adhered, to the TEPC filter 1.

Alternatively to said chemical bonding, the gel 7 layer and the TEPC filter 1 may simply be compressed together by physical force without chemical bonds, such as by wrapping around a cylinder and tensioning the outer TEPC filter 1 layer.

Alternatively to said chemical bonding, the TEPC filter 1 may be placed on a surface of a conductive fluid that is immiscible with, the fluid comprising the analyte particle matrix.

There are a number of variations that are possible to the schematic shown in FIG. 9, and the examples of these are shown in FIGS. 10, 11, 12, 13, 14, 15, and 16. Although the remainder of this Method will focus on the simple case of FIG. 9, it will be appreciated that these variations are also applicable.

Figure 10:
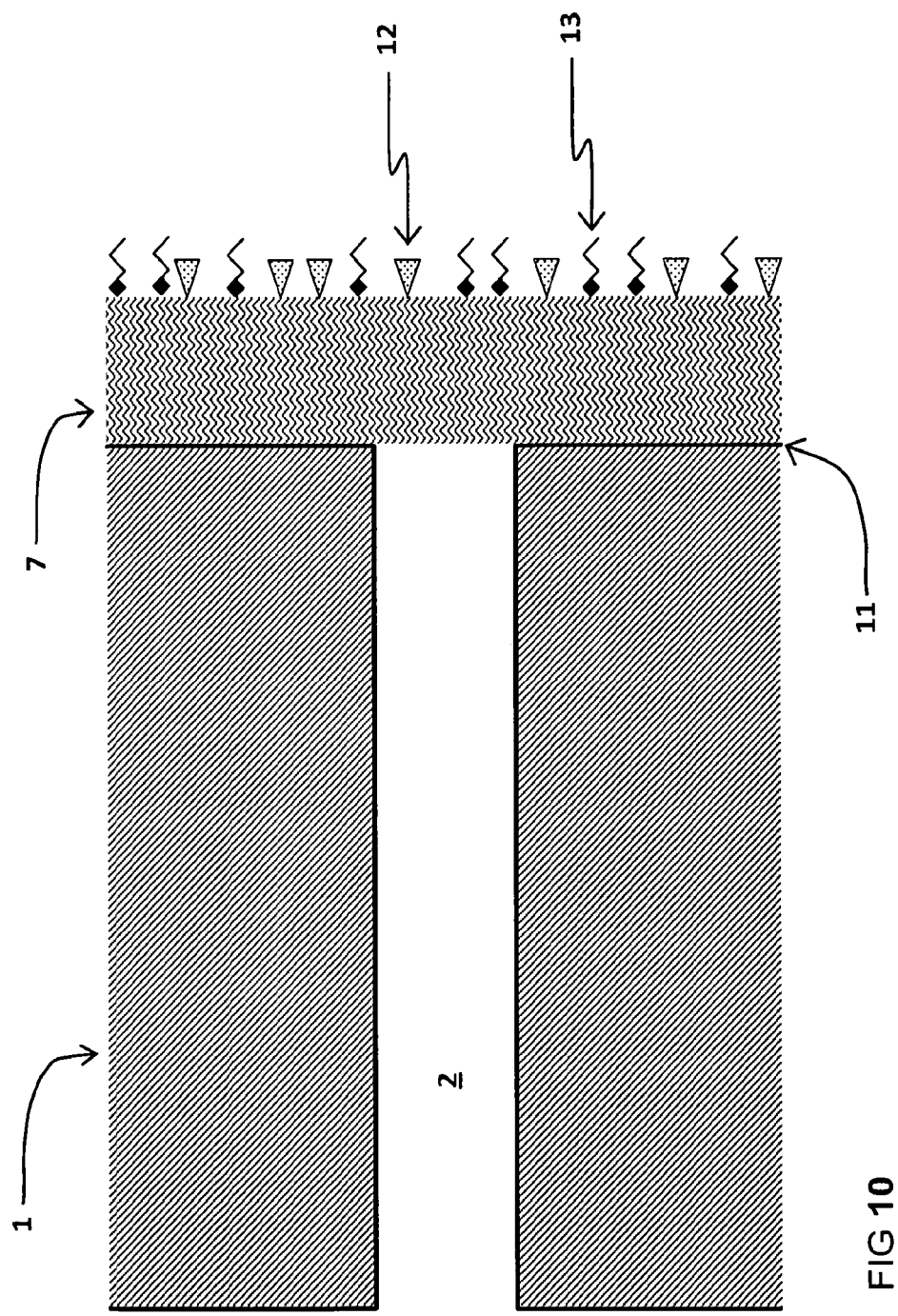
FIG. 10 is a schematic of a variation in FIG. 9, having fluorophores or surfactants chemically bound to the outer surface of the gel.

Referring to FIG. 10, the outer surface of the gel 7 may be chemically derivatized with fluorophores 12, surfactants 13, other materials, or any combination of materials. Likewise, the inner surface of the gel 7 (facing the hole 2) or the inner surface of the hole 2 may also be chemically derivatized.

Figure 11:
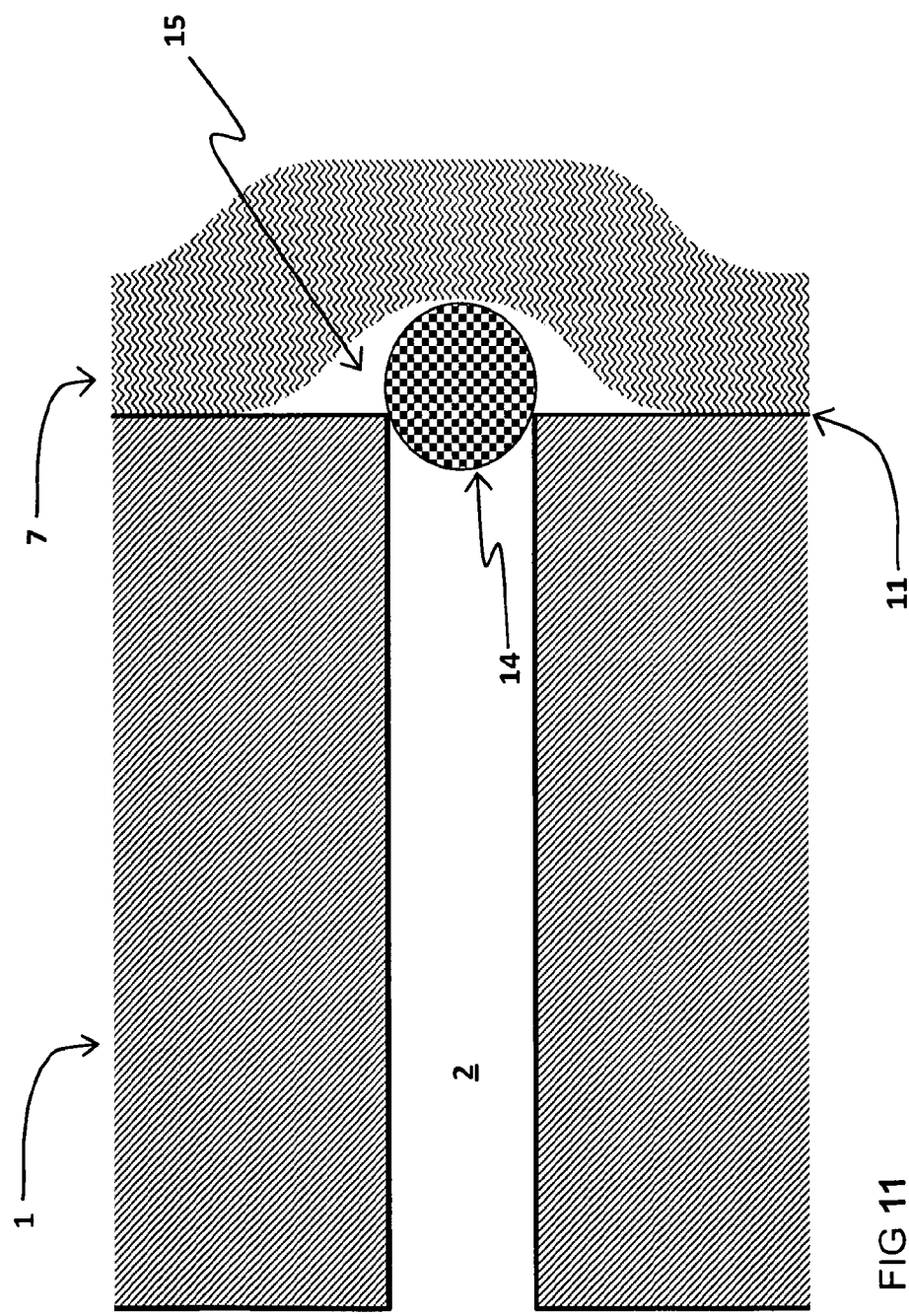
FIG. 11 is a schematic of a variation of FIG. 9, having a spheroid clogging one end of a hole in the perforated material before assembly of the structure, with a small gap.
Figure 12:
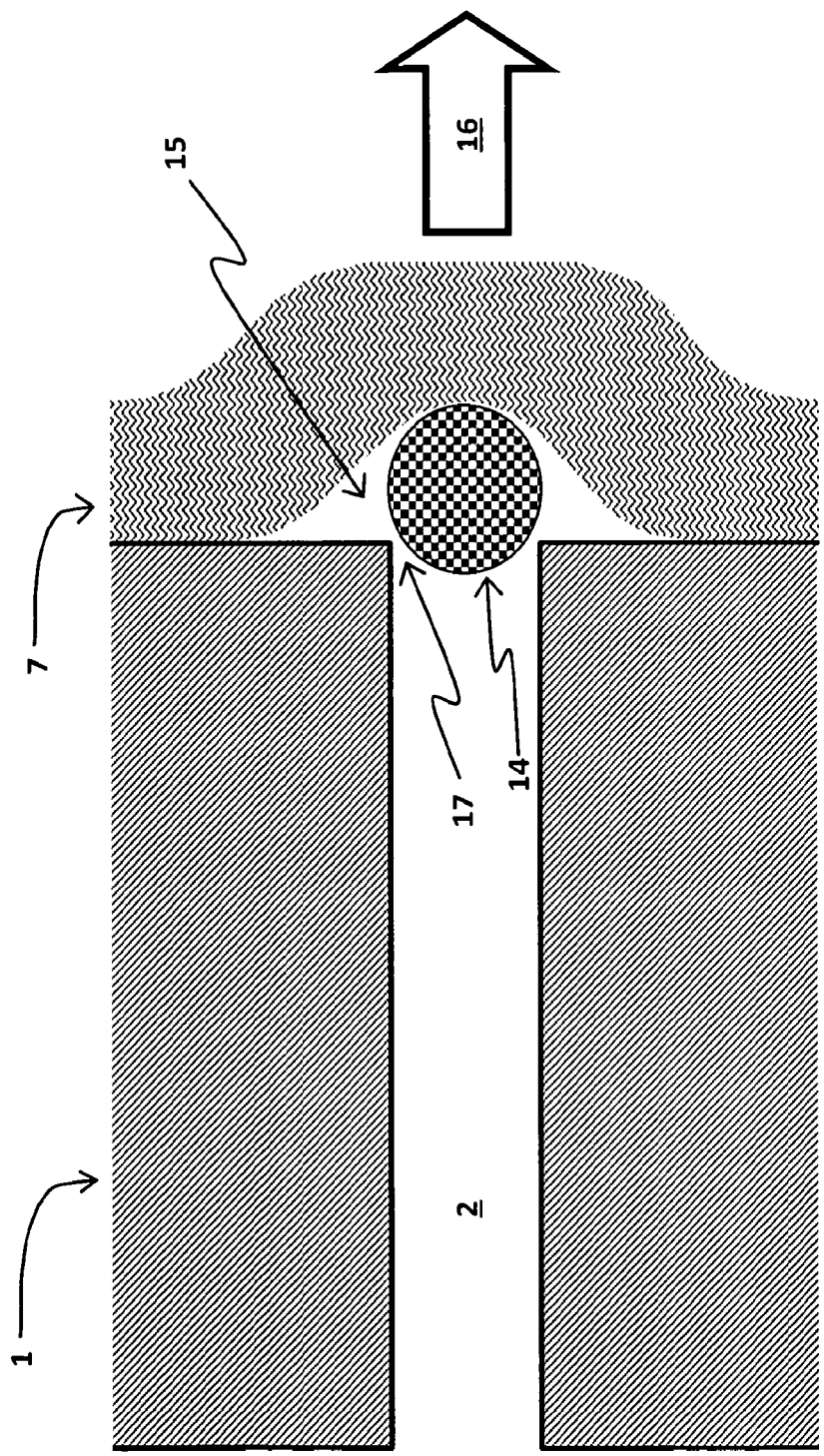
FIG. 12 is a schematic of the unclogging effect of a force, such as from a magnetic field gradient, by moving the position of the spheroid of FIG. 11.
Figure 13:
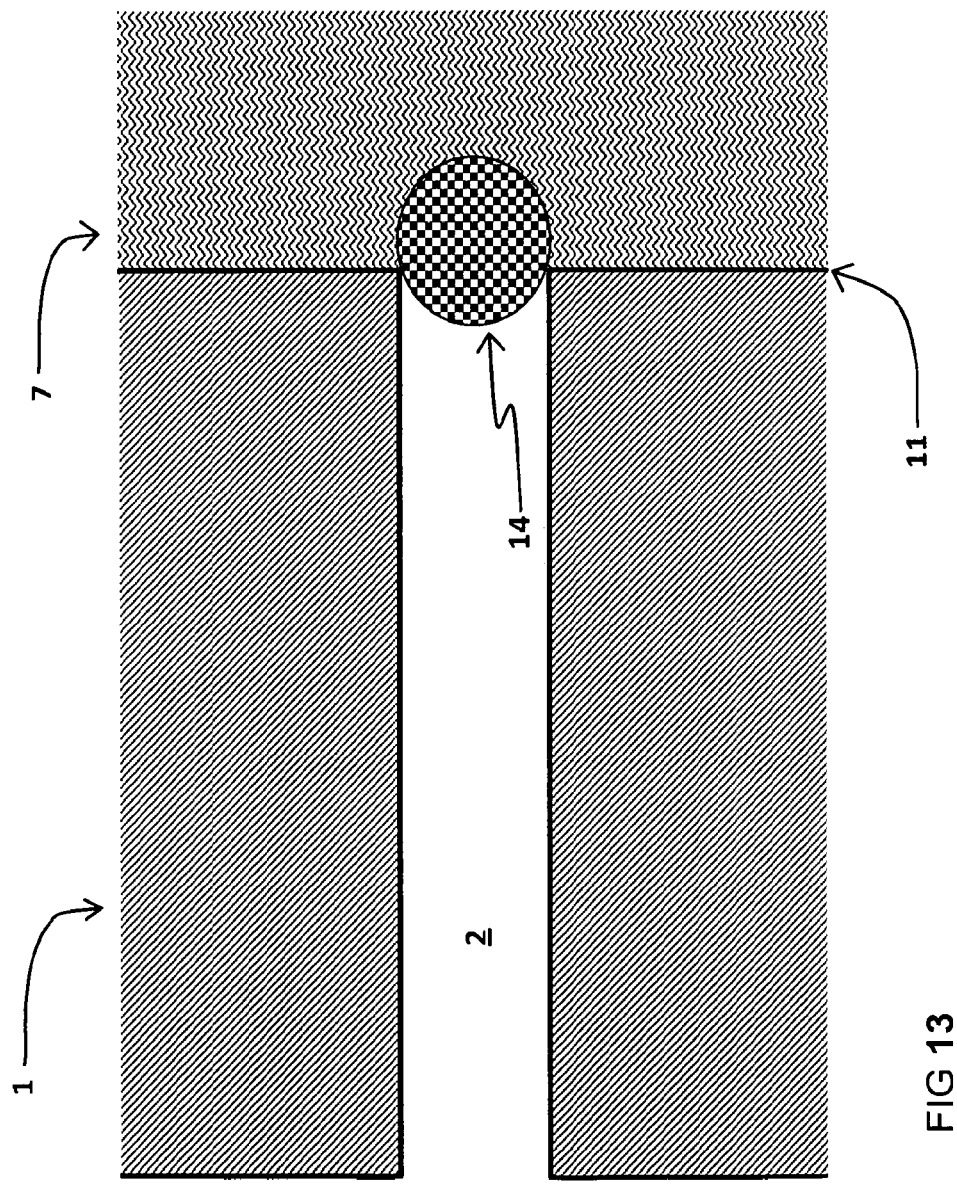
FIG. 13 is a schematic of a variation of FIG. 9, having a spheroid clogging one end of a hole in the perforated material before assembly of the structure, with no gap.

Referring to FIGS. 11, 12, and 13, a spheroid 14 may be lodged in the opening of the hole 2, prior to formation of the peptide bond 11. This spheroid 14 would have a diameter slightly larger than the diameter of the hole 2. The gel 7 layer would be dimpled by the presence of the spheroid 14, creating an empty volume 15 around the spheroid 14. A force 16, such as from a magnetic field gradient, electric field, gravitational field, or hydrodynamic flow, may be used to lift the spheroid 14 from its seating in the opening of hole 2, creating a small gap 17 between the surface of the spheroid 14 and the opening of the hole 2. The empty volume 15 may be removed by brief heating of the spheroid 14 to melt the surrounding gel 7, or by saturation with gel precursors followed by chemical polymerization. The resulting structure is shown in FIG. 13

Figure 14:
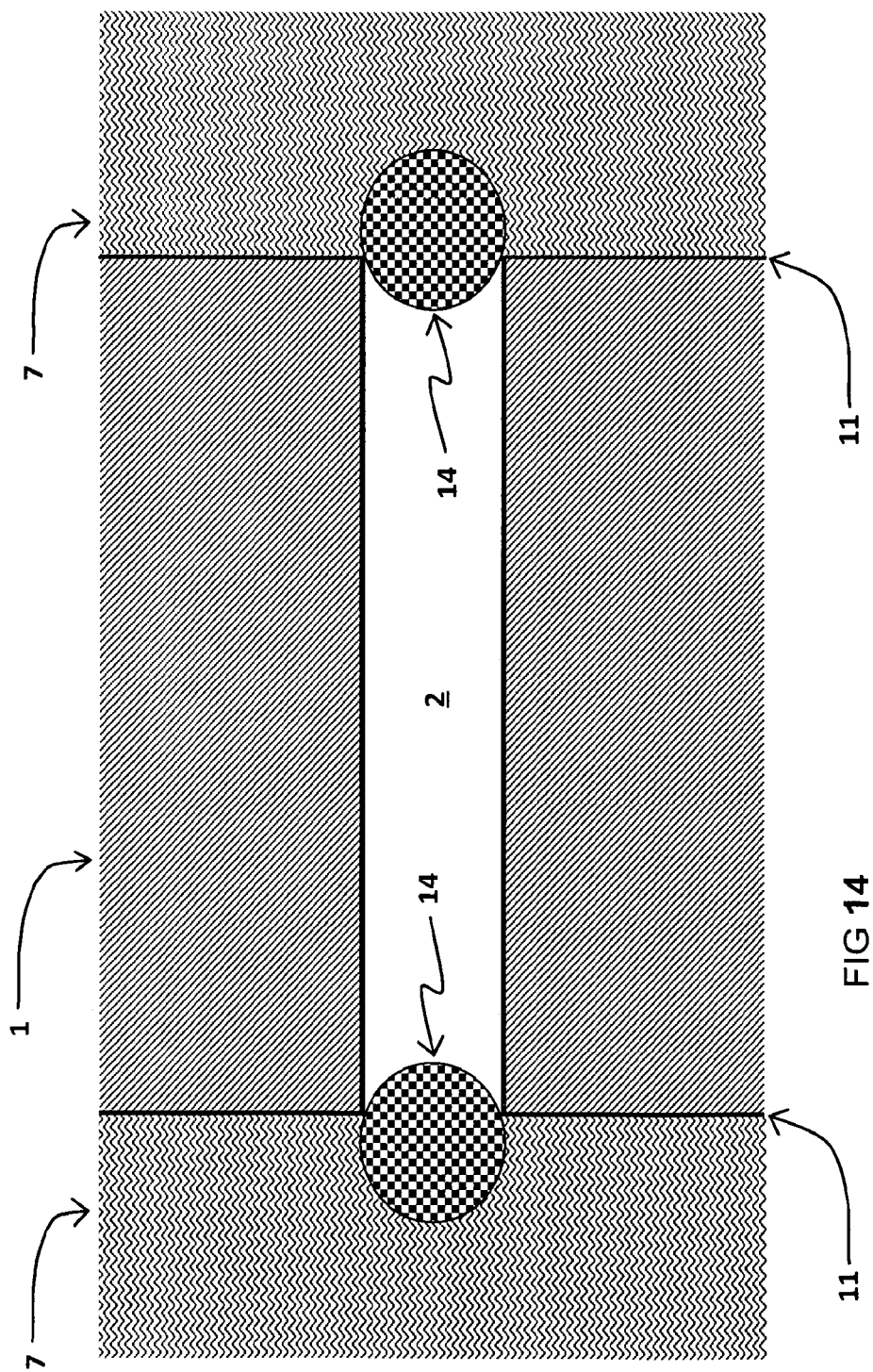
FIG. 14 is a schematic of a variation of FIG. 9, having spheroids clogging both ends of a hole in the perforated material.
Figure 15:
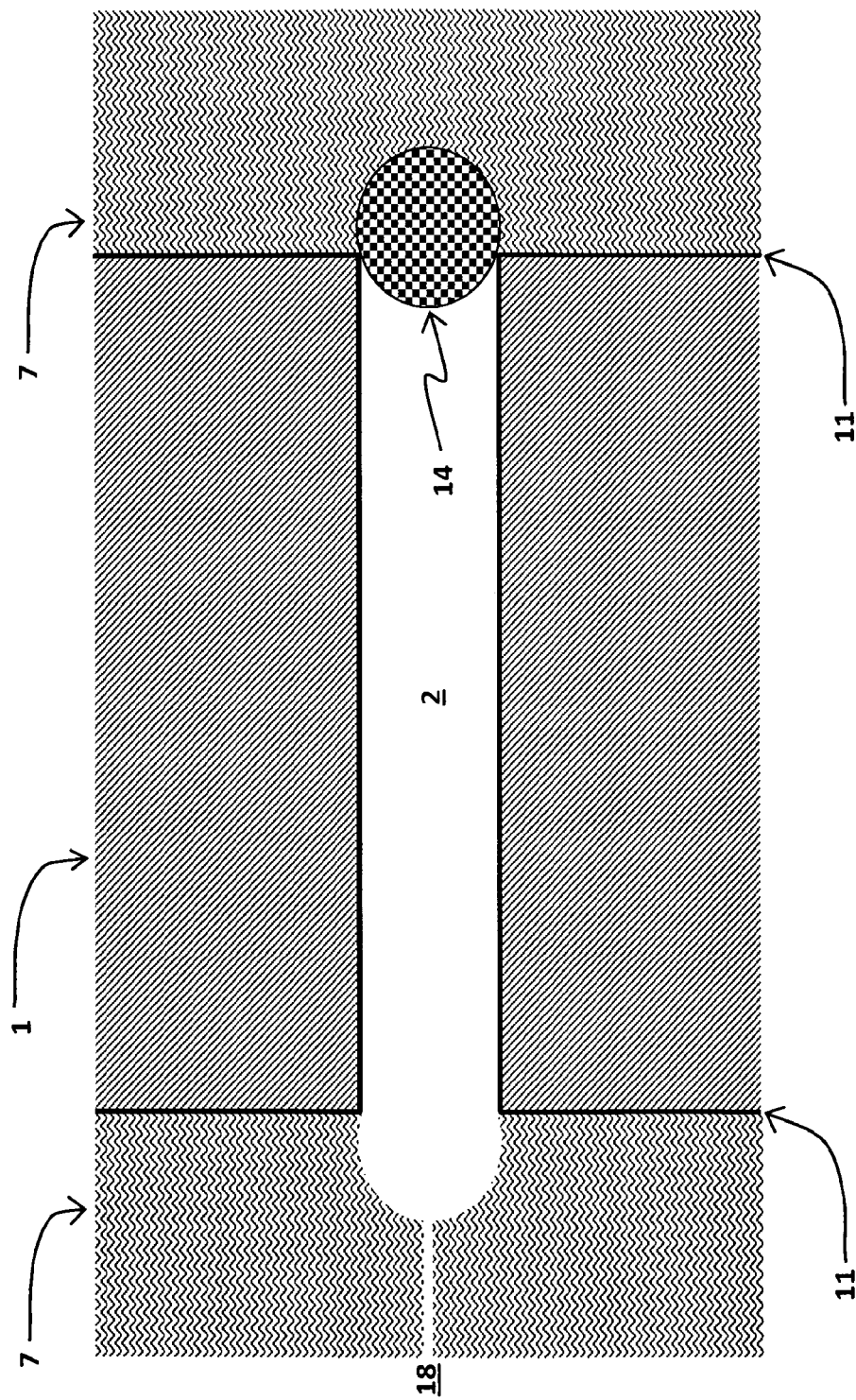
FIG. 15 is a schematic of a tear in the gel resulting from removal of one of the spheroids of FIG. 14.

Referring to FIGS. 14 and 15, both ends of the hole 2 may be capped by spheroids 14. If the gel 7 is sufficiently pliable, then one of the spheroids 14 may be removed by a force, such as from a magnetic field gradient. This would leave a small tear 18 in the gel 7. This particular configuration would be especially useful for retention of materials within the hole 2 without an active retention mechanism.

Figure 16:
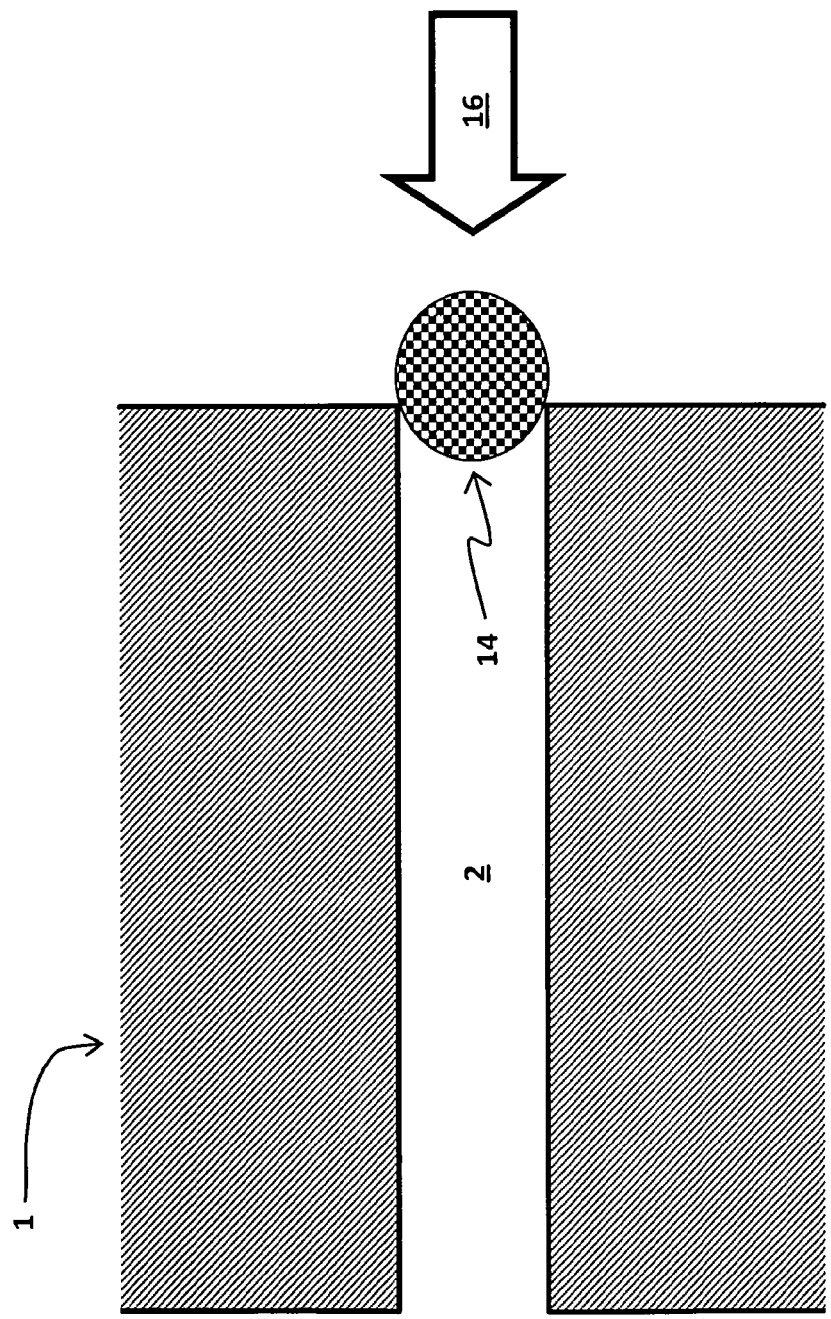
FIG. 16 is a schematic of a variation of FIG. 9, having a spheroid clogging one end of a hole in the perforated material, with no gel, held in place by a force, such as from a magnetic field gradient.

Referring to FIG. 16, the gel may be not used, and the spheroid 14 held in place with a force, such as from a magnetic field gradient 16.

Figure 17:
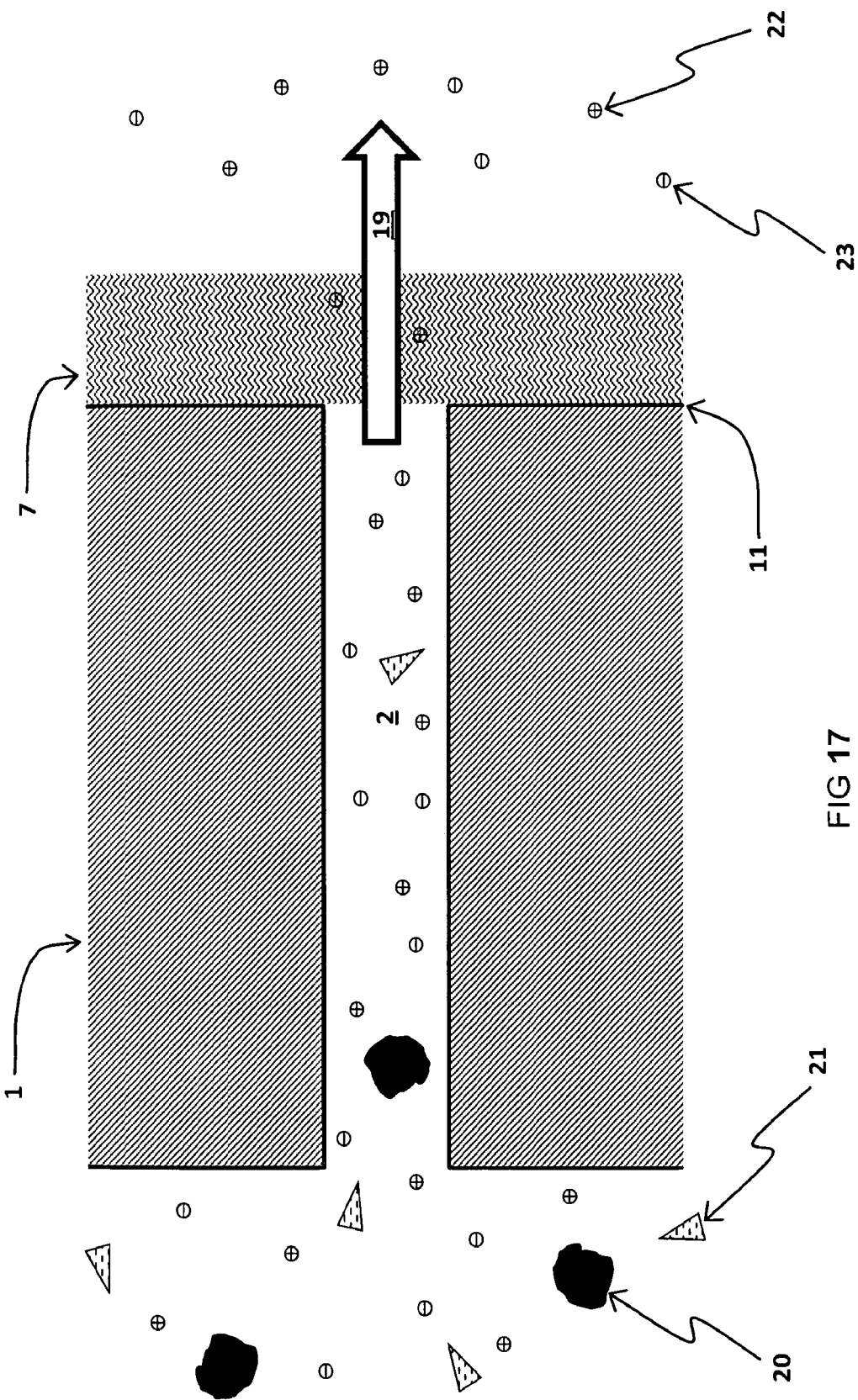
FIG. 17 is a schematic of fluid flow through the hole of the structure of FIG. 9.
Figure 18:
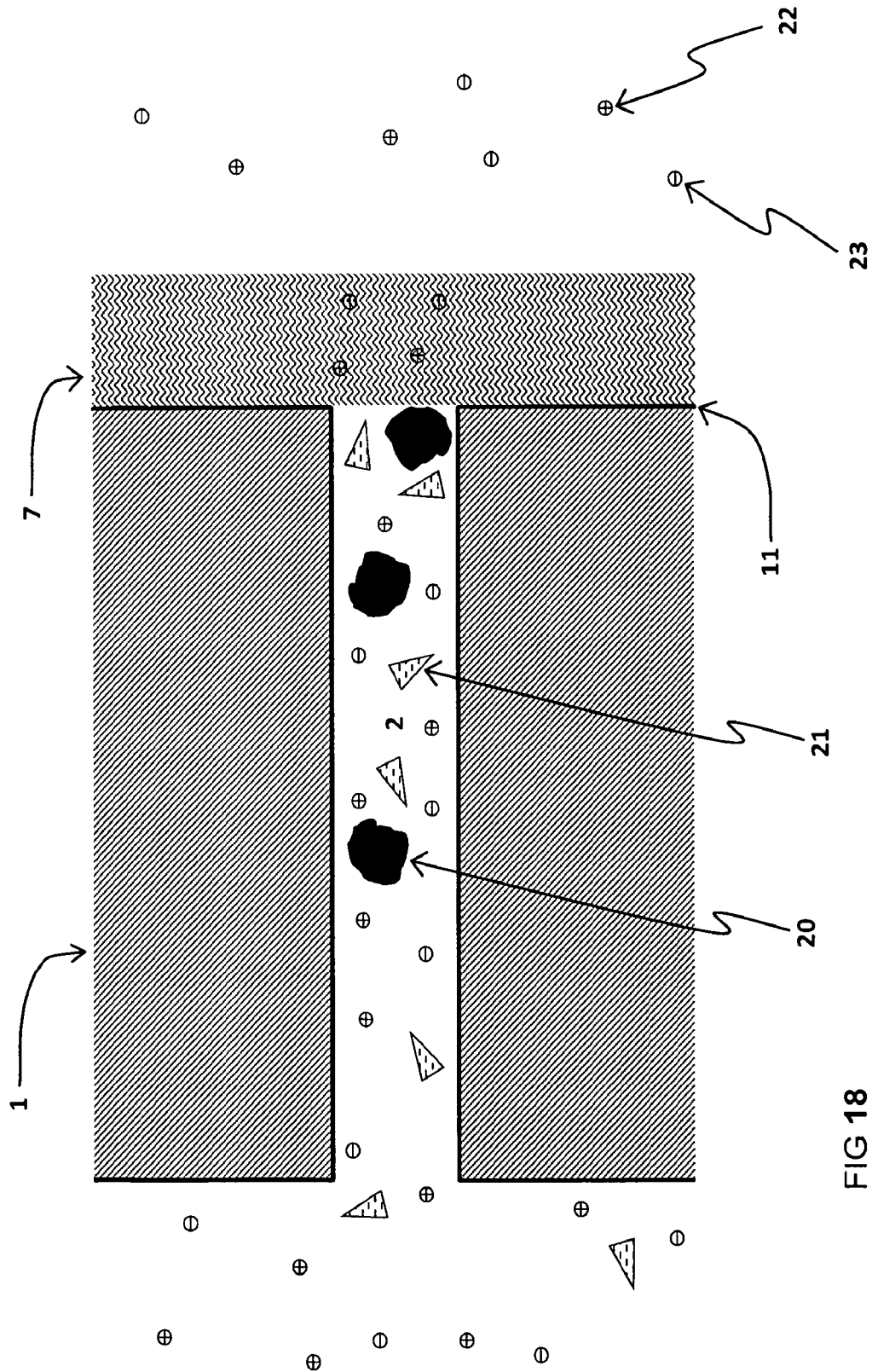
FIG. 18 is a schematic of the accumulation of analyte particles in the hole of the structure of FIG. 9.

Focusing on the simple example of FIG. 9, this structure may be used to collect and concentrate analyte particles within the hole 2. FIG. 17 is a schematic of fluid flow 19 passing from the open end of the hole 2, through the hole 2, and then through the gel 7. Analyte particles that are suspended within the fluid flow 19 become filtered by the gel 7, if the gel 7 has a sufficiently tight cross-linked structure to prevent passage. Examples of such, analyte particles are proteins 20, nucleic acids, viruses, protoplasmic structures. Quantum Dots, large fluorophores 21, large electrolyte cations, large electrolyte anions, and large redox reagents. The permeability of the gel 7 may be reduced by inclusion of particles within the gel 7 during formation. Examples of particles that are able to pass through the gel 7 are water molecules, small electrolyte cations 22, small electrolyte anions 23, and small redox reagents. FIG. 18 is a schematic of the net result of accumulated analyte particles within the hole 2.

Once there are accumulated analyte particles in the hole 2, the fluid flow 19 can be stopped. At this point, the accumulated analyte particles will begin to diffuse outward, eventually emptying the hole 2. The fluid flow 19 may then be reinstated, and the accumulation/diffusion cycle repeated. A gel that weakly limits diffusion may be placed at the hole 2 outlet, to improve cyclability. A gel that weakly limits diffusion may be placed within the hole, to extend the diffusion times.

During diffusion, the analyte particles in the hole 2 would have movement pathways that can intersect with ionic particles. Since the particles can not pass through each other, they go around each other, slowing down the movement pathways of the ionic particles. This slowing down is dependent on the presence of analyte particles and their binding processes, and thereby forms the basis of this Method.

During diffusion, the analyte particles in the hole 2 may be driven axially with a migration force (e.g. force resulting from an electric field) in addition to diffusion.

This process is also applicable to the accumulation part of the cycle, but analysis is complicated by the addition of fluid flow 19 forces.

During the diffusion or accumulation parts of the cycle, the fluid flow 19 may be given a high-frequency axial, oscillation, for the purpose of modifying particle movement. For example, the spheroid 14 of FIG. 15 may have a magnetic moment and be magnetically oscillated to pump analyte particles through the tear 18. As another example, the outer (or inner) surface of the gel 7 in FIG. 9 may be subjected to pressure pulsations, causing the analyte particles within the hole 2 to likewise oscillate.

There are numerous mechanisms by which particles in the hole 2 may by driven, axially with a force in addition to diffusion. An example of one of these mechanisms is illustrated in FIG. 22.

Figure 22:
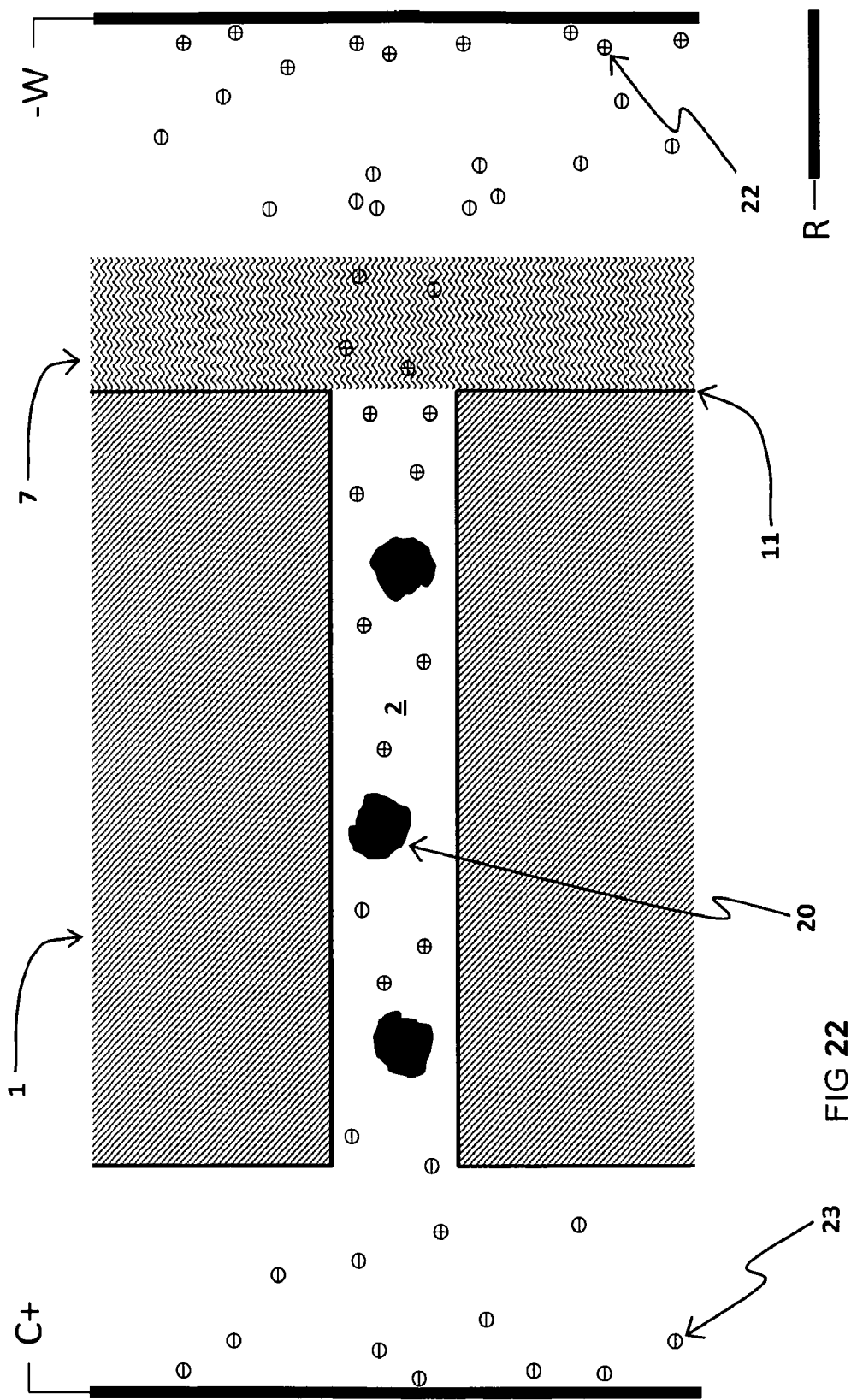
FIG. 22 is a schematic of electrolyte migration induced by an electric field E.

Referring to FIG. 22, electrolytes or redox reagents that are able to traverse the gel 7 are moved through the gel 7 by an electric field generated by Working (−W), Counter (C+), and Reference (R) electrodes.

In each of these examples for mechanisms by which particles in the hole 2 may by driven axially with a force in addition to diffusion, the movement pathways themselves may be slowed down by several different mechanisms. Examples of some of these mechanisms are illustrated in FIGS. 27 and 28.

Figure 27:
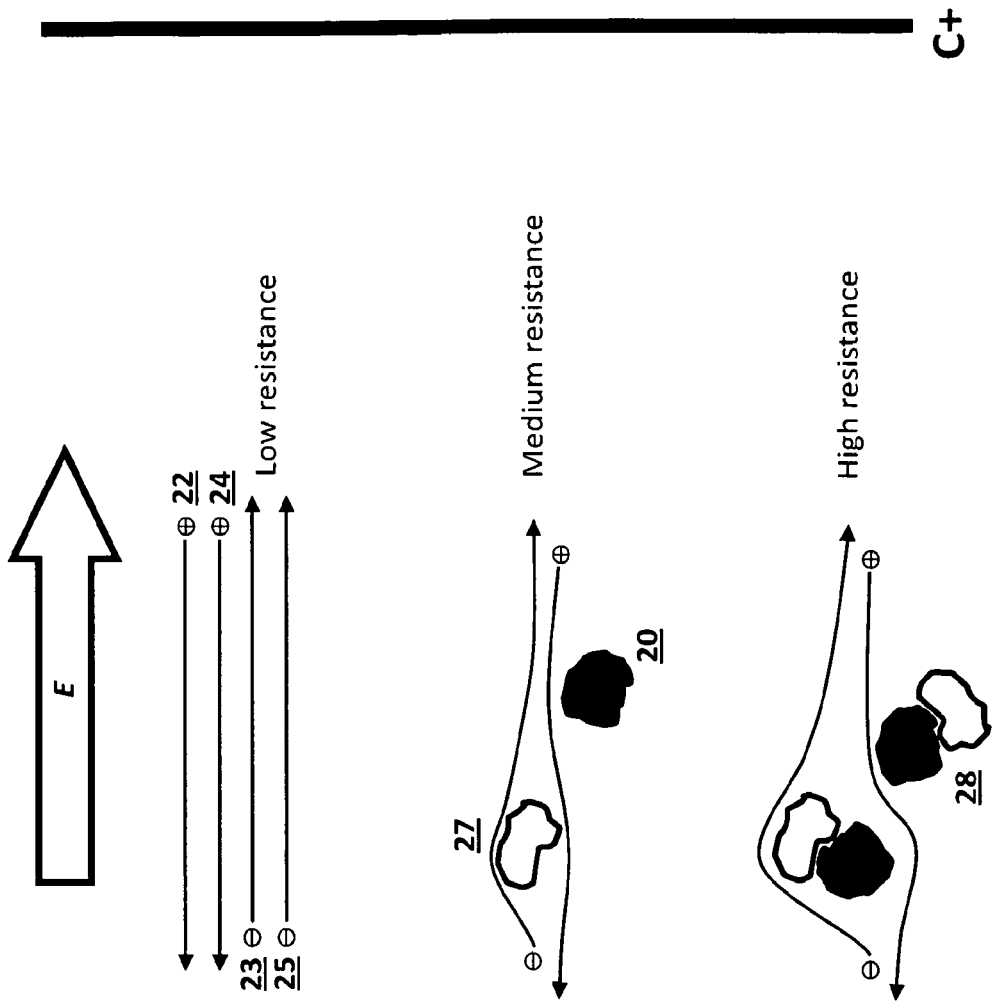
FIG. 27 is a schematic of electrolyte migration around molecular obstacles for a) no obstacles b) small obstacles and c) substantial obstacles.

Referring to FIG. 27, a small electrolyte cation 22 and small electrolyte anion 23 may be moved in a straight line by an electric field if there are no obstacles in its path. However, if there are obstacles, such as an analyte particle 20 and an analyte particle 27, then the cations 22 and anions 23 will need to go around the analyte particles, slowing down the ionic axial movement. If the analyte particles have a binding interaction, they will form a large complex 28, causing the ionic axial movement to be slowed down even more. For example, a typical protein, such as Bovine Serum Albumin (BSA), has a size of about 4 nm×4 nm×14 nm. With a TEPC filter 1 hole 2 diameter of 50 nm, a single BSA protein molecule would be blocking a significant, fraction (0.8% to 2.9%) of the cross-sectional area of the hole 2, and hence significantly reduce the ionic particle flow.

Figure 28:
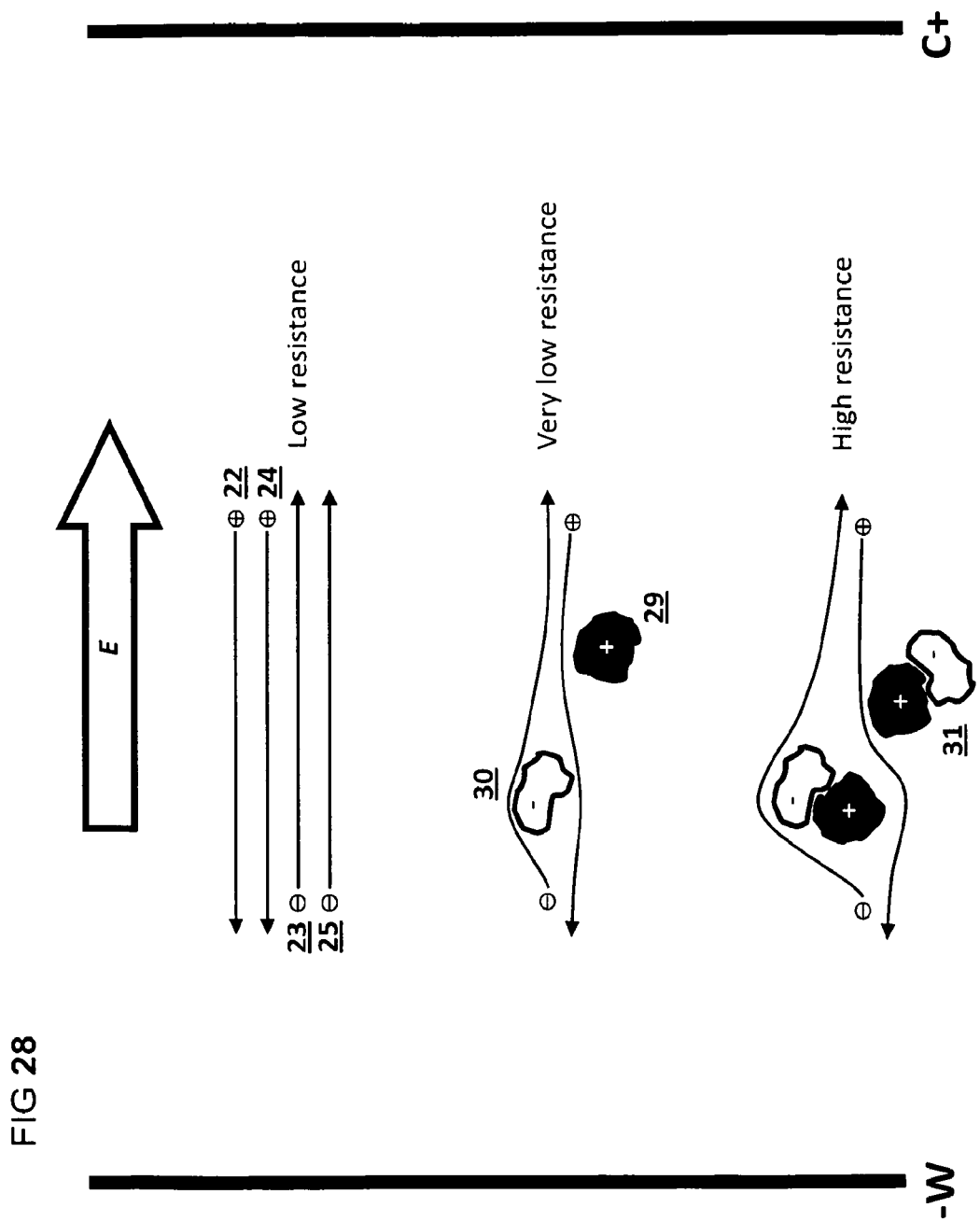
FIG. 28 is a schematic of electrolyte migration around charged molecular obstacles for a) no obstacles b) small obstacles and c) substantial obstacles.

Referring to FIG. 28, obstacles 29, 30, and 31 themselves may have an electric charge. Upon application of an electric field, they may interact in complex, ways with the movement of the electrolytes or redox reagents.

Figure 31:
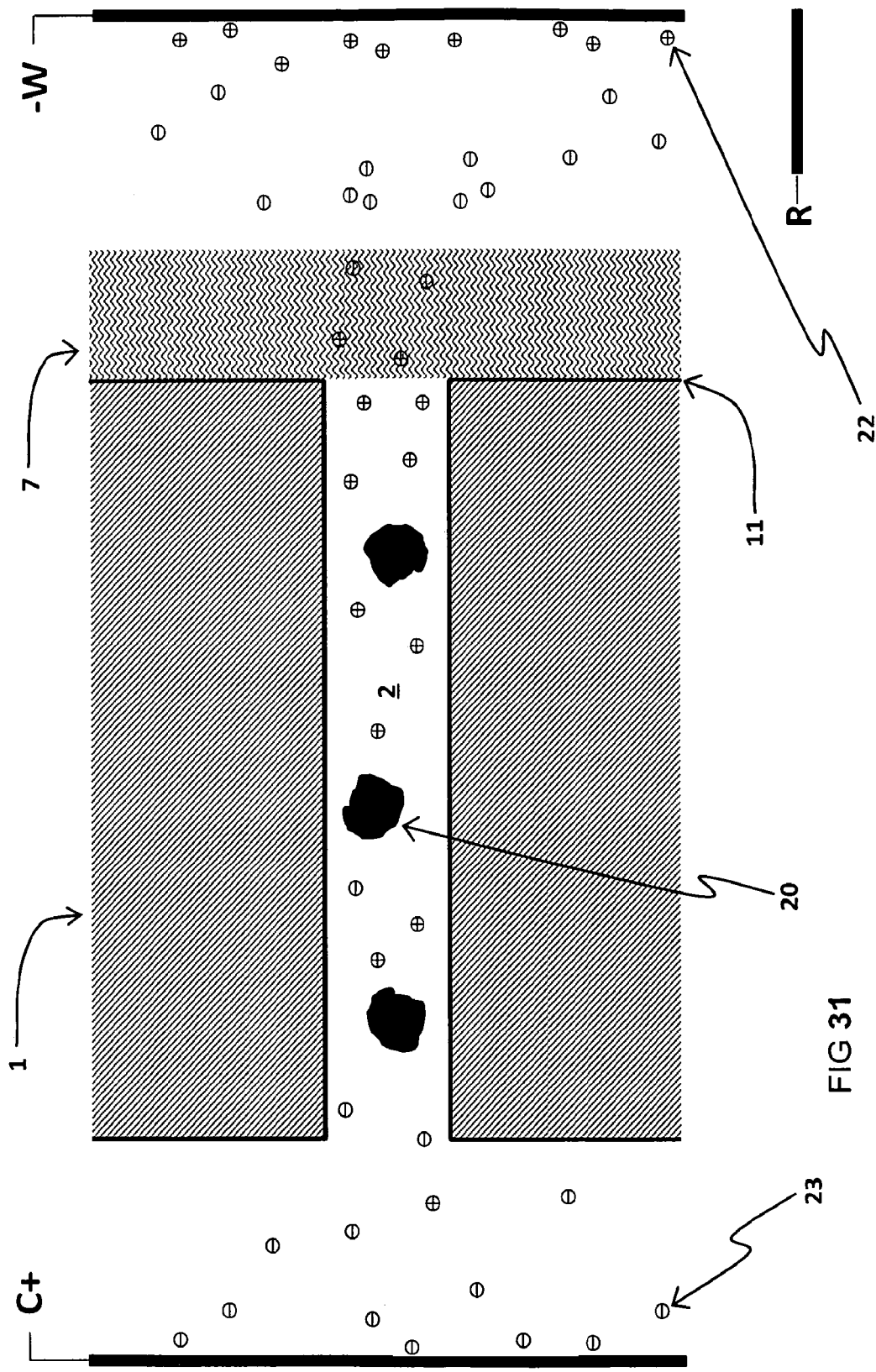
FIG. 31 is a schematic of electric current flow to an electrode.

The transmission of electrolyte molecules or redox reagents through the gel 7, dependent upon obstacle characteristics within the hole 2, provides a sensitive way to perform measurements of the obstacle characteristics. FIG. 31 illustrates the application of an electric field with Working, Counter, and Reference electrodes. The ionic particle flow will create an electric current in the electrodes that is resisted by both the obstacles and by the gel 7, but since the resistance of the gel 7 is relatively constant, this resistance can be subtracted out by cycling the measurements.

Figure 32:
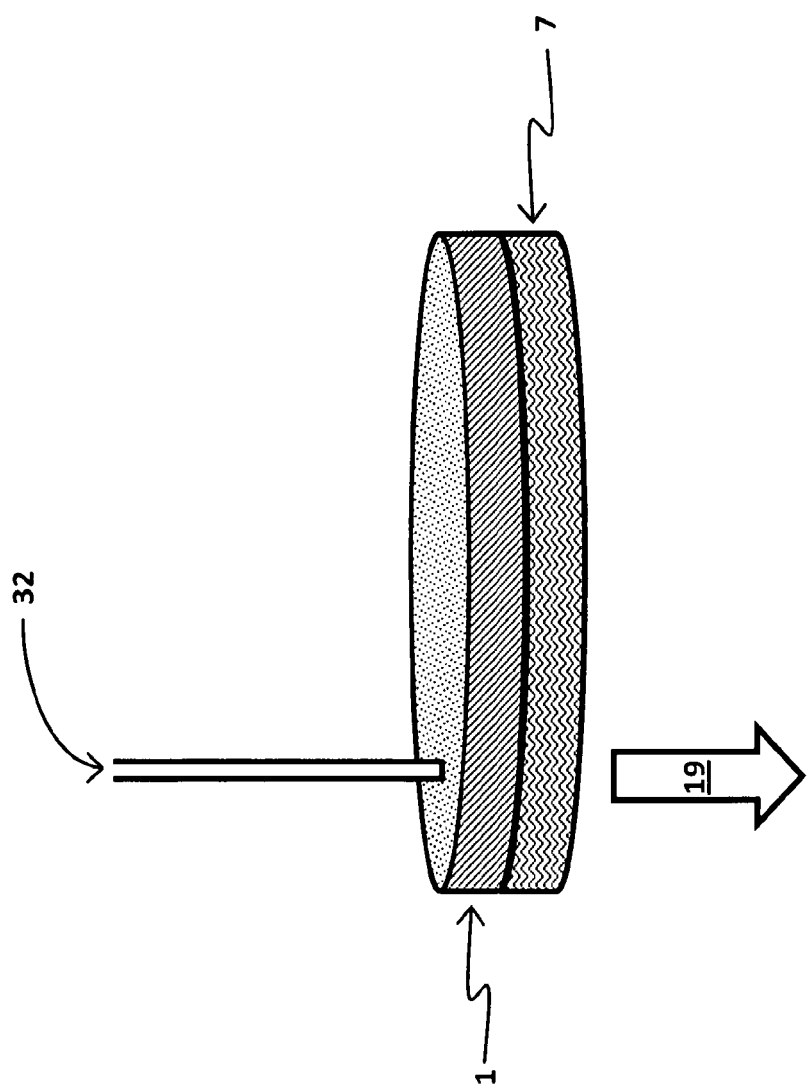
FIG. 32 is a schematic of how analyte particles are loaded into the holes of the structure of FIG. 9.

The overall apparatus in the sample loading state is shown in FIG. 32. A fluid flow of analyte particles, such as a complex sequence of proteins eluting from, a chromatography column 32, is directed to flow into a particular region of the TEPC filter 1. A lower pressure on the opposite side causes the solvent and other small molecules to pass through the TEPC filter 1 and gel 7, accumulating analyte particles within the TEPC filter 1 holes 2. As analyte particles are eluted from the chromatography column 32, the TEPC filter 1 surface is moved in a scanning motion. The different analyte particles that elute are trapped in spatially distinct locations within the TEPC filter 1. Following this operation, a second scan may be done with different analyte particles elating from the chromatography column 32, producing a large number of unique binary mixtures (of controllable proportions) across the area of the TEPC filter 1. Further scans could be used to add even more complexity to the populations within the holes 2. This would be functionally equivalent to "Sandwich Array" technology, for reducing the problem of protein cross-reactivity, it is even possible to include lipid micelles, colloids, immobilized materials, or Phage Antibody Display technology within the holes 2, allowing retained analyte particles to interact with that environment. Furthermore, it is possible to extract analyte particles from one set of holes 2 and add it to another set of holes 2.

Figure 33:
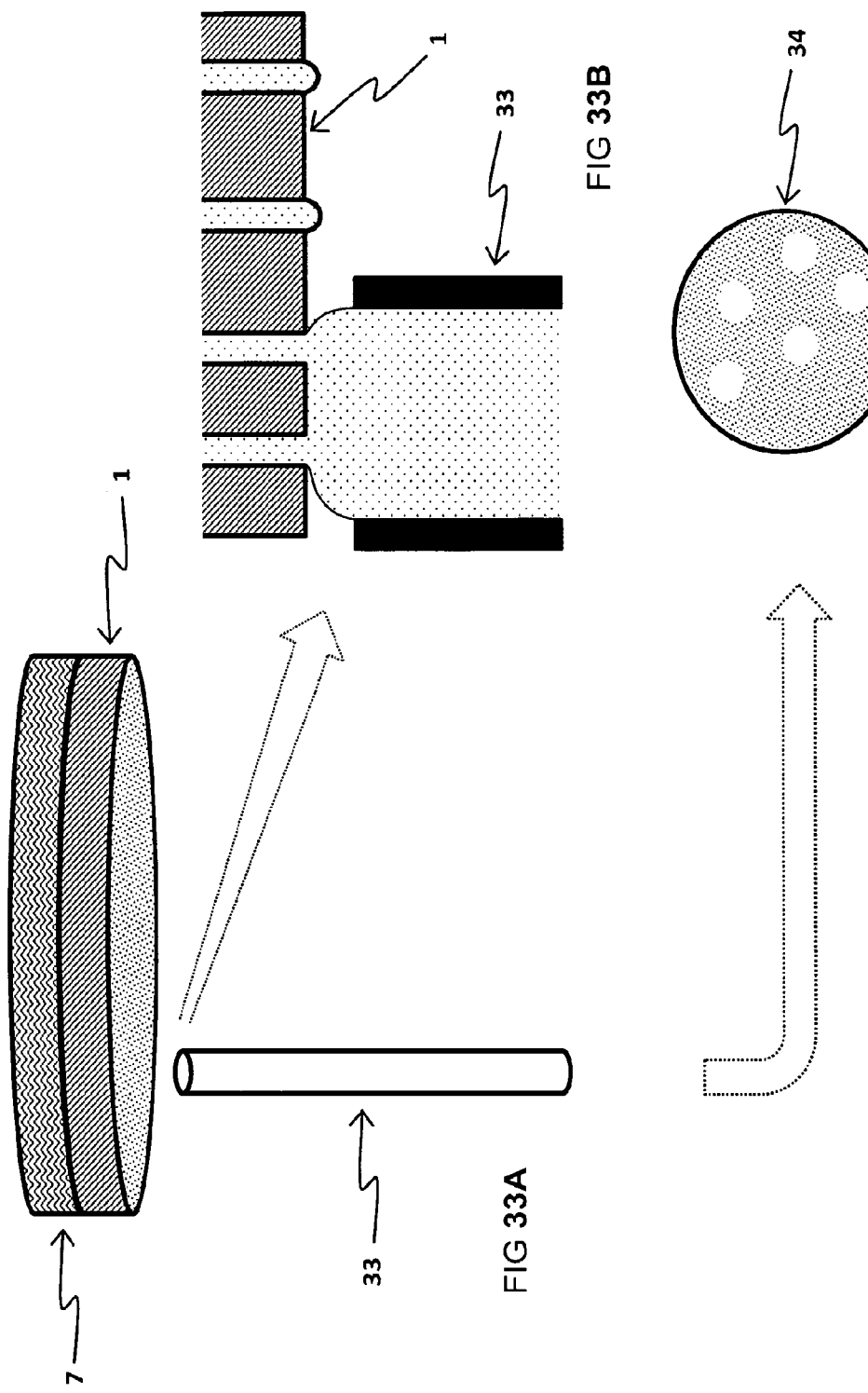
FIG. 33A is a schematic of how electric current is detected in an analytically useful way.
FIG. 33B is an expanded view of the tip of the tube that delivers analyte particles in FIG. 33A.
FIG. 33C is a view of the conductance map resulting from FIG. 33A.

The overall apparatus in the measurement state is shown in FIG. 33. An electrode 33, or plurality of electrodes, is scanned across the surface such as the TEPC filter 1 surface, and the electric current measured. Information about the position of the electrode and the electric current is compiled into a conductance map 34. Examples of the structure of the electrode include an exposed metal surface surrounded by an insulator, and a tube filled with conductive fluid.

Figure 35:
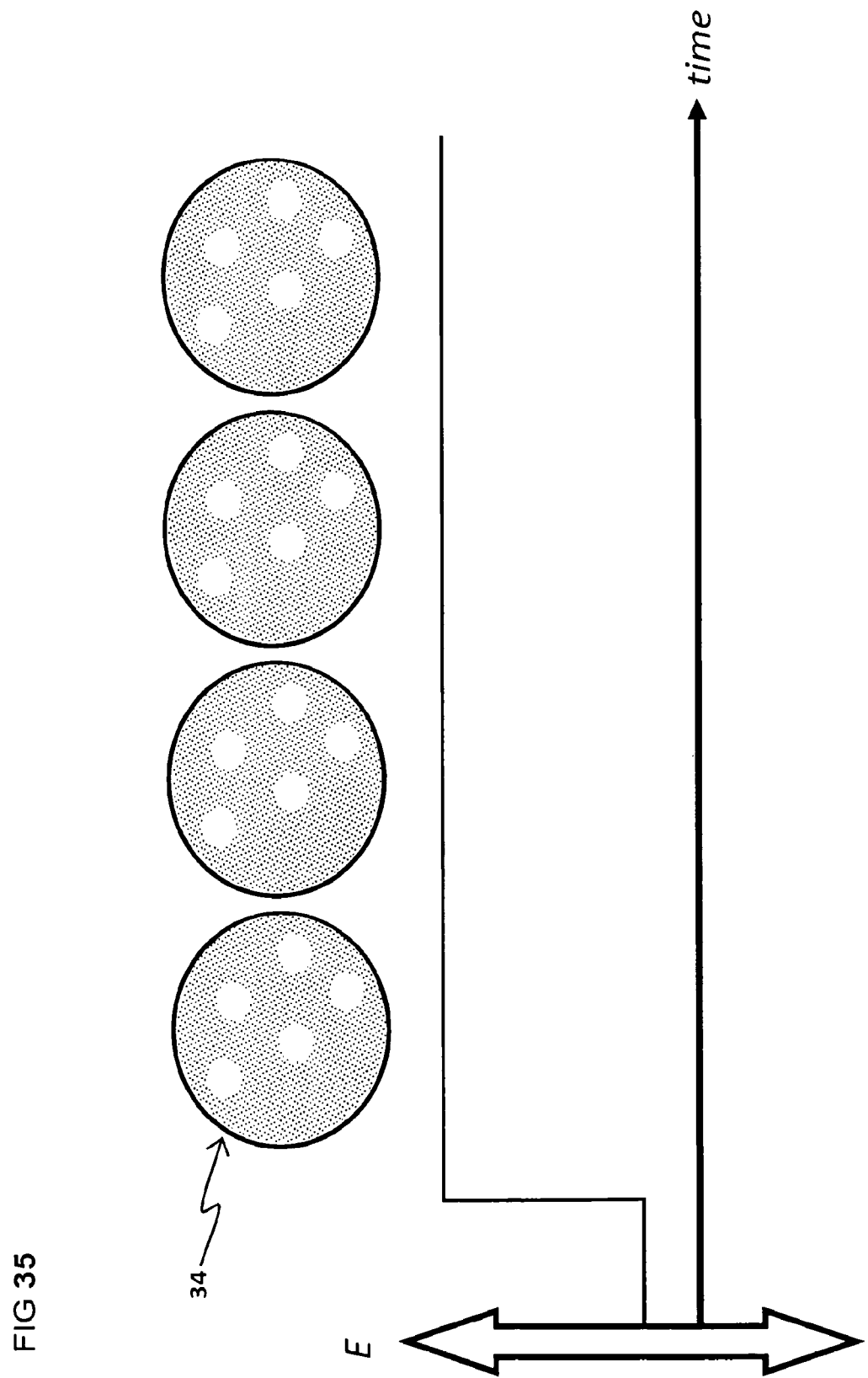
FIG. 35 is an illustration of the conductance maps that evolve over time when the electric field is applied.

Referring to FIG. 35, the result of measurement is a set of largely uniform conductance maps 34. Most of the area is uniformly conductive with the exception of a few low-conductance areas having significant migration obstacles (e.g. analyte particles). The characteristics of these low-conductance areas, relative to the uniformly conductive areas, is the basis of the analytical signal.

Referring to FIG. 33, restriction of the area to be measured can be achieved by an insulating tube, filled with an electrically conductive fluid, with one end in physical contact with said sheet of material, an insulating sheet with a hole that is applied to the surface of said sheet of material, or an insulating water-immiscible fluid that is applied to the surface of said sheet of material. In the latter case, upon pressurization of the gel side of the TEPC filter 1, surface tension of water within the holes forms isolated aqueous protuberances along the other surface of the TEPC filter 1, that may be scanned with an insulating tube, filled with an electrically conductive fluid.

Figure 37:
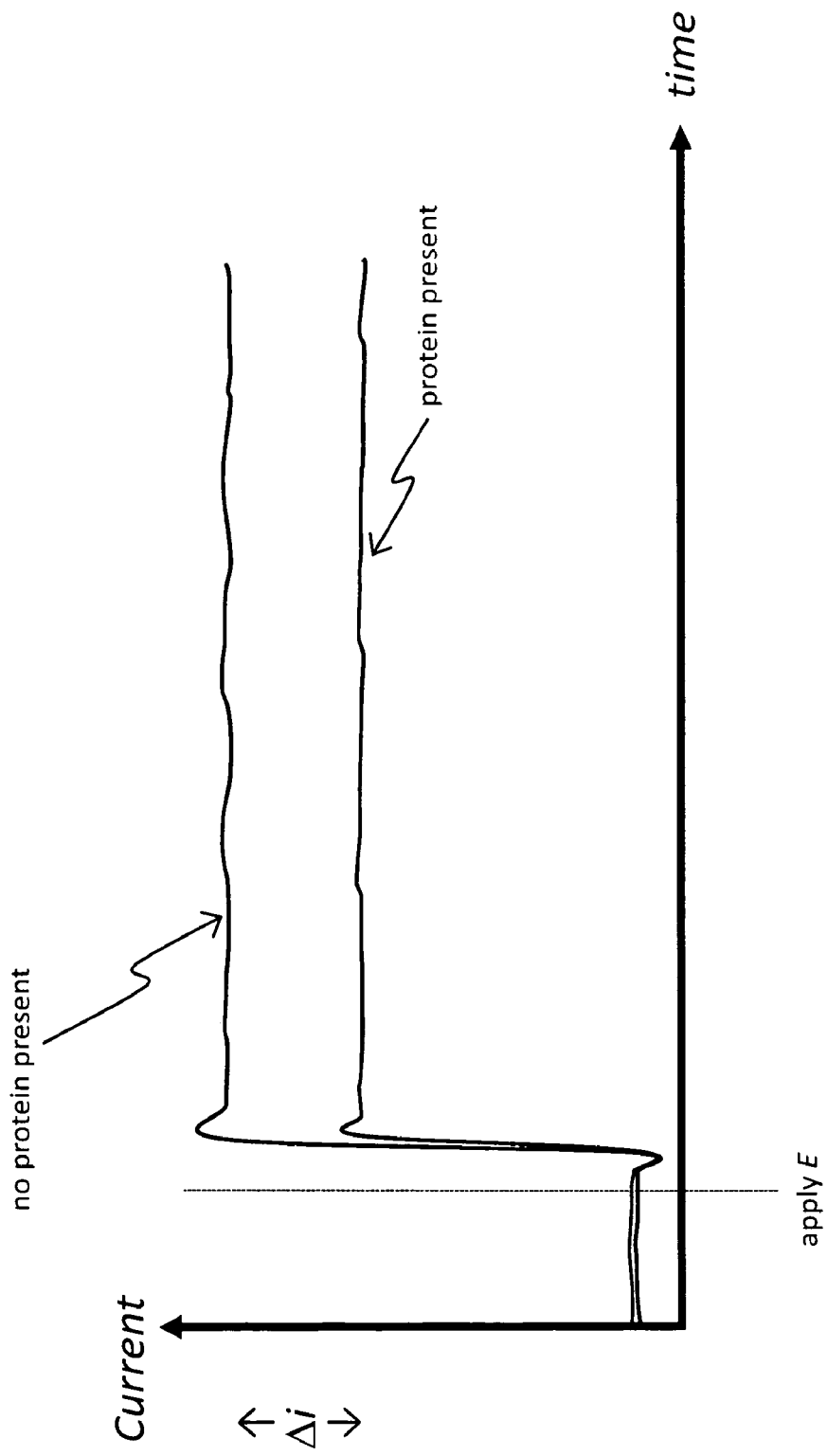
FIG. 37 is an illustration of a vertical (increasing) shift in the electric current for a small grouping of holes, protein molecules absent versus protein molecules present.

Referring to FIG. 37, the electrical conductance is graphed as a function of time for an area that has protein present, and another area that has no protein present. After the electric field E is actuated, the presence of protein causes a vertical (increased) shift in the current i level, which can be quantified by a delta current i measurement.

Figure 39:
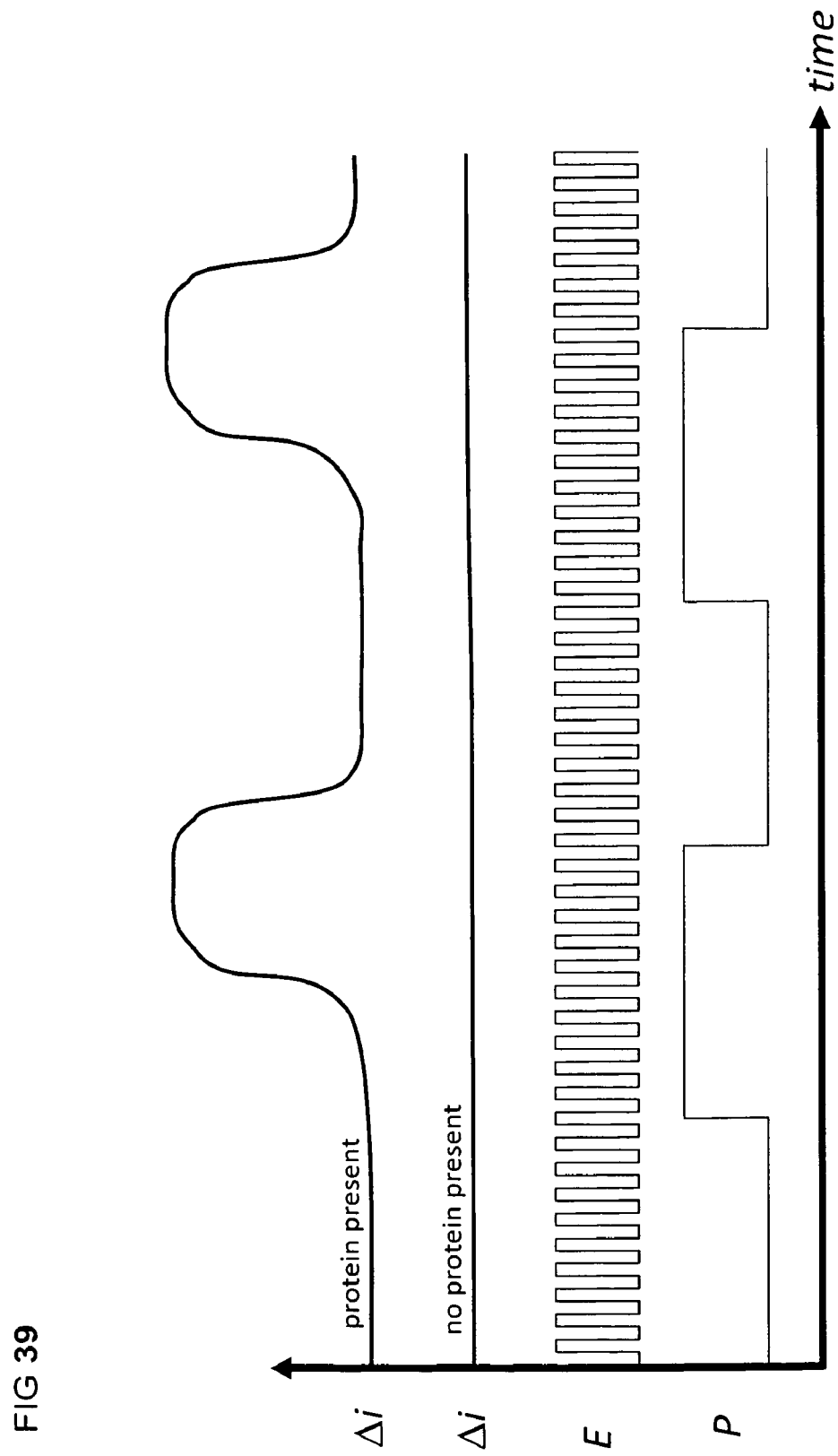
FIG. 39 is an illustration of repeated delta current measurement of the presence of protein molecules in a small grouping of holes, and the absence of protein molecules in another small grouping of holes.

Referring to FIG. 39, the theoretical results for protein present versus no protein present are compared. The electric field E is repeatedly actuated in a cycle, yielding repeated delta current i measurements. On a longer time scale, the hydrodynamic pressure P is also repeatedly actuated in a cycle. When increased pressure causes protein to accumulate, the delta current increases. When the pressure is released, the protein diffuses outward, and the delta current decreases. Cycling the hydrodynamic pressure thus provides a continual series of delta current peaks that can be averaged for sensitive detection of the presence of the protein.

Figure 41:
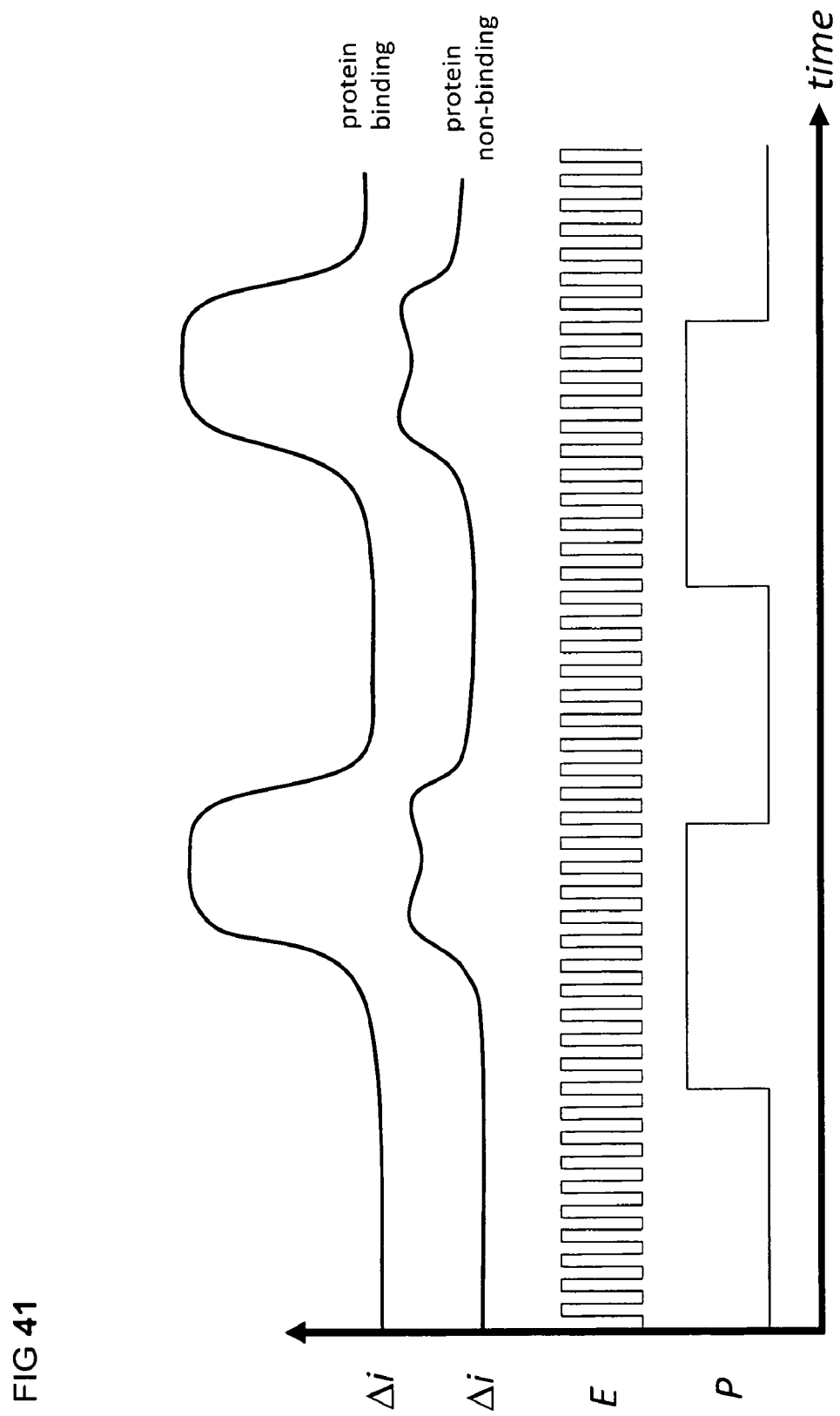
FIG. 41 is an illustration of repeated delta current measurement of protein binary interaction in a small grouping of holes, and of protein binary non-interaction in another small grouping of holes.

Referring to FIG. 41, the theoretical results for protein binding present versus protein non-binding are compared. Protein that binds to another protein will have greater steric effects, becoming a large obstacle and having a slower diffusion rate; this results in a series of continual delta current i peaks that are of large amplitude. Protein that does not bind to another protein will have lesser steric effects, not becoming a large obstacle and not having a slower diffusion rate; this results in a series of continual delta current peaks that are of small amplitude. Note that since there are multiple proteins present, this smaller amplitude may have multiple peaks.

Figure 43:
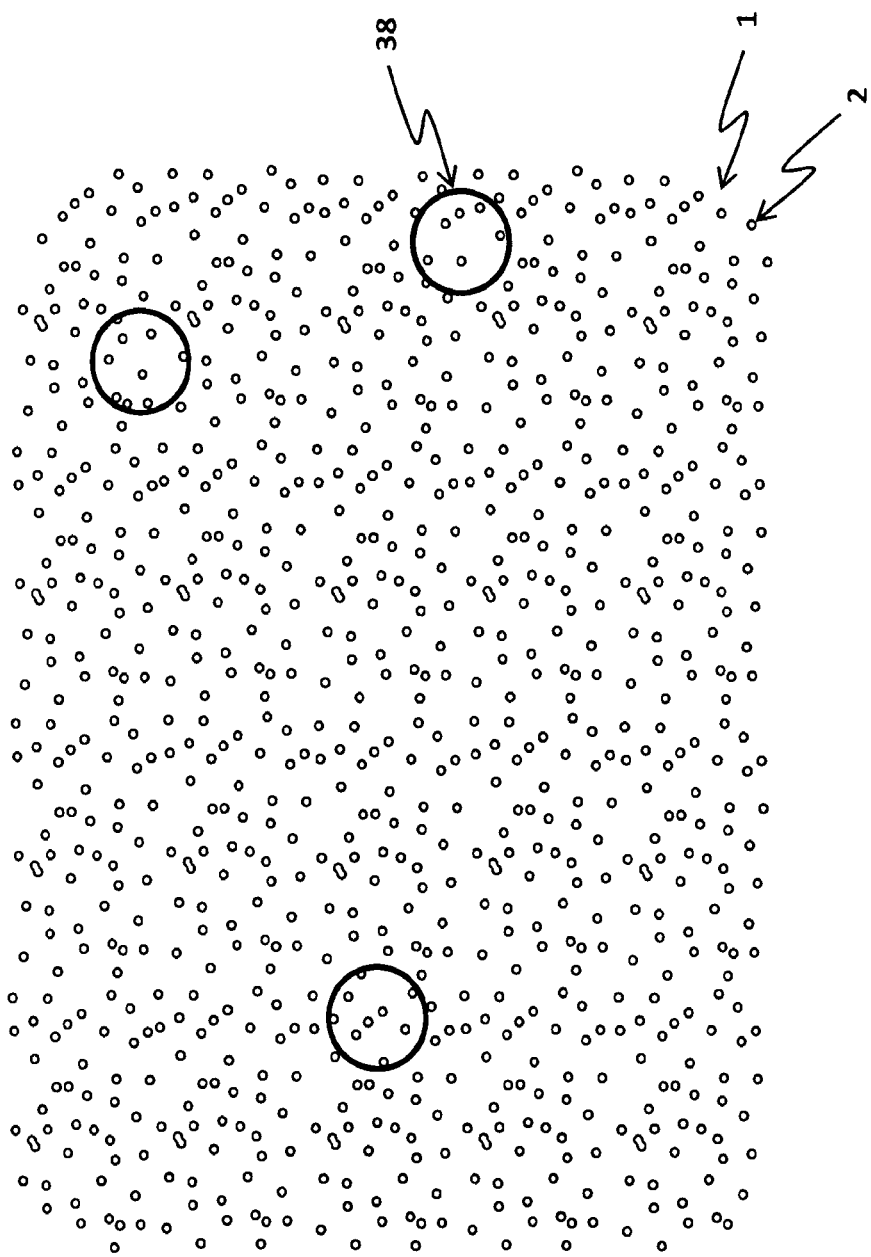
FIG. 43 is a schematic of a large population of holes of the perforated material of FIG. 9.

A summary of the measurement results is shown in FIG. 43. The measurements provide a map of the analyte particle characteristics across the area of the TEPC filter 1. Certain areas 38 will have measurement characteristics of interest to a scientist performing the method. The identity of the contents of these areas can then be done by a variety of techniques, such as by mass spectrometry, or by knowledge of the chromatography system that originally delivered the contents.

Substantially the same functionality may be achieved by use of similar structures, such as a perforated monolayer film instead of a TEPC/gel structure, where diffusion is radial instead of axial.

Second Embodiment Summary

A specially-constructed, layered material forms a set of reservoirs that are loaded with a variety of spatially-separated analyte particles, and said layered material imaged for fluorescence emission. This yields a map of the characteristics of the various analyte particles, which can provide useful information about biological samples.

Method in Accordance with a Second Embodiment of the Invention

In a method in accordance with a second embodiment of the invention, a perforated material, such as a TEPC filter, has holes with restricted openings. Homogeneous or heterogeneous populations of analyte particles within a controlled matrix are loaded into the TEPC filter holes, and fluorescence is used to measure the diffusion outwards, which is a measure of presence, structural changes, and any binding interactions involving the analyte particles.

The method of the invention will now be described by way of reference to FIGS. 1 to 43.

Referring to FIGS. 1A, 1B, and 2, the TEPC filter 1 has a random distribution of uniformly-sized holes. FIG. 1A shows the top view, and FIG. 1B is a cross sectional view. The TEPC filter 1 may have an outer surface chemically derivatized with carboxylate moieties 3. Other materials having similar characteristics may be substituted.

Referring to FIGS. 3, 4, and 5, a bilayer material may be formed by the following process. Firstly, a dilute suspension of spheroids 4 of uniform size is formed in a matrix of a gel precursor (such as acrylamide or melted agarose). The suspension is then applied to a thin plastic sheet 5 and wrapped around a smooth cylinder 6 that has a hydrophobic surface. The gel 7 is formed by chemical, thermal, or light polymerization. An example of chemical polymerization is illustrated in FIG. 4. The spacer particles 4 enforce a uniform, known thickness to the gel 7. After polymerization, the thin plastic sheet 5 is peeled off of the smooth cylinder 6, creating a bilayer material 8 consisting of a gel 7 layer and a plastic 5 layer. A magnified view of this bilayer material is shown in FIG. 5; the spheroids 4 are not shown in this magnified view because they axe sufficiently dilute. The chemistry of the bilayer material 8 interface 9 is chosen such that the thin plastic sheet 5 layer may be easily removed in the future by physical or chemical means. The outer surface of the gel 7 may be chemically derivatized with amino moieties 10, but these are indigenous to polyacrylamide.

Alternatively to said bilayer material, a gel precursor may be sandwiched between two hydrophobic smooth plates, and allowed to polymerize and dry. This forms a robust dried, gel film that can be easily handled, and then re-hydrated when needed.

Alternatively to said bilayer material a dialysis membrane may be used, which may be purchased commercially from many vendors, such as Millipore or Whatman.

Referring to FIGS. 6, 7, and 8, the bilayer material 8 may be chemically bonded to the TEPC filter 1. An example of a chemical bonding mechanism is shown in FIG. 6, where carboxylate moieties and amino moieties chemically bind to form a peptide bond 11. Other chemistries may be substituted. FIG. 7 shows the TEPC filter 1 and the bilayer material 8 in close proximity, with the carboxylate derivatized surface 3 and the amino derivatized surface 10 facing each other. FIG. 8 shows the TEPC filter 1 and the bilayer material 8 chemically bonded, together with the peptide bond 11.

Referring to FIGS. 8 and 9, the thin plastic sheet 5 may be removed by physical or chemical means, leaving only the gel 7 layer adhered to the TEPC filter 1.

Alternatively to said chemical bonding, the gel 7 layer and the TEPC filter 1 may simply be compressed together by physical force without chemical bonds, such as by wrapping around a cylinder and tensioning the outer TEPC filter 1 layer.

Alternatively to said chemical bonding, the TEPC filter 1 may be placed on a surface of a conductive fluid that is immiscible with the fluid comprising the analyte matrix.

There are a number of variations that are possible to the schematic shown on FIG. 9, and the examples of these are shown in FIGS. 10, 11, 12, 13, 14, 15, and 16. Although the remainder of this Method will focus on the simple case of FIG. 9, it will be appreciated that these variations are also applicable.

Referring to FIG. 10, the outer surface of the gel 7 may be chemically derivatized with fluorophores 12, surfactants 13, other materials, or any combination of materials. Likewise, the inner surface of the gel 7 (facing the hole 2) or the inner surface of the hole 2 may also be chemically derivatized.

Referring to FIGS. 11, 12, and 13, a spheroid 14 may be lodged in the opening of the hole 2, prior to formation of the peptide bond 11. This spheroid 14 would have a diameter slightly larger than the diameter of the hole 2. The gel 7 layer would be dimpled by the presence of the spheroid 14, creating an empty volume 15 around the spheroid 14. A force 16, such as from a magnetic field gradient, electric field, gravitational field, or hydrodynamic flow, may be used to lift the spheroid 14 from its seating in the opening of hole 2, creating a small gap 17 between the surface of the spheroid 14 and the opening of the hole 2. The empty volume 15 may be removed by brief heating of the spheroid 14 to melt the surrounding gel 7, or by saturation with gel precursors followed by chemical polymerization. The resulting structure is shown in FIG. 13.

Referring to FIGS. 14 and 15, both ends of the hole 2 may be capped by spheroids 14. If the gel 7 is sufficiently pliable, then one of the spheroids 14 may be removed by a force, such as from a magnetic field gradient. This would leave a small tear 18 in the gel 7. This particular configuration would be especially useful for retention of materials within the hole 2 without an active retention mechanism.

Referring to FIG. 16, the gel may be not used, and foe spheroid 14 held in place with a force, such as from a magnetic field gradient 16.

Focusing on the simple example of FIG. 9, this structure may be used to collect and concentrate analyte particles within the hole 2. FIG. 17 is a schematic of fluid flow 19 passing from the open end of the hole 2, through the hole 2, and then through the gel 7. Analyte particles that are suspended within the fluid flow 19 become filtered by the gel 7, if the gel 7 has a sufficiently tight cross-linked structure to prevent passage. Examples of such analyte particles are proteins 20, nucleic acids, viruses, protoplasmic structures. Quantum Dots, large fluorophores 21, large electrolyte cations, large electrolyte anions, and large redox reagents. The permeability of the gel 7 may be reduced by inclusion of particles within the gel 7 during formation. Examples of particles that are able to pass through the gel 7 are water molecules, small electrolyte cations 22, small electrolyte anions 23, and small redox reagents. FIG. 18 is a schematic of the net result of accumulated, analyte particles within the hole 2.

Once there are accumulated analyte particles in the hole 2, the fluid flow 19 can be stopped. At this point, the accumulated analyte particles will begin to diffuse outward, eventually emptying the hole 2. The fluid flow 19 may then be reinstated, and the accumulation/diffusion cycle repeated. A gel that weakly limits diffusion may be placed at the hole 2 outlet, to improve cyclability. A gel that weakly limits diffusion may be placed within the hole, to extend the diffusion times.

During diffusion, the analyte particles in the hole 2 would have movement pathways that can intersect with ionic or fluorescent particles. Since the particles can not pass through each other, they go around each other, slowing down, the movement pathways of the ionic or fluorescent particles. This slowing down is dependent on the presence of analyte particles and their binding processes, and thereby forms the basis of this Method.

During diffusion, the analyte particles in the hole 2 may be driven axially with a migration force (e.g. force resulting from an electric field) in addition to diffusion.

This process is also applicable to the accumulation part of the cycle, but analysis is complicated by the addition of fluid flow 19 forces.

During the diffusion or accumulation parts of the cycle, the fluid flow 19 may be given a high-frequency axial oscillation, for the purpose of modifying particle movement. For example, the spheroid 14 of FIG. 15 may have a magnetic moment and be magnetically oscillated to pump large analyte particles through the tear 18. As another example, the outer (or inner) surface of the gel 7 in FIG. 9 may be subjected to pressure pulsations, causing the analyte particles within the hole 2 to likewise oscillate.

There are numerous mechanisms by which particles in the hole 2 may by driven axially with a force in addition to diffusion. Examples of some of these mechanisms are illustrated in FIGS. 19, 20, 21, and 23.

Figure 19:
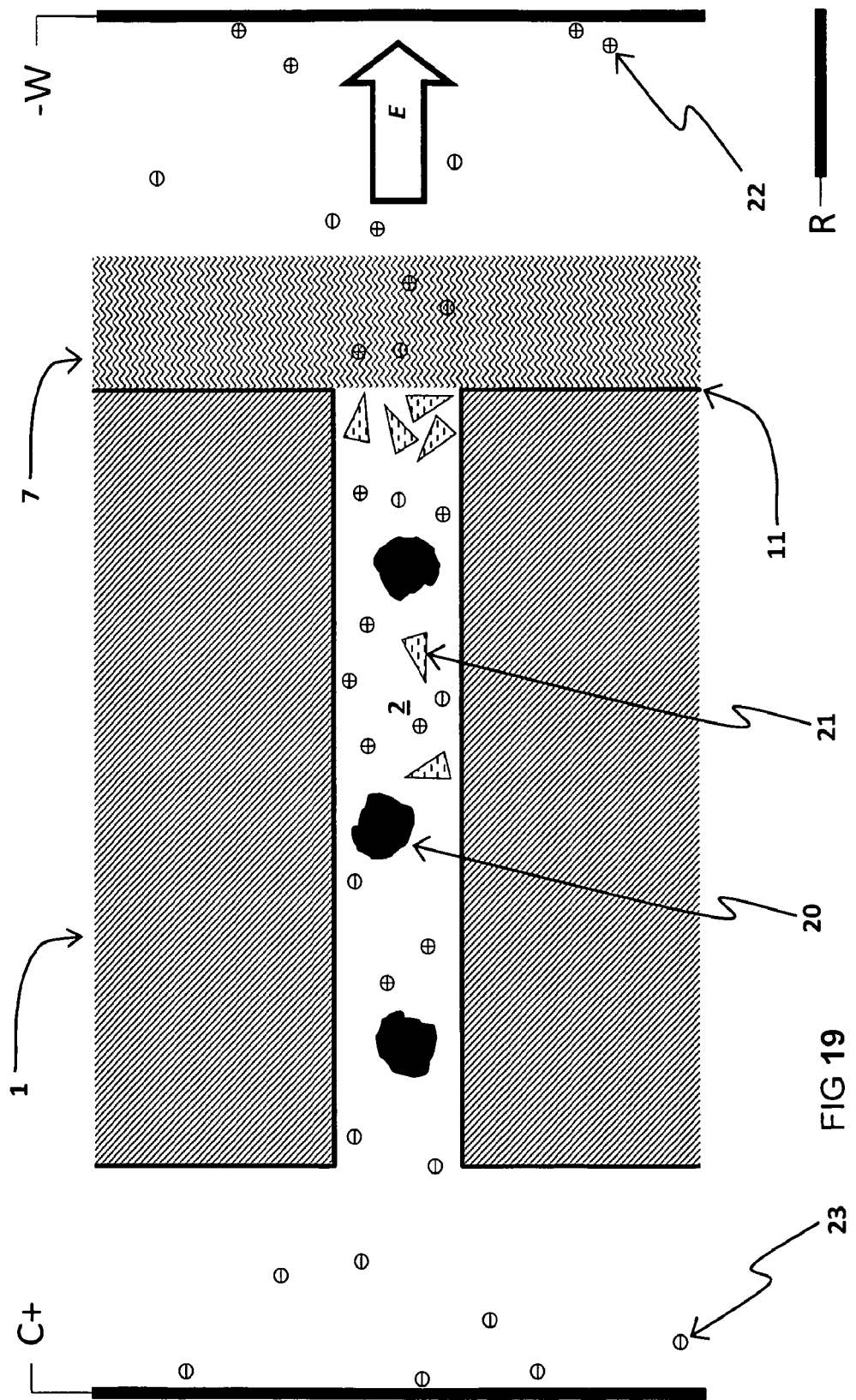
FIG. 19 is a schematic of fluorophore migration induced by an electric field E.

Referring to FIG. 19, fluorophores that are unable to traverse the gel 7 are moved towards (or away from) the inner gel 7 surface by an electric field generated by Working (−W), Counter (C+), and Reference (R) electrodes.

Figure 20:
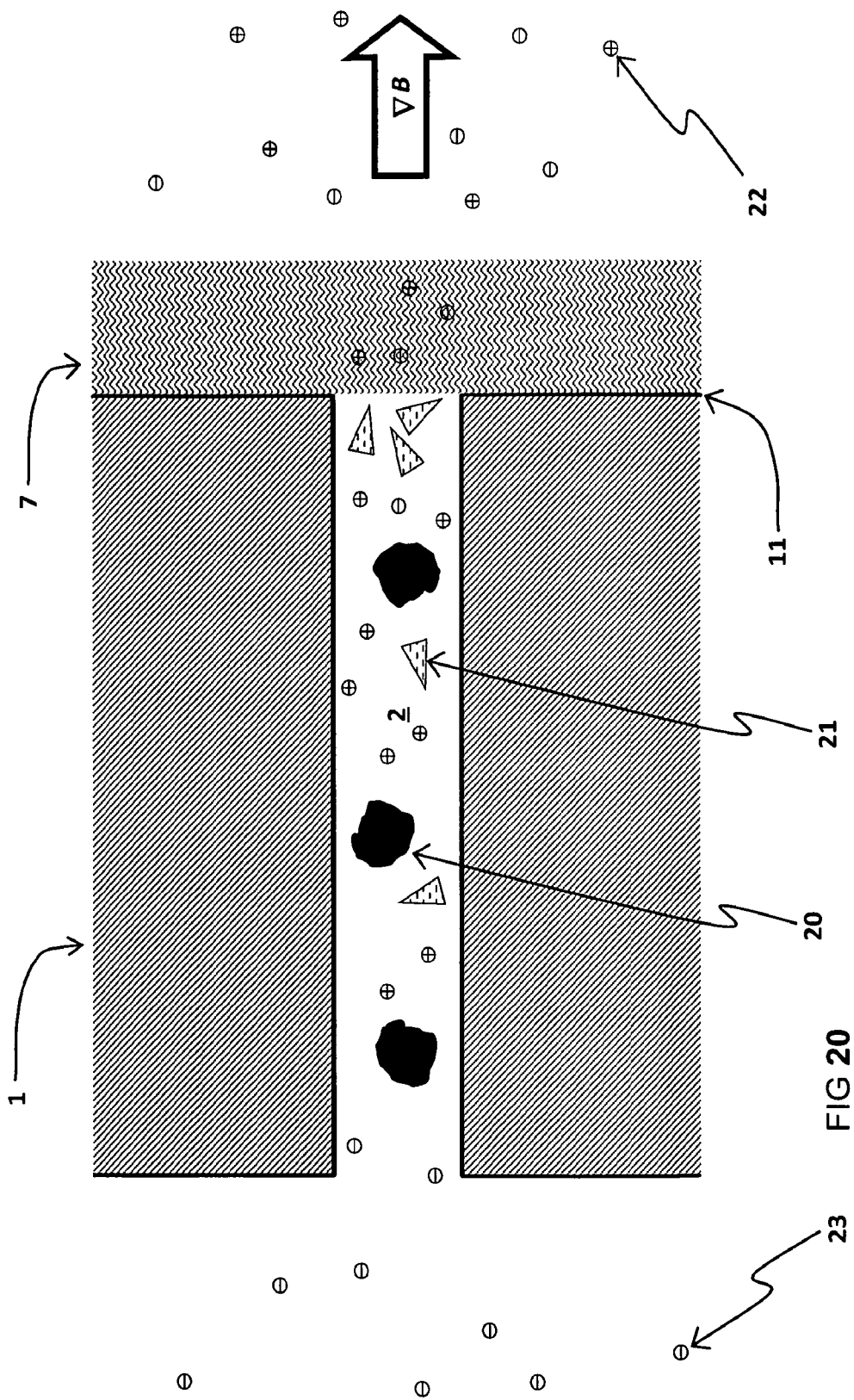
FIG. 20 is a schematic of fluorophore migration induced by a magnetic field gradient nabla B.

Referring to FIG. 20, fluorophores that are unable to traverse the gel 7 are moved towards (or away from) the inner gel 7 surface by a magnetic field gradient.

Figure 21:
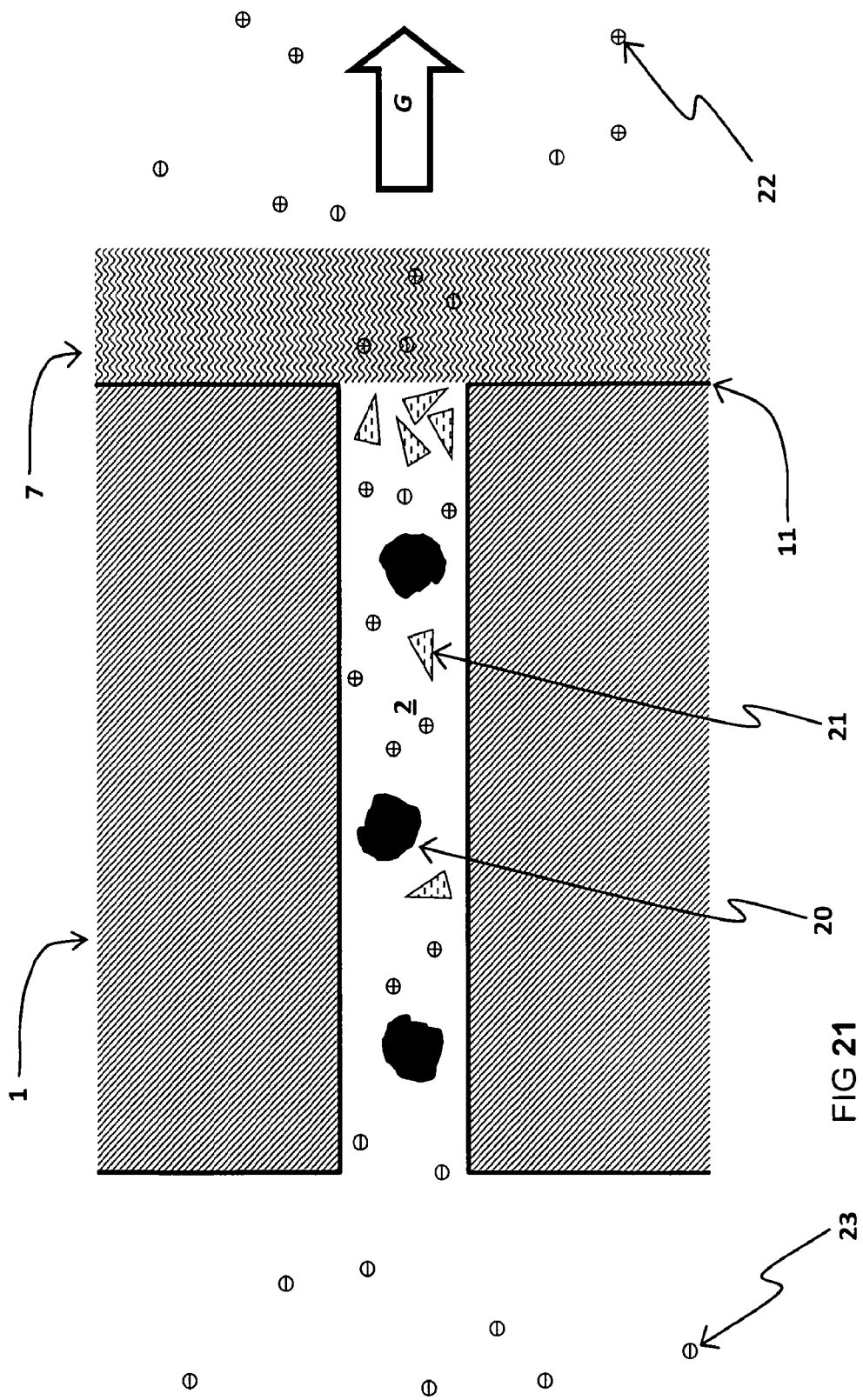
FIG. 21 is a schematic of fluorophore migration induced by a gravitational field G.

Referring to FIG. 21, fluorophores that are unable to traverse the gel 7 are moved towards (or away from) the inner gel 7 surface by a gravitational field.

Figure 23:
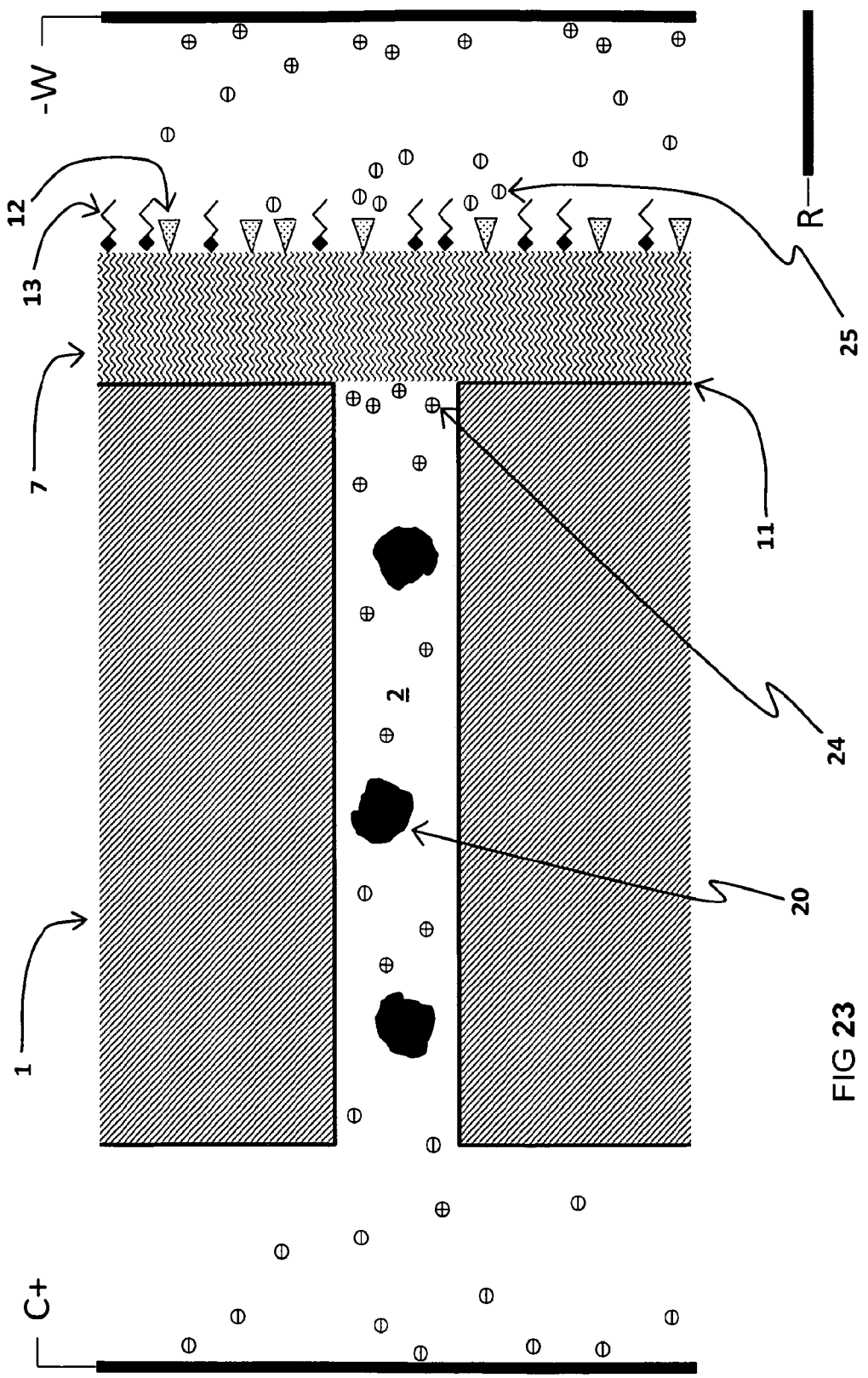
FIG. 23 is a schematic of capacitor formation, resulting from electrolyte migration induced by an electric field E.

Referring to FIG. 23, large electrolyte cations 24, large electrolyte anions 25, or redox reagents that are unable to traverse the gel 7 are moved towards (or away from) the inner gel 7 surface and the outer gel 7 surface by an electric field, creating a capacitor.

Figure 24:
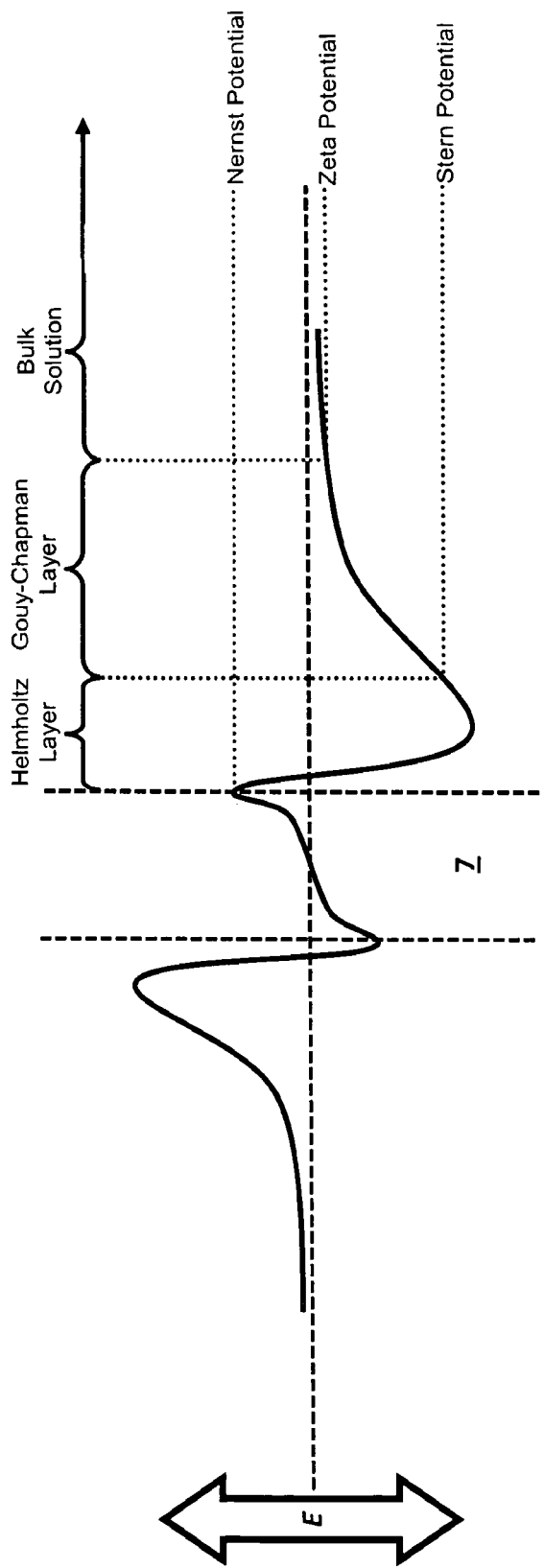
FIG. 24 is an illustration of the electric field associated with the capacitor of FIG. 23.
Figure 25:
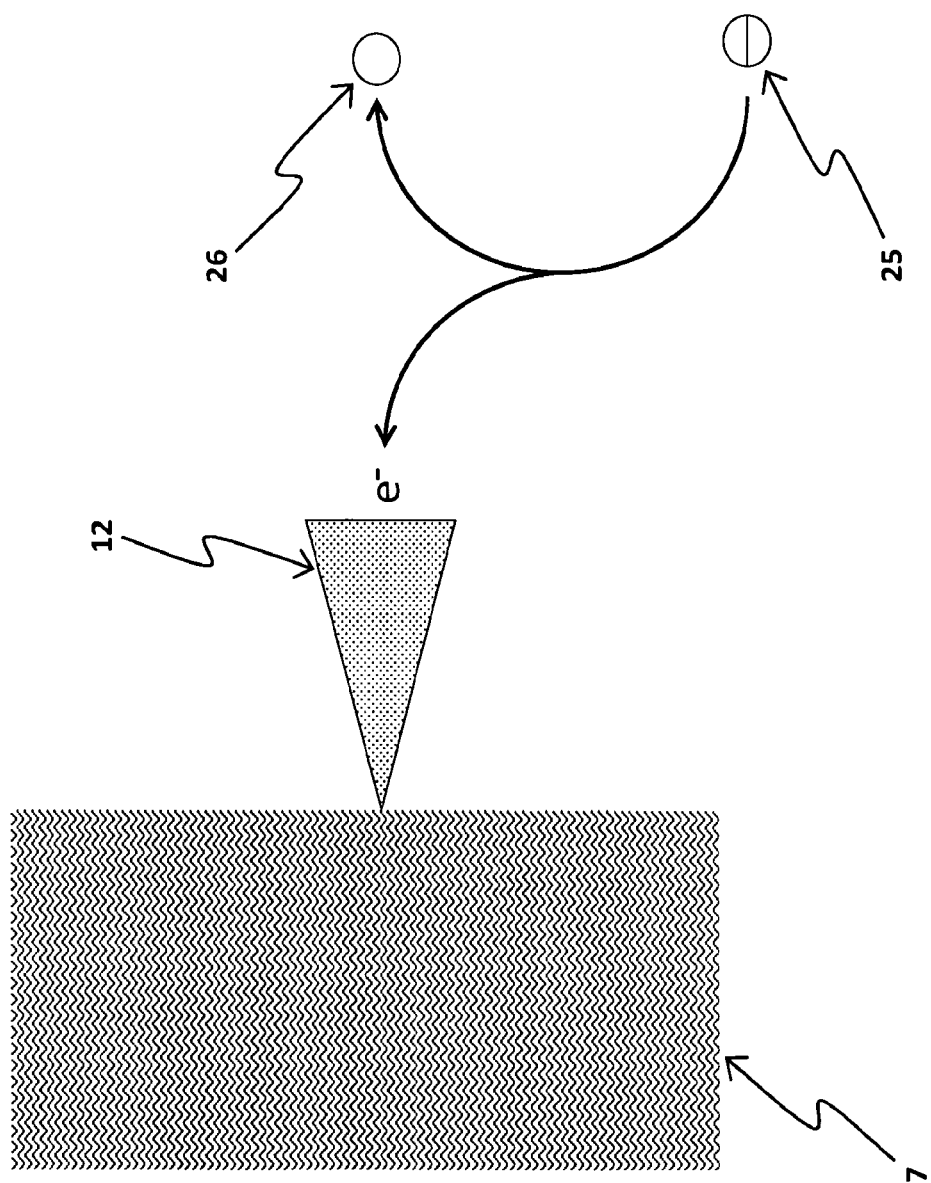
FIG. 25 is an illustration of the transfer of electric charge to the fluorophore of FIG. 23.
Figure 26:
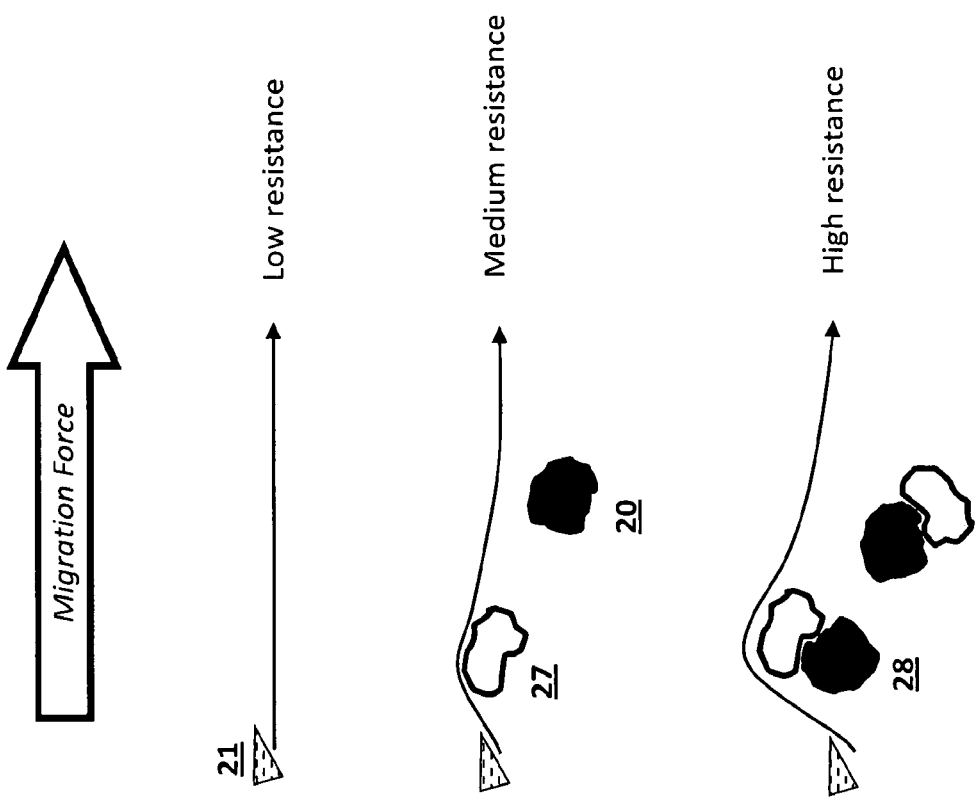
FIG. 26 is a schematic of fluorophore migration around molecular obstacles for a) no obstacles b) small obstacles and c) substantial obstacles.

The capacitor has behavior that warrants additional description in FIGS. 24, 25, and 26.

Referring to FIG. 24, the electric field that is axial to the hole 2 has a complex structure. This complex structure is analogous to the electric field that exists near metallic electrodes in ordinary electrochemical studies. At a distance far away from the outer surface of the gel 7, in the bulk, solution, the electric field is small, and does not change significantly with distance. Approaching the outer surface of the gel 7, the electrolyte exhibits an increased, concentration, causing the electric field to rise exponentially; this is commonly called the Gouy-Chapman Layer. Extremely close to the outer surface of the gel 7, the electrolyte forms a double-layer of alternating charge; this is commonly called the Helmholtz Layer. The presence of surfactant, molecules 13 may assist in the shaping of the field within the Helmholtz Layer. Continuing onward into the gel 7, the electric field subsides. Upon exiting the gel 7 on the inner surface, the electric field has a structure that mirrors the structure for the outer surface.

Referring to FIG. 25, the strong electric field in the Helmholtz Layer of the outer gel 7 surface causes an electric charge, such as an electron, to be transferred from an electrolyte (or a suitable redox reagent) anion 25 (or cation) to a fluorophore 12 bound to the surface. After the molecule 25 transfers its charge, it becomes another molecule 26. The fluorophore 12 will have its fluorescence characteristics changed by the charge transfer. For example, fluorescein in its uncharged state is non-fluorescent, but when negatively charged, becomes intensely fluorescent.

In each of these examples for mechanisms by which particles in the hole 2 may by driven axially with a force in addition to diffusion, the movement pathways themselves may be slowed down, by several different mechanisms. Examples of some of these mechanisms are illustrated in FIGS. 26, 27, and 28.

Referring to FIG. 26, a fluorophore 21 may be moved in a straight line by a migration force (such as from an electric field, magnetic field gradient, or gravitational field) if there are no obstacles in its path. However, if there are obstacles, such as an analyte particle 20 and an analyte particle 27, then the fluorophore 21 will need to go around the analyte particles, slowing down the fluorophore axial, movement. If the analyte particles have a binding interaction, they will form, a large complex 28, causing the fluorophore axial movement to be slowed down even, more. For example, a typical protein, such as Bovine Serum Albumin (BSA), has a size of 4 nm×4 nm×14 nm. With a TEPC filter 1 hole 2 diameter of 50 nm, a single BSA protein molecule would be blocking a significant fraction (0.8% to 2.9%) of the cross-sectional area of the hole 2, and hence significantly reduce the fluorophore flow.

Referring to FIG. 27, a large electrolyte cation 24 and large electrolyte anion 25 may be moved in a straight line by an electric field if there are no obstacles in its path. However, if there are obstacles, such as an analyte particle 20 and an analyte particle 27, then the cation 24 and anion 25 will need to go around, the analyte particles, slowing down the ionic axial movement. If the analyte particles have a binding interaction, they will form a large complex 28, causing the ionic axial movement to be slowed down even more.

Referring to FIG. 28, obstacles 29, 30, and 31 themselves may have an electric charge. Upon application of an electric field, they may interact in complex ways with the movement of the electrolytes or redox reagents.

Figure 29:
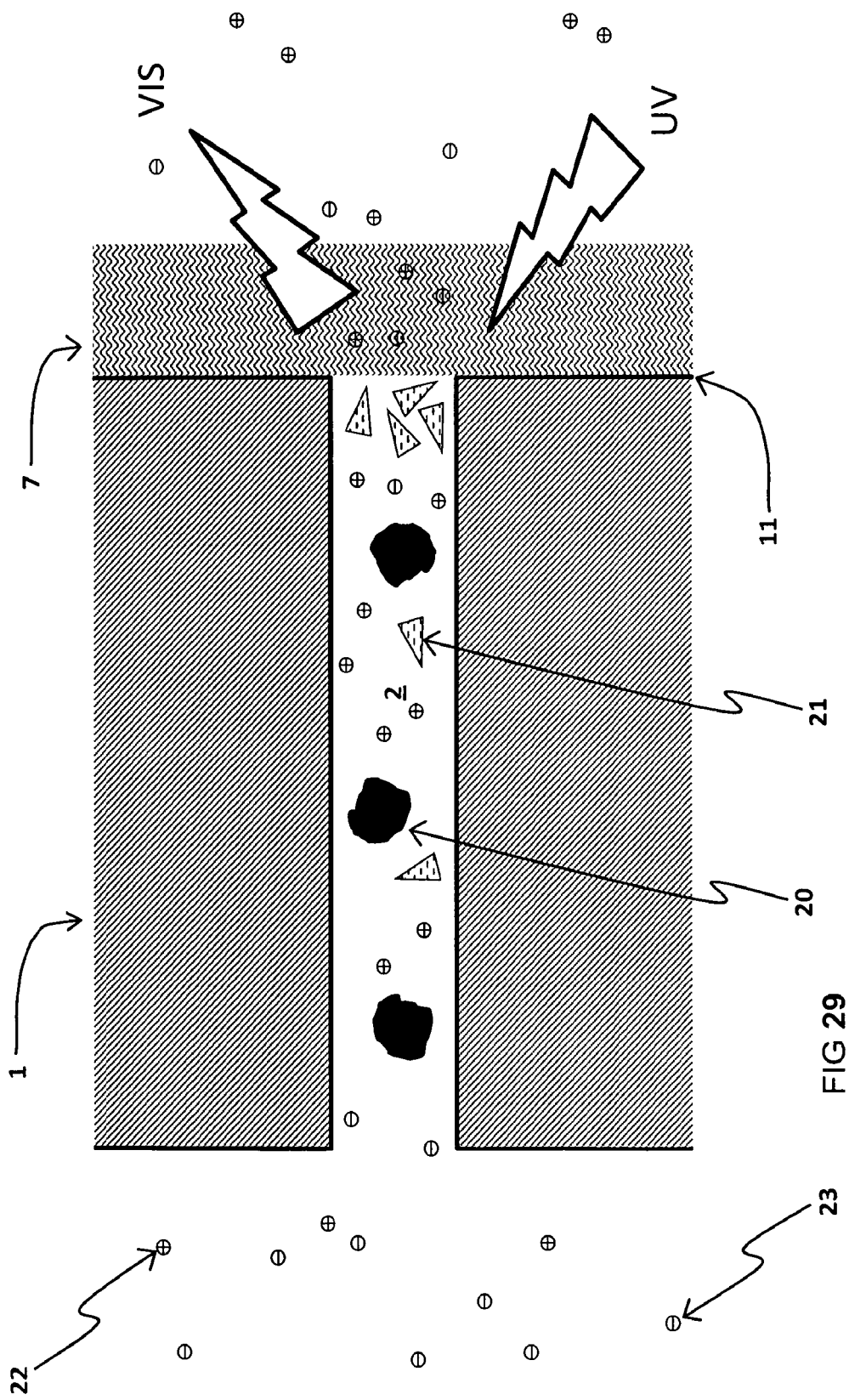
FIG. 29 is a schematic of excitation of migrated fluorophores with ultraviolet light, and their emission of visible light.
Figure 30:
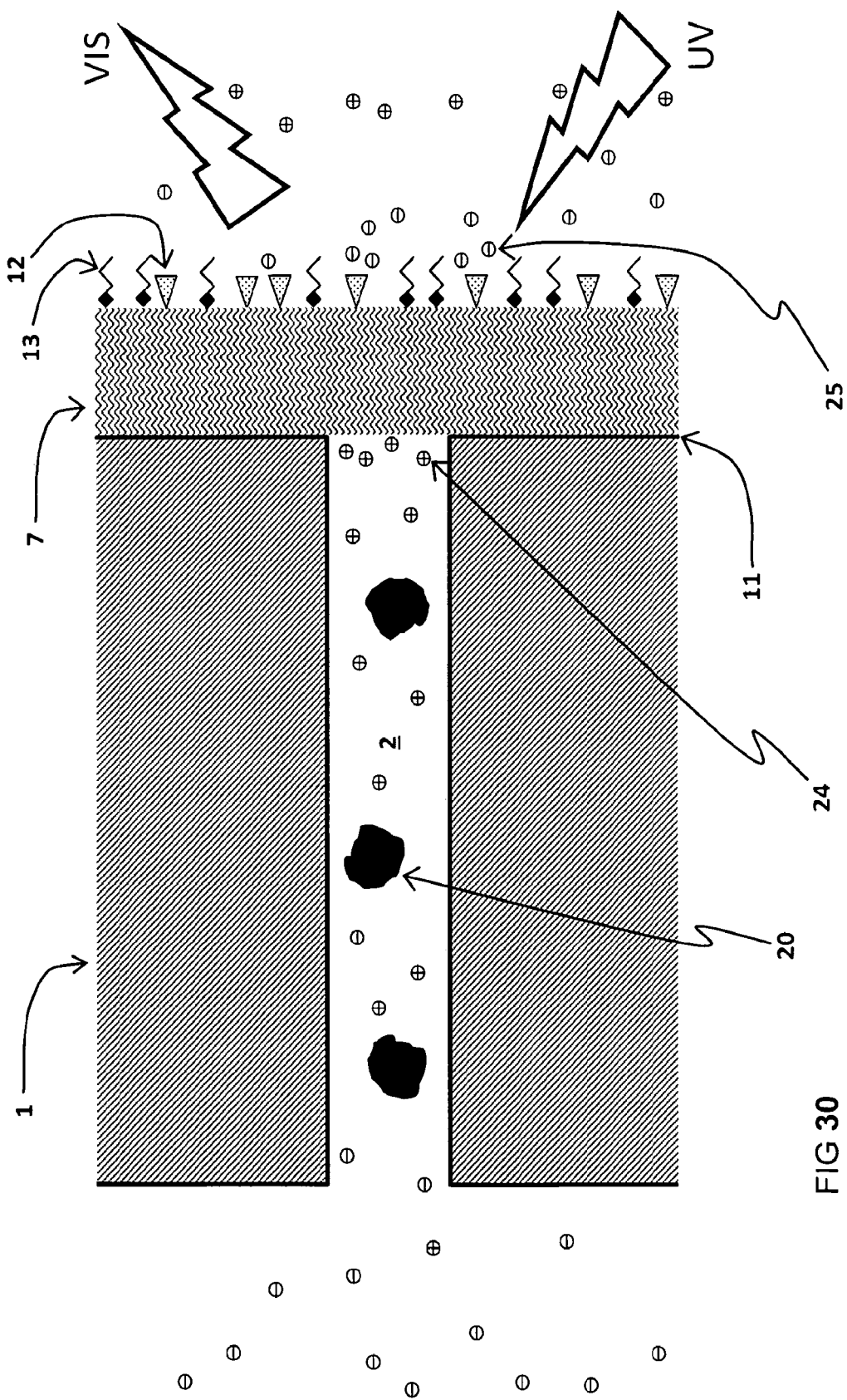
FIG. 30 is a schematic of excitation of charged fluorophores with ultraviolet light, and their emission of visible light.

The accumulation or activation of fluorophores in the vicinity of the gel 7, depending upon obstacle characteristics within, the hole 2, provides a sensitive way to perform measurements of the obstacle characteristics. FIGS. 29 and 30 illustrate the application of ultraviolet light to the fluorophores, and the resulting emitted visible light. The intensity of the emitted visible light is dependent upon the concentration of active fluorophores in the vicinity of the gel 7. Fluorophores that are located at a distance down the hole 2 will not fluoresce, because the polycarbonate material of the TEPC filter 1 is strongly absorbing for ultraviolet light. Note that although a primary advantage of this method is to avoid the need to label, an analyte particle with a fluorophore, it is within the scope of this method to include analyte particles labeled with fluorophores.

The overall apparatus in the sample loading state is shown in FIG. 32. A fluid flow of analyte, such as a complex sequence of proteins eluting from a chromatography column 32, is directed to flow into a particular region of the TEPC filter 1. A low pressure on the opposite side causes the solvent and other small molecules to pass through the TEPC filter 1 and gel 7, accumulating analyte particles within the TEPC filter 1 holes 2. As analyte particles are eluted from the chromatography column 32, the TEPC filter 1 surface is moved in a scanning motion. The different analyte particles that elute are trapped in spatially distinct, locations within the TEPC filter 1. Following this operation, a second scan may be done with, different analyte particles eluting from the chromatography column 32, producing a large number of unique binary mixtures (of controllable proportions) across the area of the TEPC filter 1. Further scans could be used to add even more complexity to the populations within the holes 2. This would be functionally equivalent to "Sandwich Array" technology, for reducing the problem of protein cross-reactivity. It is even possible to include lipid micelles, colloids, immobilized materials, or Phage Antibody Display technology within the holes 2, allowing retained, analyte particles to interact with that environment. Furthermore, it is possible to extract analyte particles from one set of holes 2 and add it to another set of holes 2.

Figure 34:
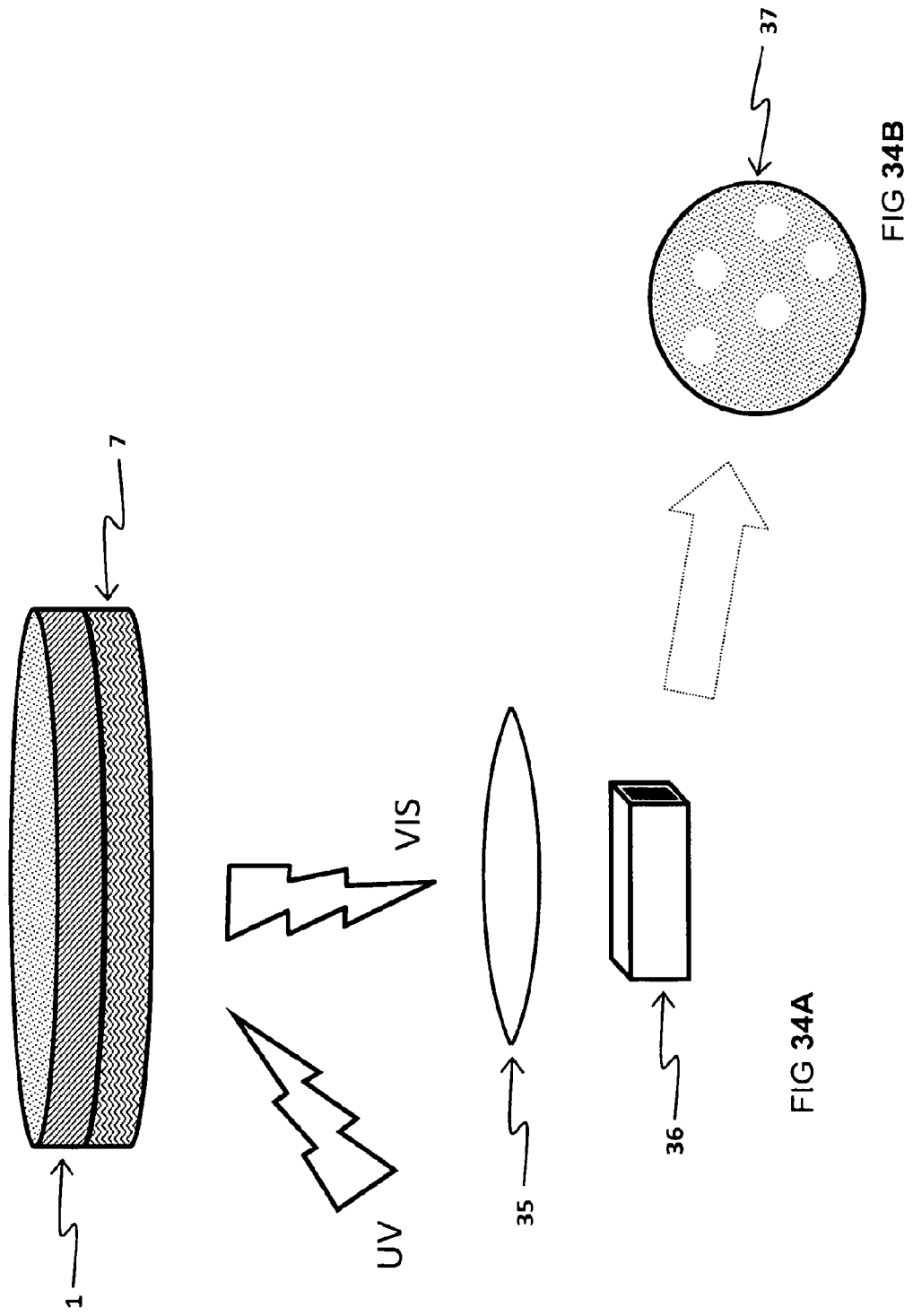
FIG. 34A is a schematic of how fluorescence is detected in an analytically useful way.
FIG. 34B is a view of the photographic image resulting from FIG. 34A.

The overall apparatus in the measurement state is shown in FIG. 34. A beam of fluorescence excitation light, such as ultraviolet, light, is directed towards a surface such as the gel 7 surface. The fluorescence emission light, such as visible light, is collected by a lens 35 or light pipe, and a photosensor 36, such as a digital camera. Information from the camera is compiled into a photographic image 37.

Figure 36:
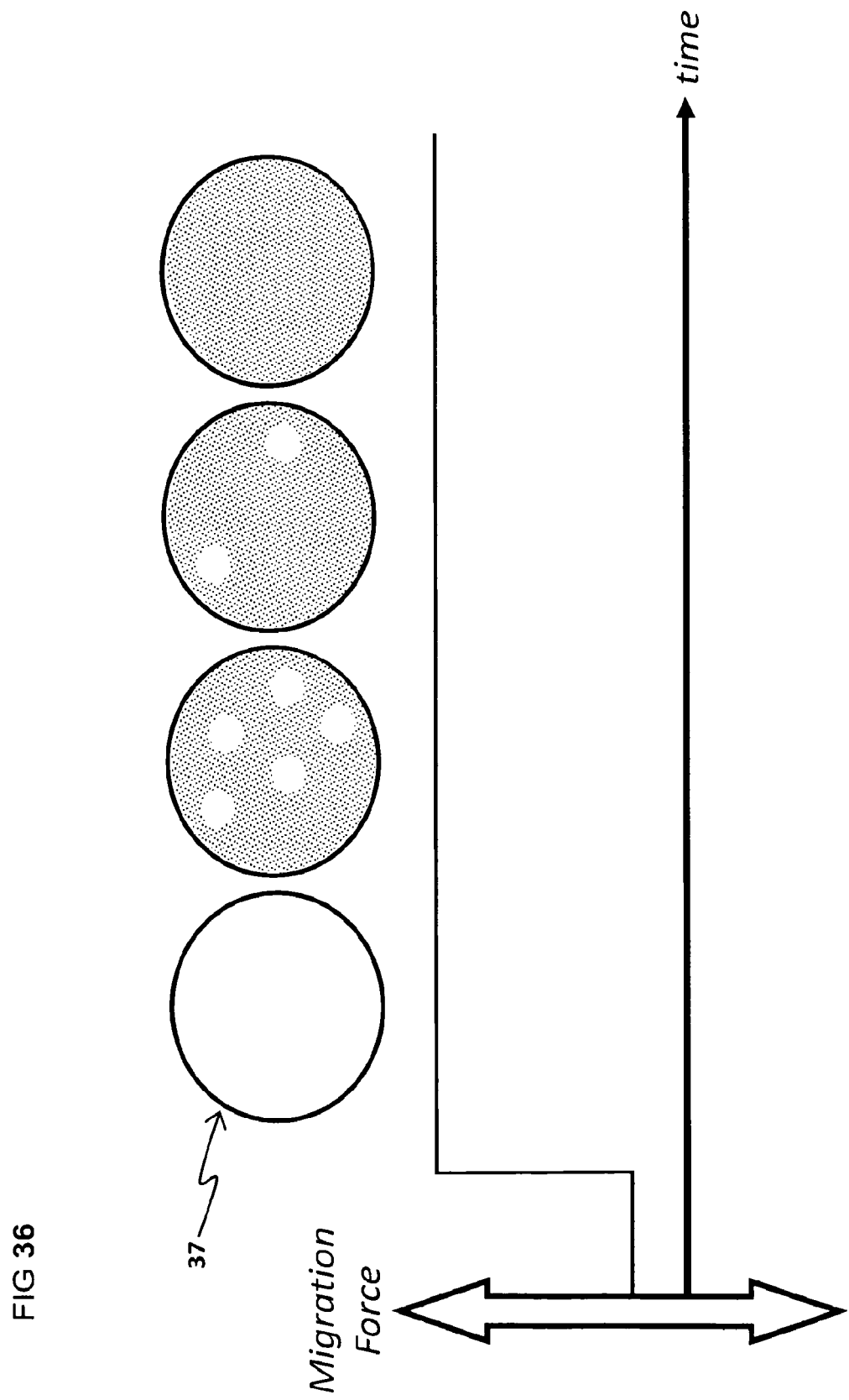
FIG. 36 is an illustration of the photographic images that evolve over time when the migration force is applied.

Referring to FIG. 36, the result of measurement is a series of changing photographic images 37 when the migration force (such as from an electric field, magnetic field gradient, or gravitational field) is applied, initially, the photographic image is relatively dark. After a brief amount, of time, most of the area is fluorescent with the exception of a few delayed areas having significant migration obstacles (e.g. analyte particles). Soon, however, as migration completes in these delayed areas, the whole area of the image becomes uniformly fluorescent. The temporal characteristics of these delayed areas, relative to the un-delayed areas, is the basis of the analytical signal.

Figure 38:
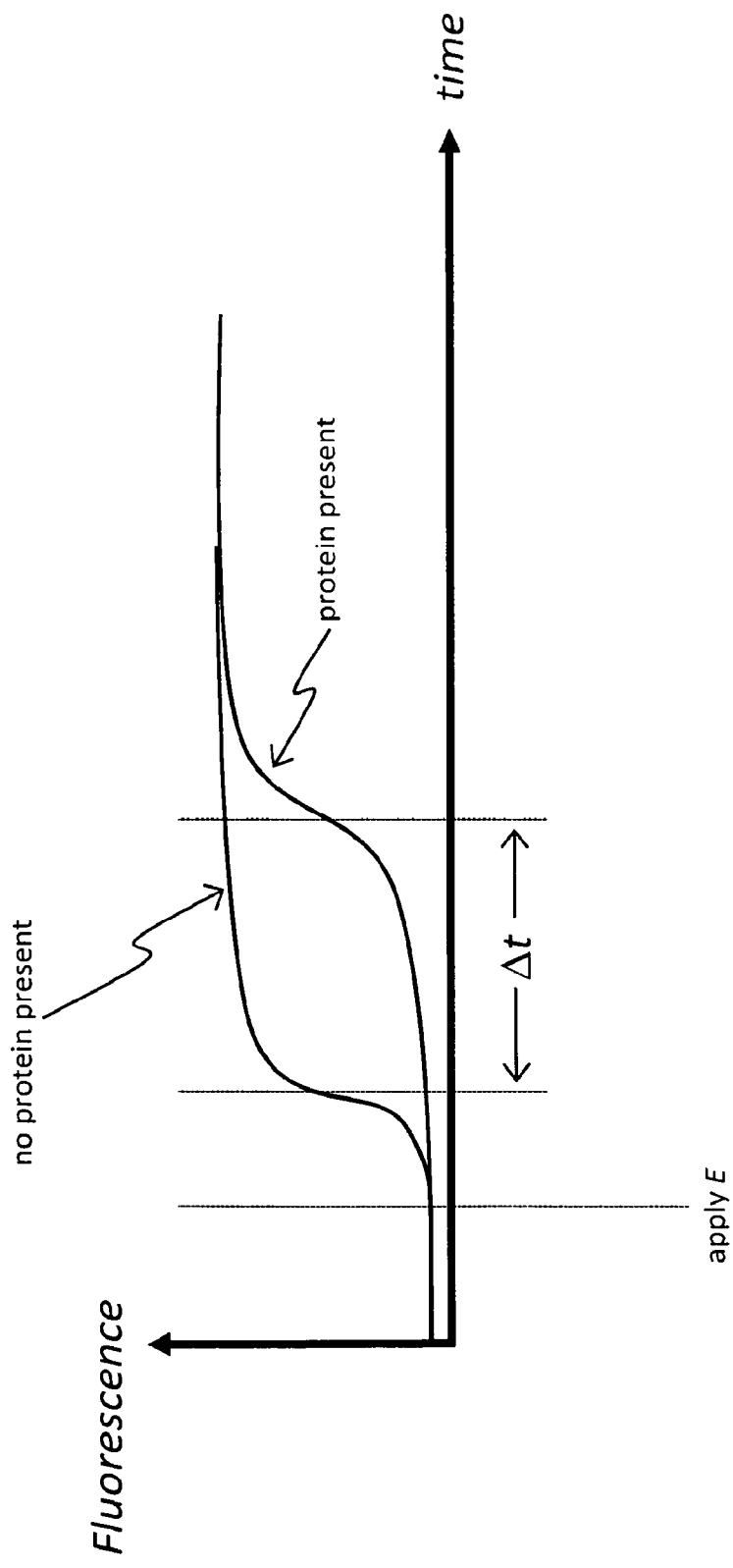
FIG. 38 is an illustration of a horizontal (temporal) shift in the fluorescence inflection point for a small grouping of holes, protein molecules absent versus protein molecules present.

Referring to FIG. 38, the fluorescence is graphed as a function of time for an area that has protein present, and another area that has no protein present. After the electric field E is actuated, the presence of protein causes a horizontal (temporal) shift in the sigmoidal curve, which can be quantified by a delta time t measurement.

Figure 40:
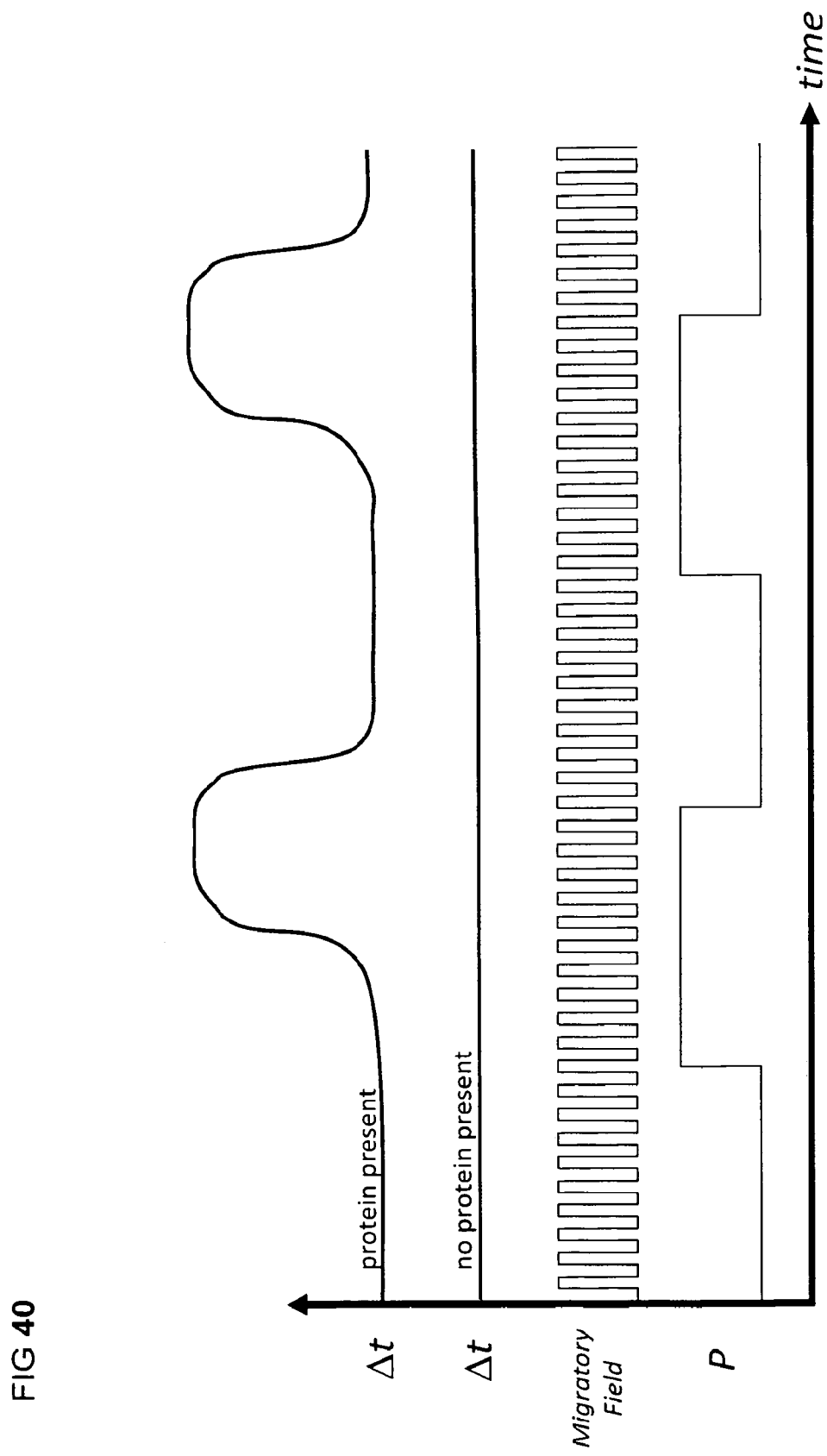
FIG. 40 is an illustration of repeated delta time measurement of the presence of protein molecules in a small grouping of holes, and the absence of protein molecules in another small grouping of holes.

Referring to FIG. 40, the theoretical results for protein present versus no protein present are compared. The migration force is repeatedly actuated in a cycle, yielding repeated delta time t measurements. On a longer time scale, the hydrodynamic pressure P is also repeatedly actuated in a cycle. When increased pressure causes protein to accumulate, the delta time increases. When the pressure is released, the protein diffuses outward, and the delta time decreases. Cycling the hydrodynamic pressure thus provides a continual series of delta time peaks that can be averaged for sensitive detection of the presence of the protein.

Figure 42:
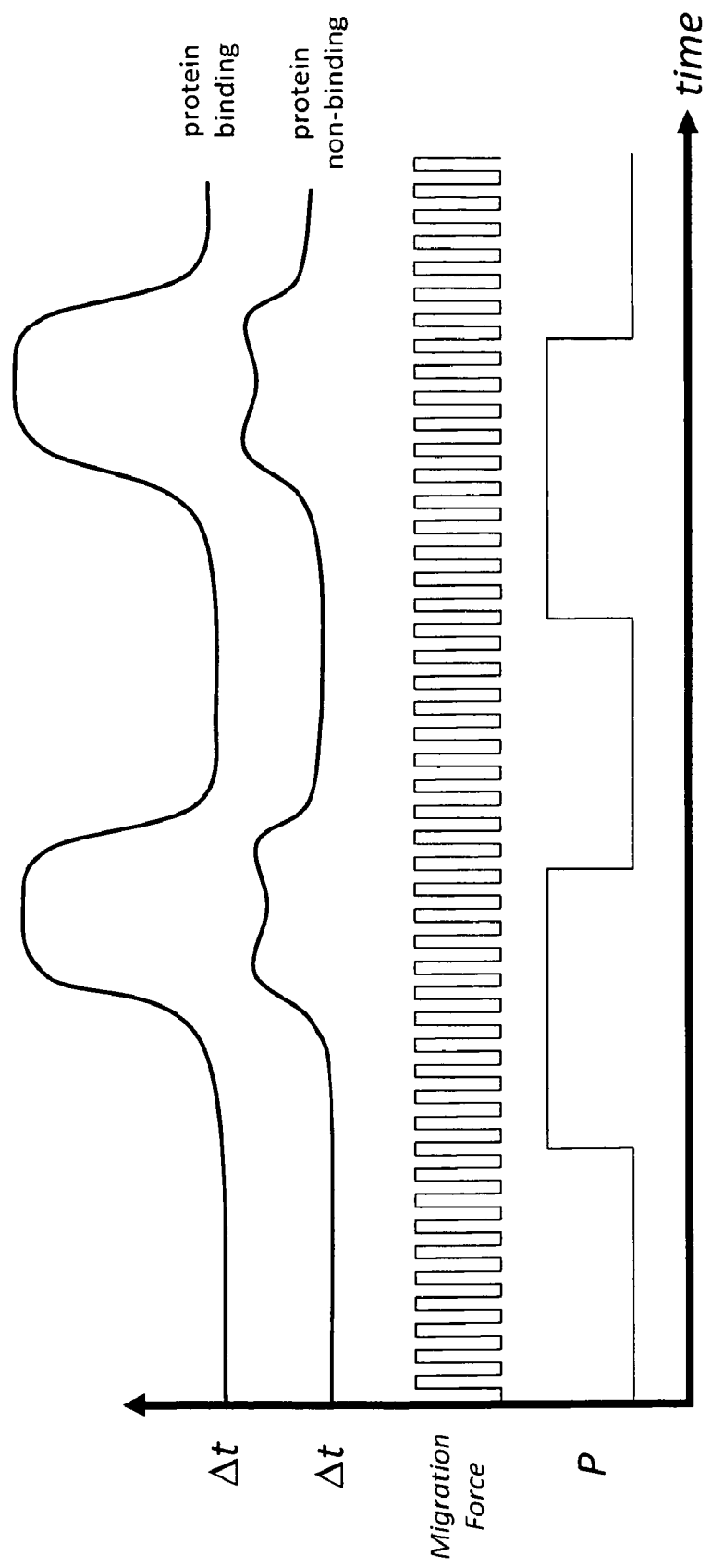
FIG. 42 is an illustration of repeated delta time measurement of protein binary interaction in a small grouping of holes, and of protein binary non-interaction in another small grouping of holes.

Referring to FIG. 42, the theoretical results for protein binding present versus protein non-binding are compared. Protein that binds to another protein will have greater steric effects, becoming a large obstacle and having a slower diffusion, rate; this results in a series of continual delta time t peaks that are of large amplitude. Protein that does not bind to another protein will have lesser steric effects, not becoming a large obstacle and not having a slower diffusion rate; this results in a series of continual delta time peaks that are of small, amplitude. Note that since there are multiple proteins present, this smaller amplitude may have multiple peaks.

A summary of the measurement results is shown in FIG. 43. The measurements provide a map of the analyte particle characteristics across the area of the TEPC filter 1. Certain areas 38 will have measurement characteristics of interest to a scientist performing the method. The identity of the contents of these areas can then be clone by a variety of techniques, such as by mass spectrometry, or by knowledge of the chromatography system that originally delivered the contents.

Substantially the same functionality may be achieved by use of similar structures, such as a perforated monolayer film instead of a TEPC/gel structure, where diffusion is radial instead, of axial.

Third Embodiment Summary

A specially-constructed, layered material forms a set of reservoirs that are loaded with a variety of spatially-separated analyte particles, and said layered material sampled by mass spectrometry. This yields a map of the compositions of the various analyte particles, which can provide useful information about biological samples.

Method in Accordance with a Third Embodiment of the Invention

In a method in accordance with a third embodiment of the invention, the holes of a TEPC filter (or functionally equivalent structure) are restricted at the openings. Homogeneous or heterogeneous populations of analyte particles within a controlled matrix are loaded into the TEPC filter holes, and the hole ends are tightly capped by spheroids forcefully corked into the hole ends. The assembly is loaded info a vacuum chamber, targeted by a laser beam, and the resulting vapor directed into a mass spectrometry chamber. Ionization and mass/charge detection provides a means of identification of the analyte particles.

The method of the invention, will now be described by way of reference to FIGS. 44 to 48.

Figure 44:
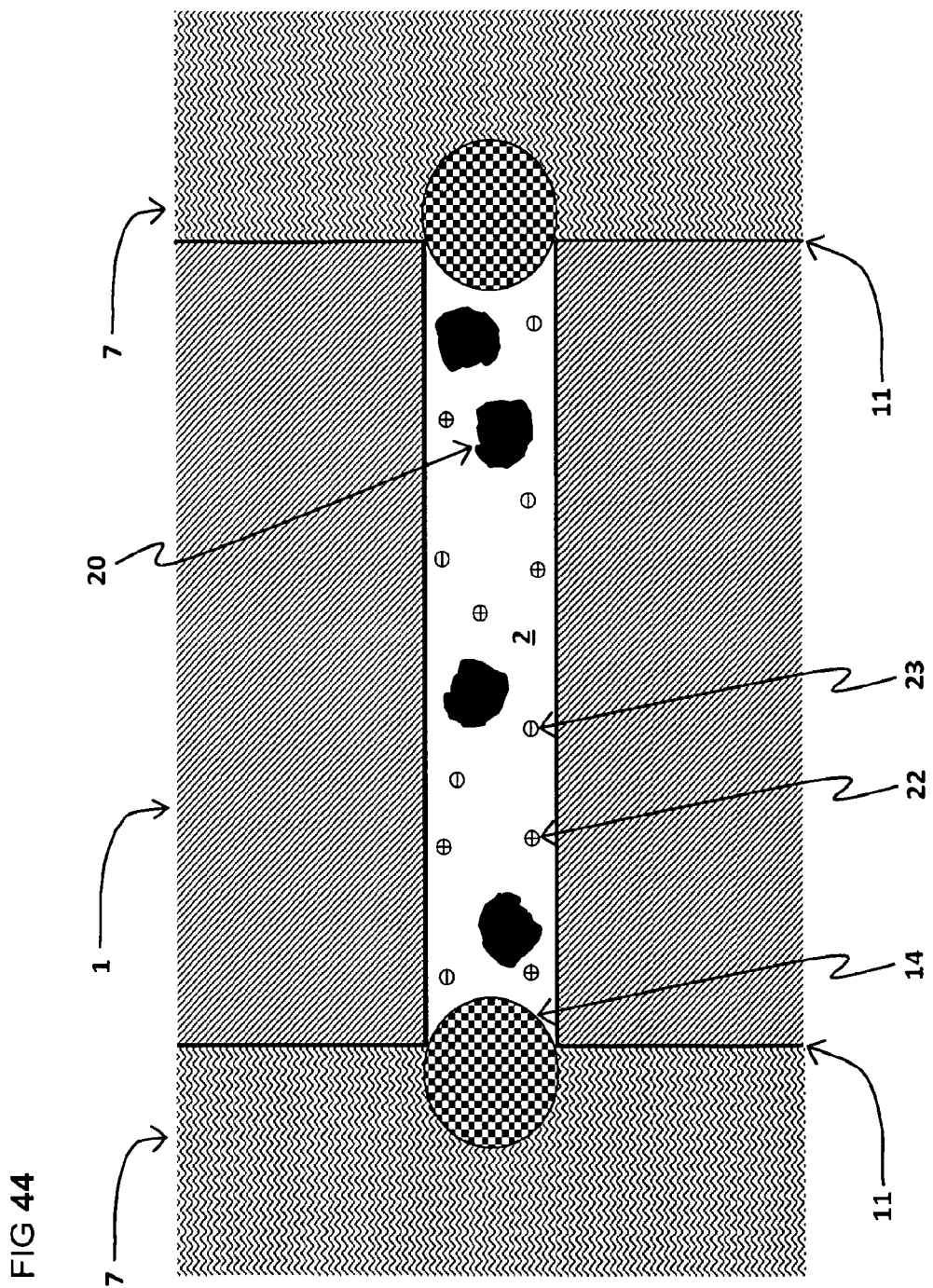
FIG. 44 is a schematic of a first stage of permanent entrapment of molecular species in the perforated material.

Referring to FIG. 44, a composition of analyte particles 20, 22, and 23 is enclosed within the hole 2 of TEPC filter 1, by having a spheroid 14 at each end of the hole 2.

Figure 45:
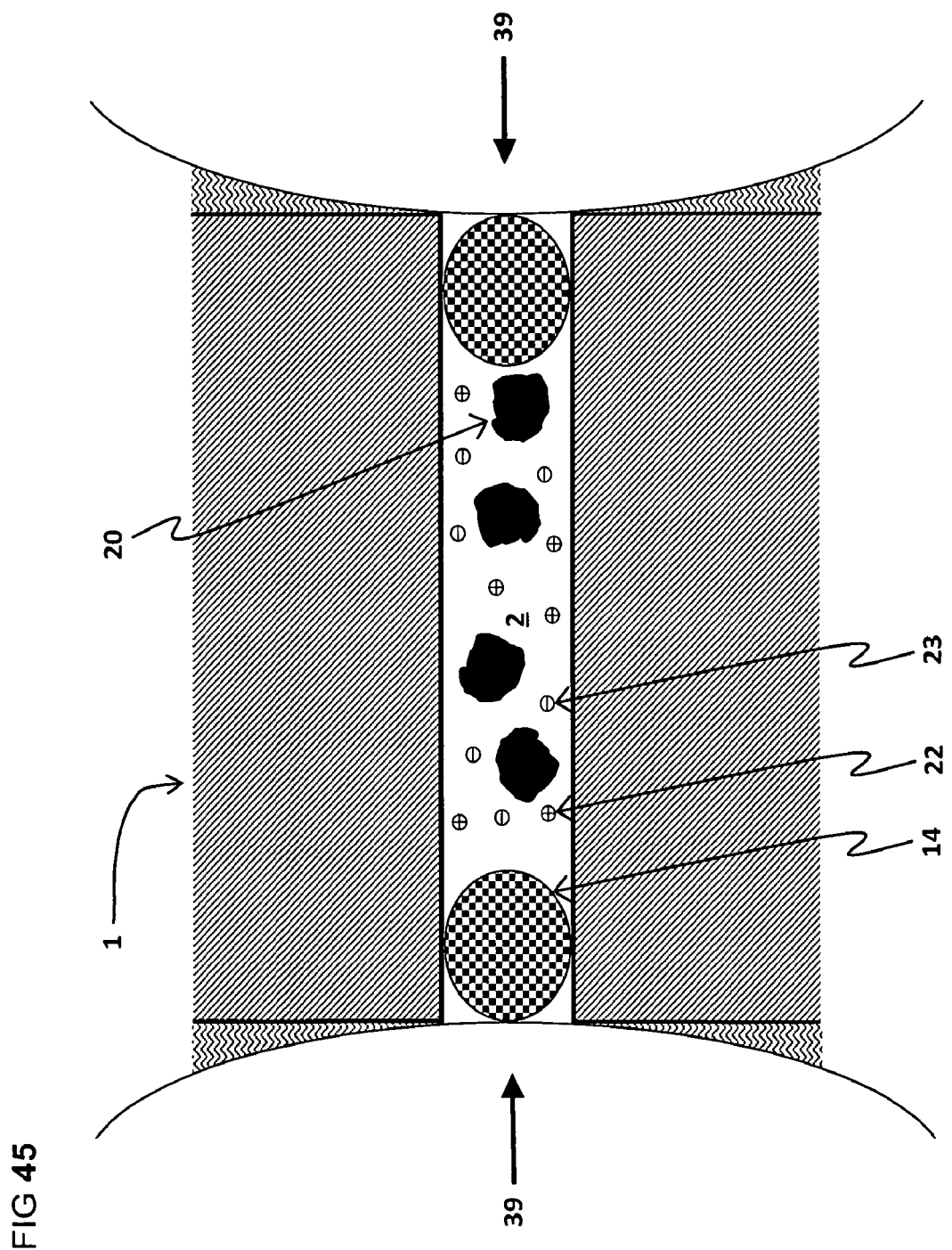
FIG. 45 is a schematic of a second stage of permanent entrapment of molecular species in the perforated material.
Figure 46:
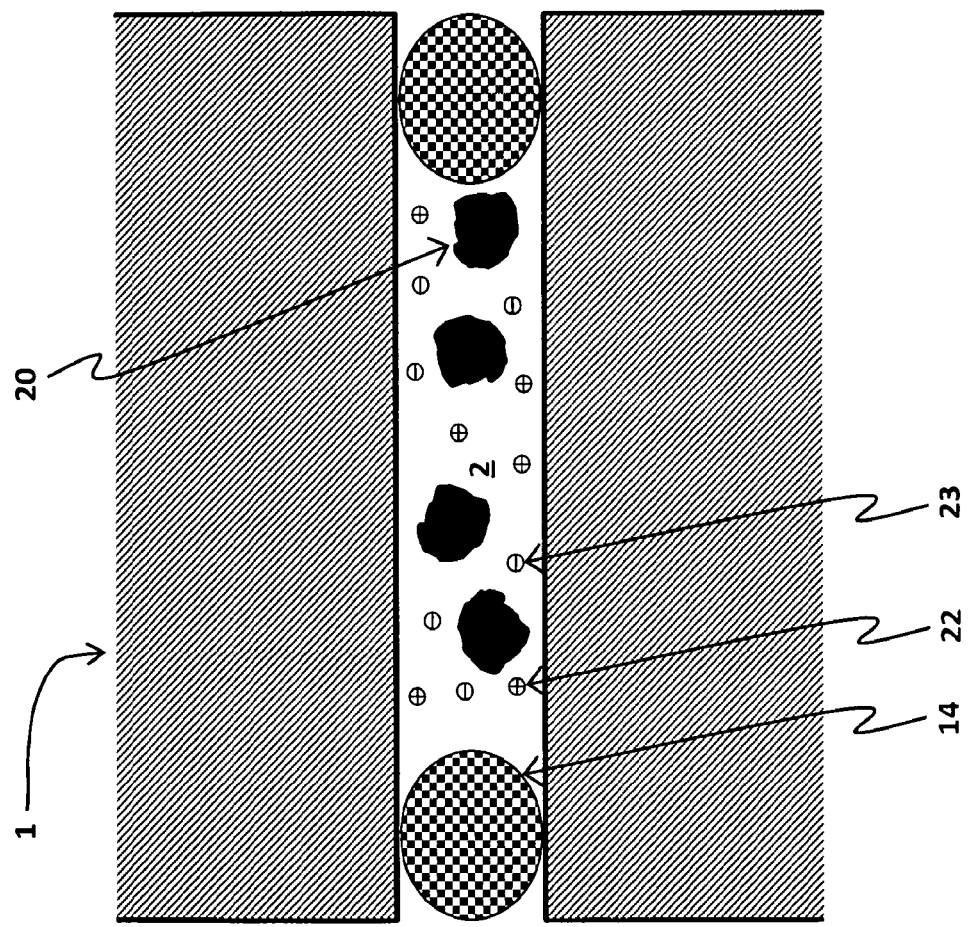
FIG. 46 is a schematic of permanently trapped molecular species in the perforated material.

Referring to FIGS. 45 and 46, tightly squeezing the TEPC filter 1 between two smooth rollers to exert a compressive force 39 would cause each spheroid 14 to stopper both ends of the hole 2. The TEPC filter 1 could then be removed from the preparatory apparatus, yielding a stable material shown in FIG. 46 that contains the analyte particles.

Figure 47:
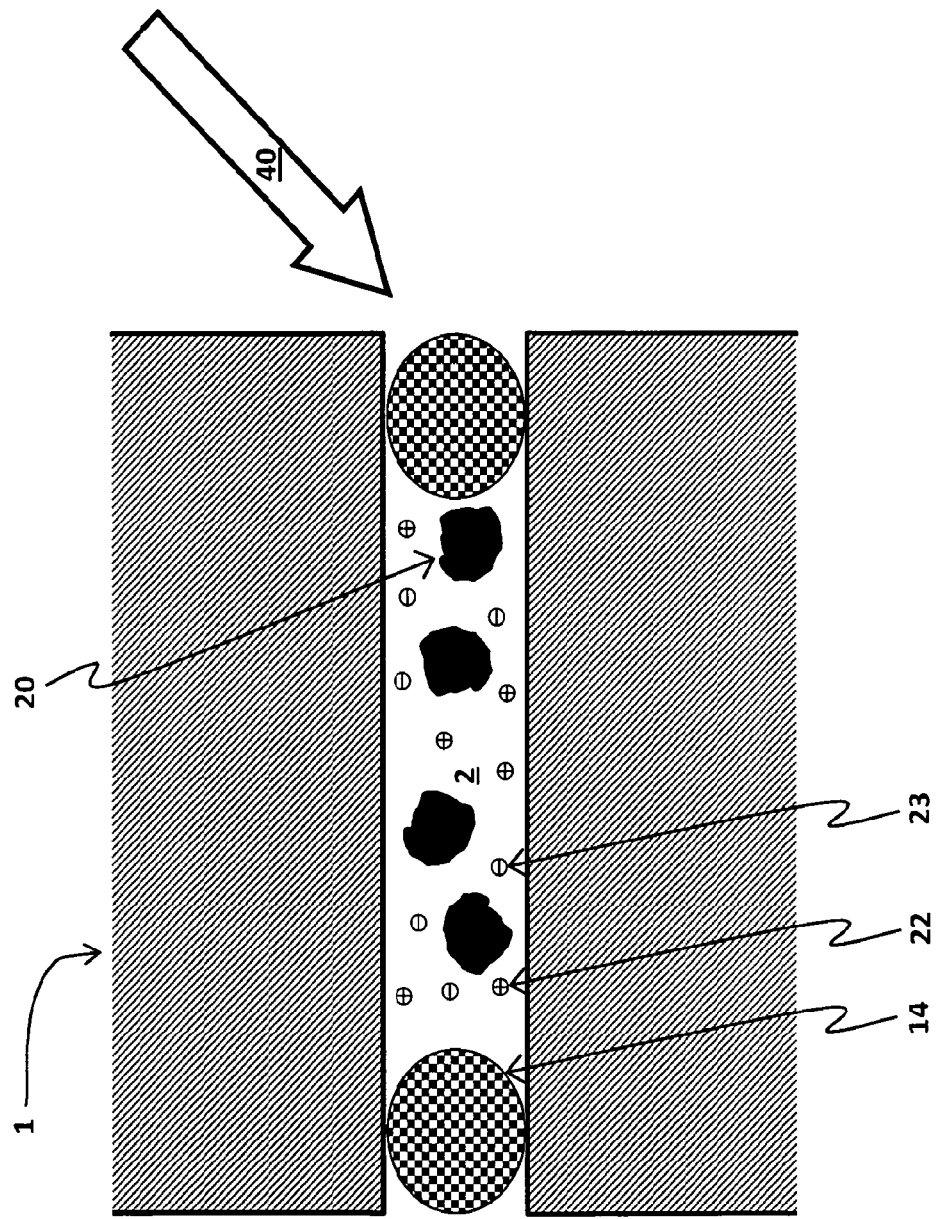
FIG. 47 is a schematic of illumination by a laser of trapped molecular species in a hole of the perforated material.

Referring to FIG. 47, the stable material is put into a vacuum chamber. The aqueous matrix containing the analyte particles within the hole 2 is protected from the vacuum by the spheroids 14 stoppering the hole 2 and sealing in the aqueous matrix. Additional sealing may be provided with, a thin polymer film overcoat. An intense, focused laser beam 40 is then directed at the hole 2.

Figure 48:
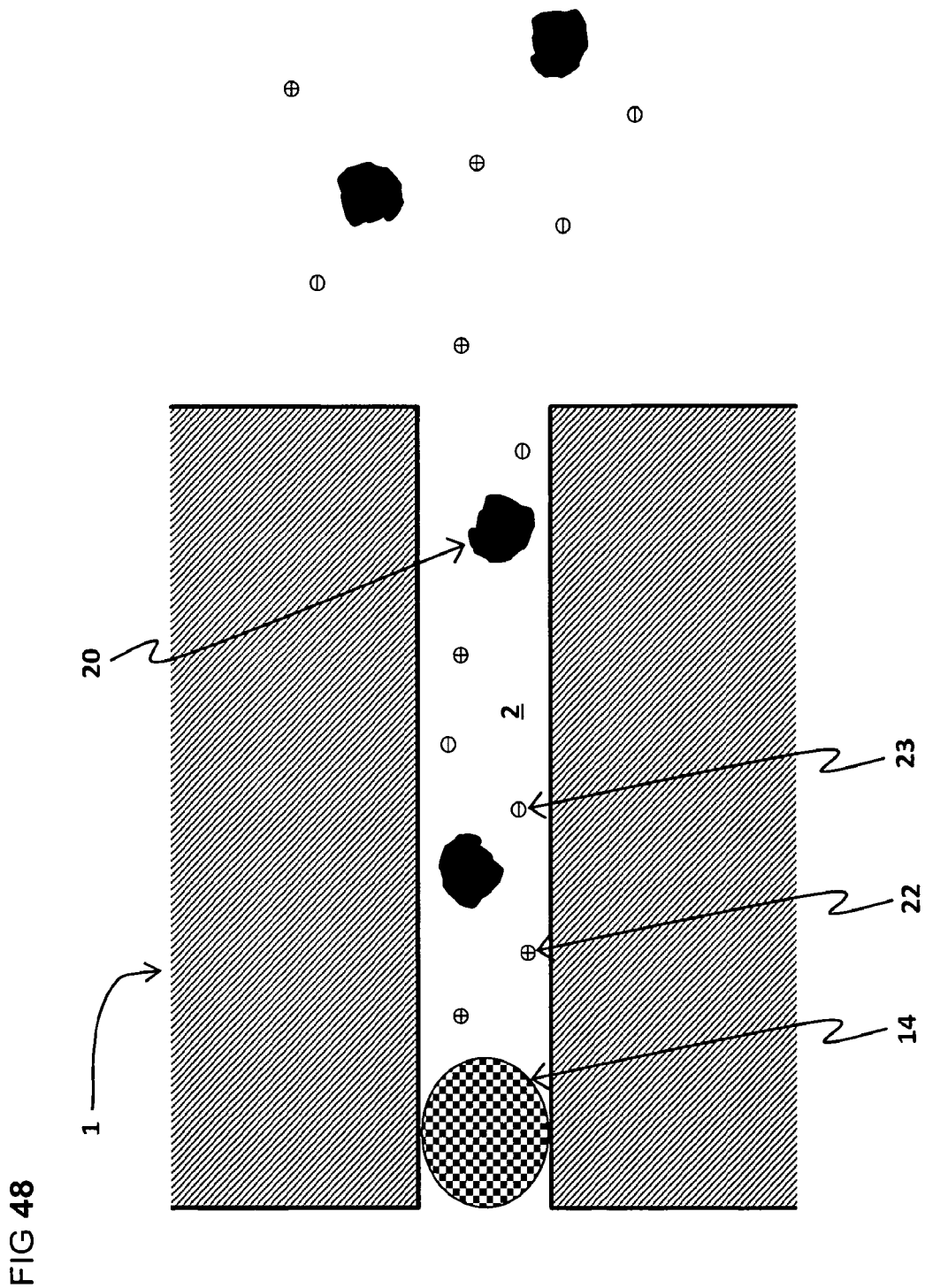
FIG. 48 is a schematic of shows vaporization of the trapped molecular species of FIG. 43.

Referring to FIG. 48, the laser beam would vaporize the upper stopper of the TEPC filter 1 hole 2, causing the aqueous matrix to explode outwards into the vacuum, dispersing it as a gas. This is analogous to matrix-assisted laser desorption ionization (MALDI) analysis. However, the biological sample receives much less thermal stress, leading to a less complex fragmentation pattern. This reduced complexity may be analytically useful.

SUMMARY

The scope of these Methods covers the tasks of detection, characterization, and identifying of analyte panicles, and the characterization of any interactions involving them, using the properties of nanoscale reservoirs.

Current methods for performing these tasks suffer from a variety of deficiencies, such as the interference from labeling techniques and cross-reactivity. These deficiencies are eliminated. Furthermore, the methods are useful for analysis of extremely low concentrations of analyte particles.

A specific field where these Methods would be useful is in biotechnology, for the measurement of protein interactions. There are an extremely large number of proteins used in every biological system, which interact in a complex network that is dependent on many factors. Diseases distort this network, adding or removing components and interaction pathways. An understanding of these systems allows early diagnosis of disease, and a way to chemically repair the system through drug therapy. The most populous and stable proteins within these systems have been partially studied, but much further study is warranted. The addition of new and more powerful tools, such as the Methods described herein, to the repertoire of medical researchers would deepen the understanding of the protein networks and allow the development of new drug therapies.

The term "particles" as used herein includes molecules, cells, multicellular structures, subcellular components, viruses, prions, proteins, polymers, ions, colloids, and fluorophores. The particles may be suspended or dissolved. The particles do not necessarily need to be biologically relevant.

The term "analyte" as used herein describes particles that are to be measured.

The term "gel" as used herein is not restricted to its strict technical definition, but rather includes generally any material that is relevant to restricting diffusion of analyte particles. The term "gel" is intended to include, but is not limited to, gelatin, agarose, polyacrylamide, polyacrylate, permeable polymers, permeable copolymers, starch, aerogel, collodion, dialysis membrane, immiscible fluid, any of the above-listed materials in a chemically modified form, any of the above-listed materials embedded with particles, and any combination of the above-listed materials.

The term "immiscible fluid" as used herein includes fluids that are immiscible with the analyte particle matrix.

The term "large" as used herein describes those particles that can not pass through the restriction at the end of the TEPC filter hole, such as by the gel. The term "small" as used herein describes those particles that can pass through the restriction at the end of the TEPC filter hole, such as by the gel.

The term "force" as used herein includes a force resulting from an electric field, a force resulting from a magnetic field gradient, a force resulting from a gravitational field, centripetal force, centrifugal force, force resulting from hydrodynamic pressure, a force resulting from hydrostatic pressure, or a combination of such forces.

Electric fields may be generated capacitively, without direct electrode contact with ionic or redox species. Multiple sets of electrodes may be used, as needed to achieve the necessary electric fields. For example, one set of electrodes may be used to exert strong migration forces, while another set of electrodes is used for analyte particle measurement.

Measurement of electric current may be structured to constitute resistance, conductance, impedance, capacitance, and inductance measurements, and combinations thereof. For example, characterization of lipid micelles, whole cells, or other materials with impedance boundaries may be assisted by capacitance measurements, and characterization of chiral analytes may be assisted by inductance measurements.

Analyte particles may be delivered to the apparatus by local rupture of intact cells, or by other techniques, in addition to standard chromatographic techniques.

The holes or perforations in said TEPC material, or its junctional equivalent, may be sized for close fitting of individual cells, so that electrical impedance and capacitance are determined largely through the bulk of the cell.

The methods described herein may be combined with conventional microchannel array technology, commonly referred to as "lab-on-a-chip" technology.

While the present invention has been described with reference to certain preferred embodiments, one of ordinary skill in the art will recognize that other additions, deletions, substitutions, modifications, and improvements can be made while remaining within the spirit and scope of the present invention as defined by the claims.

The invention claimed is:

1. A method for analyzing an analyte, comprising:
   (a). providing a sheet of material having a plurality of through holes, the through holes having openings on both faces of the sheet of material;
   (b). restricting openings of the through holes on at least one face of the sheet of material;
   (c). inserting an analyte into a sub-population of said through holes, wherein passage of the analyte through the through holes is restricted by the restricting in step (b);
   (d). applying an electric field through said through holes containing the analyte; and
   (e). measuring a change in electric current flow with time, wherein the change is indicative of the diffusion rates of said analyte diffusing out of the through holes.

2. The method of claim 1, wherein said sheet of material comprises a material having a property selected from the group consisting of: being electrically insulating; being chemically inert; having a thickness in the range of 500 nm to 1000000 nm; having a thickness in the range of 1 nm to 10 cm; having through holes of diameters in the range of 10 nm to 5000 nm; having through holes of diameters in the range of 1 nm to 1 cm; having through holes with an inner surface that is chemically derivatized; having an outer surface that is chemically derivatized; and having holes filled with a gel.

3. The method of claim 1, wherein said sheet of material is selected from the group consisting of: a polycarbonate; a track-etched polycarbonate; a polymer drilled with a plurality of holes; a polymer chemically etched with a plurality of holes; a glass drilled with a plurality of holes; a glass chemically etched with a plurality of holes; a perforated polymer film; a perforated monolayer film; and a perforated multilayer film.

4. The method of claim 1, wherein the restricting in step (b) comprises restricting said through hole openings by a layer of a gel in contact with a surface of said sheet of material.

5. The method of claim 4, wherein said gel comprises a material selected from the group consisting of: a gelatin; an agarose; a polyacrylamide; a polyacrylate; a permeable polymer; a permeable copolymer; a starch; an aerogel; a collodion; and a dialysis membrane.

6. The method of claim 1, wherein the restricting in step (b) comprises restricting said hole openings using spheroids having diameters sufficient to cause restriction of fluid flow through said through holes.

7. The method of claim 6, further comprising holding the spheroids in position relative to the through hole openings by an electric field, a magnetic field gradient, a gravitational field, a centripetal force, a centrifugal force, hydrodynamic pressure, hydrostatic pressure, or chemical bonds.

8. The method of claim 6, further comprising holding the spheroids in position relative to the through hole openings using a gel matrix.

9. The method of claim 8, further comprising removing said spheroids from said gel matrix.

10. The method of claim 1, wherein the measuring in step (e) comprises measuring electric current flow through a selected area of the sheet of material using an amperometer.

11. The method of claim 10, wherein said selected area is selected by contacting one end of an insulating tube filled with an electrically conductive fluid with said sheet of material, wherein the contact area on the sheet of material with the electrically conductive fluid is selected for measuring electric current flow.

12. The method of claim 10, wherein said selected area is selected by applying an insulating sheet with a hole to the surface of said sheet of material, wherein the area on the sheet of material corresponding to the hole on the insulating sheet is selected for measuring electric current flow.

13. The method of claim 10, wherein said selected area is selected by applying an insulating water-immiscible fluid to the surface of said sheet of material, and contacting the surface of said sheet of material with one end of an insulating tube filled with an electrically conductive fluid, wherein the contact area on the sheet of material with the electrically conductive fluid is selected for measuring electric current flow.

14. The method of claim 1, further comprising applying a migration force axially through said through holes containing the analyte.

15. The method of claim 14, wherein the migration force is selected from the group consisting of: a force resulting from an electric field; a force resulting from a magnetic field gradient; a force resulting from a gravitational field; a centripetal force; a centrifugal force; a force resulting from hydrodynamic pressure; a force resulting from hydrostatic pressure; and combinations thereof.

16. The method of claim 1, wherein the analyte is concentrated in the through holes.

17. The method of claim 1, wherein after the analyte diffuses out of the through holes, the analyte is reinserted into the through holes and steps (c)-(d) are repeated.

18. The method of claim 1, wherein the through holes are a first set of through holes, and wherein the analyte is extracted from the first set of through holes and added to a second set of through holes.

* * * * *